(12) United States Patent
Nguyen et al.

(10) Patent No.: US 9,149,610 B2
(45) Date of Patent: Oct. 6, 2015

(54) METHOD AND APPARATUS FOR IMPROVING DELIVERY OF AN AGENT TO A KIDNEY

(75) Inventors: Binh T Nguyen, Newark, CA (US); Paul M Consigny, San Jose, CA (US); Randy Shen, Sunnyvale, CA (US); Michael J Leonard, Palo Alto, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 13/158,757

(22) Filed: Jun. 13, 2011

(65) Prior Publication Data

US 2011/0245766 A1  Oct. 6, 2011

Related U.S. Application Data

(63) Continuation-in-part of application No. 11/756,376, filed on May 31, 2007, now Pat. No. 8,216,209, which is a continuation-in-part of application No. 12/902,405, filed on Oct. 12, 2010, which is a continuation of application No. 13/154,258, filed on Jun. 6, 2011.

(51) Int. Cl.
*A61M 31/00* (2006.01)
*A61M 25/10* (2013.01)
*A61F 2/01* (2006.01)
(Continued)

(52) U.S. Cl.
CPC ............... *A61M 25/10* (2013.01); *A61F 2/013* (2013.01); *A61L 2300/432* (2013.01); *A61M 25/04* (2013.01); *A61M 2025/0057* (2013.01);
(Continued)

(58) Field of Classification Search
CPC ............... A61M 2025/1052; A61M 2025/004; A61M 31/00; A61M 2025/0073; A61M 25/04; A61M 2025/0057; A61M 25/0074; A61M 2206/20; A61M 25/10
USPC .......................... 604/509, 523, 96.01–103.14
See application file for complete search history.

(56) References Cited

U.S. PATENT DOCUMENTS 2,701,559 A  2/1955 Cooper
3,105,492 A  10/1963 Jeckel
(Continued)

FOREIGN PATENT DOCUMENTS

DE  3640745  6/1987
DE  3823060  1/1989
(Continued)

OTHER PUBLICATIONS

Abbott Cardiovascular Systems, Final Office Action mailed Jun. 5, 2014 for U.S. Appl. No. 13/446,768.
(Continued)

*Primary Examiner* — Bhisma Mehta
*Assistant Examiner* — Brandy S Lee
(74) *Attorney, Agent, or Firm* — Randy Shen, Esq.; Blakely Sokoloff Taylor & Zafman LLP

(57) ABSTRACT

Methods for more uniformly delivering drugs or other treatment agents locally to the vasculature of a mammal are disclosed. These methods use one or more strategies to facilitate rapid mixing with the blood flowing past a device or otherwise improve the uniformity of drug delivery. Some of these strategies employ medical devices with diffusion members.

9 Claims, 25 Drawing Sheets

(51) Int. Cl.
    *A61M 25/04* (2006.01)
    *A61M 25/00* (2006.01)

(52) U.S. Cl.
    CPC .. *A61M2025/0073* (2013.01); *A61M 2025/105* (2013.01); *A61M 2206/14* (2013.01)

(56) References Cited

U.S. PATENT DOCUMENTS

| | | |
|---|---|---|
| 3,657,744 A | 4/1972 | Ersek |
| 3,868,956 A | 3/1975 | Alfidi et al. |
| 3,952,747 A | 4/1976 | Kimmell, Jr. |
| 3,993,078 A | 11/1976 | Bergentz et al. |
| 4,130,904 A | 12/1978 | Whalen |
| 4,140,126 A | 2/1979 | Choudhury |
| 4,159,719 A | 7/1979 | Haerr |
| 4,323,071 A | 4/1982 | Simpson et al. |
| 4,387,952 A | 6/1983 | Slusher |
| 4,503,569 A | 3/1985 | Dotter |
| 4,504,354 A | 3/1985 | George et al. |
| 4,512,338 A | 4/1985 | Balko et al. |
| 4,516,972 A | 5/1985 | Samson |
| 4,531,933 A | 7/1985 | Norton et al. |
| 4,553,545 A | 11/1985 | Maass et al. |
| 4,560,374 A | 12/1985 | Hammerslag |
| 4,580,568 A | 4/1986 | Gianturco |
| 4,616,652 A | 10/1986 | Simpson |
| 4,619,246 A | 10/1986 | Molgaard-Nielsen et al. |
| 4,649,922 A | 3/1987 | Wiktor |
| 4,650,466 A | 3/1987 | Luther |
| 4,655,771 A | 4/1987 | Wallsten |
| 4,665,918 A | 5/1987 | Garza et al. |
| 4,681,110 A | 7/1987 | Wiktor |
| 4,693,243 A | 9/1987 | Buras |
| 4,706,671 A | 11/1987 | Weinrib |
| 4,733,665 A | 3/1988 | Palmaz |
| 4,739,762 A | 4/1988 | Palmaz |
| 4,740,207 A | 4/1988 | Kreamer |
| 4,748,982 A | 6/1988 | Horzewski et al. |
| 4,760,849 A | 8/1988 | Kropf |
| 4,762,128 A | 8/1988 | Rosenbluth |
| 4,767,418 A | 8/1988 | Deininger et al. |
| 4,768,507 A | 9/1988 | Fischell et al. |
| 4,776,337 A | 10/1988 | Palmaz |
| 4,793,348 A | 12/1988 | Palmaz |
| 4,795,458 A | 1/1989 | Regan |
| 4,800,882 A | 1/1989 | Gianturco |
| 4,830,003 A | 5/1989 | Wolff et al. |
| 4,848,343 A | 7/1989 | Wallsten et al. |
| 4,856,516 A | 8/1989 | Hillstead |
| 4,870,966 A | 10/1989 | Dellon et al. |
| 4,877,030 A | 10/1989 | Beck et al. |
| 4,878,906 A | 11/1989 | Lindemann et al. |
| 4,886,062 A | 12/1989 | Wiktor |
| 4,887,997 A | 12/1989 | Okada |
| 4,892,539 A | 1/1990 | Koch |
| 4,893,623 A | 1/1990 | Rosenbluth |
| 4,907,336 A | 3/1990 | Gianturco |
| 4,913,141 A | 4/1990 | Hillstead |
| 4,921,479 A | 5/1990 | Grayzel |
| 4,921,484 A | 5/1990 | Hillstead |
| 4,922,905 A | 5/1990 | Strecker |
| 4,923,464 A | 5/1990 | DiPisa, Jr. |
| 4,943,346 A | 7/1990 | Mattelin |
| 4,950,227 A | 8/1990 | Savin et al. |
| 4,963,022 A | 10/1990 | Sommargren |
| 4,969,458 A | 11/1990 | Wiktor |
| 4,969,890 A | 11/1990 | Sugita et al. |
| 4,986,831 A | 1/1991 | King et al. |
| 4,988,356 A | 1/1991 | Crittenden et al. |
| 4,990,155 A | 2/1991 | Wilkoff |
| 4,994,071 A | 2/1991 | MacGregor |
| 4,998,539 A | 3/1991 | Delsanti |
| 5,002,560 A | 3/1991 | Machold et al. |
| 5,007,926 A | 4/1991 | Derbyshire |
| 5,015,253 A | 5/1991 | MacGregor |
| 5,019,085 A | 5/1991 | Hillstead |
| 5,019,090 A | 5/1991 | Pinchuk |
| 5,026,377 A | 6/1991 | Burton et al. |
| 5,034,001 A | 7/1991 | Garrison et al. |
| 5,035,706 A | 7/1991 | Giantureo et al. |
| 5,037,377 A | 8/1991 | Alonso |
| 5,037,392 A | 8/1991 | Hillstead |
| 5,037,427 A | 8/1991 | Harada et al. |
| 5,053,008 A | 10/1991 | Bajaj |
| 5,059,211 A | 10/1991 | Stack et al. |
| 5,061,273 A | 10/1991 | Yock |
| 5,061,275 A | 10/1991 | Wallsten et al. |
| 5,062,829 A | 11/1991 | Pryor et al. |
| 5,064,435 A | 11/1991 | Porter |
| 5,071,407 A | 12/1991 | Termin et al. |
| 5,073,694 A | 12/1991 | Tessier et al. |
| 5,078,720 A | 1/1992 | Burton et al. |
| 5,078,726 A | 1/1992 | Kreamer |
| 5,078,736 A | 1/1992 | Behl |
| 5,084,065 A | 1/1992 | Weldon et al. |
| 5,089,005 A | 2/1992 | Harada |
| 5,089,006 A | 2/1992 | Stiles |
| 5,092,877 A | 3/1992 | Pinchuk |
| 5,100,429 A | 3/1992 | Sinofsky et al. |
| 5,102,417 A | 4/1992 | Palmaz |
| 5,104,404 A | 4/1992 | Wolff |
| 5,108,416 A | 4/1992 | Ryan et al. |
| 5,108,417 A | 4/1992 | Sawyer |
| 5,116,318 A | 5/1992 | Hillstead |
| 5,116,360 A | 5/1992 | Pinchuk et al. |
| 5,116,365 A | 5/1992 | Hillstead |
| 5,122,154 A | 6/1992 | Rhodes |
| 5,123,917 A | 6/1992 | Lee |
| 5,133,732 A | 7/1992 | Wiktor |
| 5,133,733 A | 7/1992 | Rasmussen et al. |
| 5,135,536 A | 8/1992 | Hillstead |
| 5,158,548 A | 10/1992 | Lau et al. |
| 5,161,547 A | 11/1992 | Tower |
| 5,163,951 A | 11/1992 | Pinchuk et al. |
| 5,163,952 A | 11/1992 | Froix |
| 5,163,958 A | 11/1992 | Pinchuk |
| 5,171,262 A | 12/1992 | MacGregor |
| 5,180,368 A | 1/1993 | Garrison |
| 5,183,085 A | 2/1993 | Timmermans |
| 5,192,297 A | 3/1993 | Hull |
| 5,192,307 A | 3/1993 | Wall |
| 5,192,311 A | 3/1993 | King et al. |
| 5,195,984 A | 3/1993 | Schatz |
| 5,197,978 A | 3/1993 | Hess |
| 5,207,644 A | 5/1993 | Strecker |
| 5,217,482 A | 6/1993 | Keith |
| 5,222,971 A | 6/1993 | Willard et al. |
| 5,226,913 A | 7/1993 | Pinchuk |
| 5,234,456 A | 8/1993 | Silvestrini |
| 5,242,394 A | 9/1993 | Tremulis |
| 5,242,399 A | 9/1993 | Lau et al. |
| 5,242,452 A | 9/1993 | Inoue |
| 5,254,084 A * | 10/1993 | Geary ............................ 604/29 |
| 5,256,146 A | 10/1993 | Ensminger et al. |
| 5,279,565 A | 1/1994 | Klein et al. |
| 5,282,823 A | 2/1994 | Schwartz et al. |
| 5,282,824 A | 2/1994 | Gianturco |
| 5,290,295 A | 3/1994 | Querals et al. |
| 5,290,305 A | 3/1994 | Inoue |
| 5,292,331 A | 3/1994 | Boneau |
| 5,304,120 A | 4/1994 | Crandell et al. |
| 5,304,200 A | 4/1994 | Spaulding |
| 5,306,250 A | 4/1994 | March et al. |
| 5,314,444 A | 5/1994 | Gianturco |
| 5,314,472 A | 5/1994 | Fontaine |
| 5,330,500 A | 7/1994 | Song |
| 5,336,178 A | 8/1994 | Kaplan et al. |
| 5,344,426 A | 9/1994 | Lau et al. |
| 5,354,279 A | 10/1994 | Hofling |
| 5,354,308 A | 10/1994 | Simon et al. |
| 5,356,433 A | 10/1994 | Rowland et al. |
| 5,360,401 A | 11/1994 | Turnland et al. |
| 5,368,566 A | 11/1994 | Crocker |

(56) References Cited

U.S. PATENT DOCUMENTS

| | | | |
|---|---|---|---|
| 5,372,600 | A | 12/1994 | Beyar et al. |
| 5,378,239 | A | 1/1995 | Termin et al. |
| 5,383,892 | A | 1/1995 | Cardon et al. |
| 5,405,378 | A | 4/1995 | Strecker |
| 5,415,637 | A | 5/1995 | Khosravi |
| 5,419,777 | A | 5/1995 | Hofling et al. |
| 5,421,955 | A | 6/1995 | Lau et al. |
| 5,423,745 | A | 6/1995 | Todd et al. |
| 5,423,885 | A | 6/1995 | Williams |
| 5,445,646 | A | 8/1995 | Euteneuer et al. |
| 5,449,373 | A | 9/1995 | Pinchasik et al. |
| 5,456,667 | A | 10/1995 | Ham et al. |
| 5,456,694 | A | 10/1995 | Marin et al. |
| 5,458,615 | A | 10/1995 | Klemm et al. |
| 5,476,476 | A | 12/1995 | Hillstead |
| 5,484,449 | A | 1/1996 | Amundson et al. |
| 5,507,768 | A | 4/1996 | Lau et al. |
| 5,514,154 | A | 5/1996 | Lau et al. |
| 5,545,132 | A | 8/1996 | Fagan et al. |
| 5,549,626 | A | 8/1996 | Miller et al. |
| 5,571,135 | A | 11/1996 | Fraser et al. |
| 5,603,721 | A | 2/1997 | Lau et al. |
| 5,609,574 | A | 3/1997 | Kaplan et al. |
| 5,611,775 | A | 3/1997 | Machold et al. |
| 5,626,604 | A | 5/1997 | Cottone, Jr. |
| 5,639,274 | A | 6/1997 | Fischell et al. |
| 5,653,690 | A | 8/1997 | Booth et al. |
| 5,653,691 | A | 8/1997 | Rupp et al. |
| 5,653,727 | A | 8/1997 | Wiktor |
| 5,693,029 | A | 12/1997 | Leonhardt |
| 5,713,860 | A * | 2/1998 | Kaplan et al. ............ 604/103.01 |
| 5,713,863 | A | 2/1998 | Vigil et al. |
| 5,716,396 | A | 2/1998 | Williams, Jr. |
| 5,720,726 | A | 2/1998 | Marcadis et al. |
| 5,733,303 | A | 3/1998 | Israel et al. |
| 5,733,325 | A | 3/1998 | Robinson et al. |
| 5,735,893 | A | 4/1998 | Lau et al. |
| 5,755,781 | A | 5/1998 | Jayaraman |
| 5,769,816 | A | 6/1998 | Barbut et al. |
| 5,782,855 | A | 7/1998 | Lau et al. |
| 5,800,521 | A | 9/1998 | Orth |
| 5,810,871 | A | 9/1998 | Tuckey et al. |
| 5,817,152 | A | 10/1998 | Birdsall et al. |
| 5,830,217 | A | 11/1998 | Ryan |
| 5,836,965 | A | 11/1998 | Jendersee et al. |
| 5,851,210 | A | 12/1998 | Torossian |
| 5,855,563 | A | 1/1999 | Kaplan et al. |
| 5,855,600 | A | 1/1999 | Alt |
| 5,873,852 | A | 2/1999 | Vigil et al. |
| 5,876,374 | A | 3/1999 | Alba et al. |
| 5,882,335 | A | 3/1999 | Leone et al. |
| 5,891,108 | A | 4/1999 | Leone et al. |
| 5,893,852 | A | 4/1999 | Morales |
| 5,902,332 | A | 5/1999 | Schatz |
| 5,904,670 | A | 5/1999 | Schreiner |
| 5,924,997 | A | 7/1999 | Campbell |
| 5,951,599 | A | 9/1999 | McCrory |
| 5,984,964 | A | 11/1999 | Roberts et al. |
| 5,997,468 | A | 12/1999 | Wolff et al. |
| 6,030,413 | A | 2/2000 | Lazarus |
| 6,066,168 | A | 5/2000 | Lau et al. |
| 6,102,904 | A | 8/2000 | Vigil et al. |
| 6,129,754 | A | 10/2000 | Kanesaka et al. |
| 6,146,358 | A | 11/2000 | Rowe |
| 6,190,405 | B1 | 2/2001 | Culombo et al. |
| 6,210,392 | B1 | 4/2001 | Vigil et al. |
| 6,245,026 | B1 | 6/2001 | Campbell et al. |
| 6,273,910 | B1 | 8/2001 | Limon |
| 6,273,913 | B1 | 8/2001 | Wright et al. |
| 6,280,413 | B1 | 8/2001 | Clark et al. |
| 6,280,414 | B1 | 8/2001 | Shah et al. |
| 6,283,947 | B1 | 9/2001 | Mirzaee |
| 6,287,336 | B1 | 9/2001 | Globerman et al. |
| 6,325,826 | B1 | 12/2001 | Vardi et al. |
| 6,334,871 | B1 | 1/2002 | Dor et al. |
| 6,358,247 | B1 | 3/2002 | Altman et al. |
| 6,402,778 | B2 | 6/2002 | Wang |
| 6,440,162 | B1 | 8/2002 | Cox et al. |
| 6,450,971 | B1 | 9/2002 | Andrus et al. |
| 6,451,044 | B1 | 9/2002 | Naghavi et al. |
| 6,482,178 | B1 | 11/2002 | Andrews et al. |
| 6,494,862 | B1 | 12/2002 | Ray et al. |
| 6,577,895 | B1 | 6/2003 | Altman |
| 6,592,569 | B2 | 7/2003 | Bigus et al. |
| 6,602,226 | B1 | 8/2003 | Smith et al. |
| 6,652,579 | B1 | 11/2003 | Cox et al. |
| 6,656,202 | B2 | 12/2003 | Papp et al. |
| 6,663,880 | B1 | 12/2003 | Roorda et al. |
| 6,685,648 | B2 | 2/2004 | Flaherty et al. |
| 6,695,813 | B1 | 2/2004 | Boyle et al. |
| 6,695,830 | B2 | 2/2004 | Vigil et al. |
| 6,733,474 | B2 | 5/2004 | Kusleika et al. |
| 6,905,476 | B2 | 6/2005 | Ponzi |
| 6,997,903 | B2 | 2/2006 | Wijay et al. |
| 7,097,440 | B2 | 8/2006 | Papp et al. |
| 7,217,255 | B2 | 5/2007 | Boyle et al. |
| 7,241,304 | B2 | 7/2007 | Boyle et al. |
| 2001/0000799 | A1 | 5/2001 | Wessman et al. |
| 2001/0007059 | A1 | 7/2001 | Mirzaee |
| 2001/0010014 | A1 | 7/2001 | Trozera |
| 2001/0012951 | A1 | 8/2001 | Bates et al. |
| 2001/0032011 | A1 | 10/2001 | Stanford |
| 2001/0047138 | A1 | 11/2001 | Kokate et al. |
| 2002/0009535 | A1 | 1/2002 | Michal et al. |
| 2002/0062147 | A1 | 5/2002 | Yang |
| 2002/0077564 | A1 | 6/2002 | Campbell et al. |
| 2002/0082515 | A1 | 6/2002 | Campbell et al. |
| 2002/0090388 | A1* | 7/2002 | Humes et al. ............ 424/422 |
| 2002/0091408 | A1 | 7/2002 | Sutton et al. |
| 2002/0091409 | A1 | 7/2002 | Sutton et al. |
| 2002/0091436 | A1 | 7/2002 | Phelps et al. |
| 2002/0095141 | A1 | 7/2002 | Belef et al. |
| 2002/0099406 | A1 | 7/2002 | St. Germain |
| 2002/0099407 | A1 | 7/2002 | Becker et al. |
| 2002/0103501 | A1 | 8/2002 | Diaz et al. |
| 2002/0107541 | A1 | 8/2002 | Vale et al. |
| 2002/0107561 | A1 | 8/2002 | Pinheiro |
| 2002/0111648 | A1 | 8/2002 | Kusleika et al. |
| 2002/0111659 | A1 | 8/2002 | Davis et al. |
| 2002/0115942 | A1 | 8/2002 | Stanford et al. |
| 2002/0120286 | A1 | 8/2002 | DoBrava et al. |
| 2002/0120287 | A1 | 8/2002 | Huter |
| 2002/0121472 | A1 | 9/2002 | Garner et al. |
| 2002/0123720 | A1 | 9/2002 | Kusleika et al. |
| 2002/0123755 | A1 | 9/2002 | Lowe et al. |
| 2002/0128679 | A1 | 9/2002 | Turovskiy et al. |
| 2002/0128680 | A1 | 9/2002 | Pavlovic |
| 2002/0128681 | A1 | 9/2002 | Broome et al. |
| 2002/0128706 | A1 | 9/2002 | Osypka |
| 2002/0133092 | A1 | 9/2002 | Oslund et al. |
| 2002/0138094 | A1 | 9/2002 | Borillo et al. |
| 2002/0138095 | A1 | 9/2002 | Mazzocchi et al. |
| 2002/0143360 | A1 | 10/2002 | Douk et al. |
| 2002/0143361 | A1 | 10/2002 | Douk et al. |
| 2002/0151927 | A1 | 10/2002 | Douk et al. |
| 2002/0151959 | A1 | 10/2002 | Von Oepen |
| 2002/0156456 | A1 | 10/2002 | Fisher |
| 2002/0156457 | A1 | 10/2002 | Fisher |
| 2002/0161390 | A1 | 10/2002 | Mouw |
| 2002/0161392 | A1 | 10/2002 | Dubrul |
| 2002/0161393 | A1 | 10/2002 | Demond et al. |
| 2002/0161395 | A1 | 10/2002 | Douk et al. |
| 2002/0165574 | A1 | 11/2002 | Ressemann et al. |
| 2002/0165576 | A1 | 11/2002 | Boyle et al. |
| 2002/0169414 | A1 | 11/2002 | Kletschka |
| 2002/0169458 | A1 | 11/2002 | Connors, III |
| 2002/0169472 | A1 | 11/2002 | Douk et al. |
| 2002/0169474 | A1 | 11/2002 | Kusleika |
| 2002/0173815 | A1 | 11/2002 | Hogendijk et al. |
| 2002/0173817 | A1 | 11/2002 | Kletschka et al. |
| 2002/0183763 | A1 | 12/2002 | Callol et al. |
| 2003/0105515 | A1 | 6/2003 | Skubitz et al. |
| 2003/0109824 | A1* | 6/2003 | Anderson et al. ............ 604/104 |
| 2003/0114921 | A1 | 6/2003 | Yoon |

(56) References Cited

U.S. PATENT DOCUMENTS

| | | | |
|---|---|---|---|
| 2003/0125802 A1 | 7/2003 | Callol et al. | |
| 2003/0181973 A1 | 9/2003 | Sahota | |
| 2004/0002650 A1 | 1/2004 | Mandrusov et al. | |
| 2004/0024445 A1 | 2/2004 | Dickson | |
| 2004/0044400 A1 | 3/2004 | Cheng et al. | |
| 2004/0059179 A1 | 3/2004 | Maguire et al. | |
| 2004/0064091 A1 | 4/2004 | Keren et al. | |
| 2004/0064099 A1 | 4/2004 | Chiu | |
| 2004/0086550 A1 | 5/2004 | Roorda et al. | |
| 2004/0093010 A1 | 5/2004 | Gesswein et al. | |
| 2004/0102831 A1 | 5/2004 | Murray, III | |
| 2004/0147939 A1 | 7/2004 | Rabkin et al. | |
| 2004/0162516 A1 | 8/2004 | Mandrusov et al. | |
| 2004/0214772 A1 | 10/2004 | Quay et al. | |
| 2004/0230156 A1 | 11/2004 | Schreck et al. | |
| 2004/0267353 A1 | 12/2004 | Gregorich | |
| 2005/0015048 A1* | 1/2005 | Chiu et al. | 604/101.04 |
| 2005/0058711 A1 | 3/2005 | Massengale et al. | |
| 2005/0070844 A1 | 3/2005 | Chow et al. | |
| 2005/0070991 A1 | 3/2005 | Pienknagura | |
| 2005/0090888 A1 | 4/2005 | Hines et al. | |
| 2005/0240141 A1 | 10/2005 | Aliski et al. | |
| 2005/0240147 A1* | 10/2005 | Makower et al. | 604/96.01 |
| 2005/0245882 A1 | 11/2005 | Elkins et al. | |
| 2005/0288632 A1 | 12/2005 | Willard | |
| 2006/0030814 A1 | 2/2006 | Valencia et al. | |
| 2006/0064009 A1 | 3/2006 | Webler et al. | |
| 2006/0079859 A1 | 4/2006 | Elkins et al. | |
| 2006/0106366 A1 | 5/2006 | Wang | |
| 2006/0189960 A1 | 8/2006 | Kesten et al. | |
| 2006/0224234 A1 | 10/2006 | Jayaraman | |
| 2006/0265043 A1 | 11/2006 | Mandrusov et al. | |
| 2007/0067009 A1 | 3/2007 | Gandhi et al. | |
| 2007/0129752 A1 | 6/2007 | Webler et al. | |
| 2007/0213671 A1 | 9/2007 | Hiatt | |
| 2007/0225634 A1 | 9/2007 | Ferren et al. | |
| 2007/0250035 A1 | 10/2007 | El-Nounou et al. | |
| 2007/0258903 A1 | 11/2007 | Kleiner et al. | |

FOREIGN PATENT DOCUMENTS

| | | |
|---|---|---|
| DE | 19605864 | 8/1996 |
| EP | 0062300 | 10/1982 |
| EP | 0221570 | 5/1987 |
| EP | 0338816 | 10/1989 |
| EP | 0361192 | 4/1990 |
| EP | 0364787 | 4/1990 |
| EP | 0372789 | 6/1990 |
| EP | 0380668 | 8/1990 |
| EP | 0407951 | 1/1991 |
| EP | 0408245 | 1/1991 |
| EP | 0421729 | 4/1991 |
| EP | 0423916 | 4/1991 |
| EP | 0428479 | 5/1991 |
| EP | 0517075 | 12/1992 |
| EP | 0540290 | 5/1993 |
| EP | 0541443 | 5/1993 |
| EP | 807424 | 11/1997 |
| EP | 1588731 | 10/2005 |
| FR | 2677872 | 12/1992 |
| GB | 2070490 | 9/1981 |
| GB | 2135585 | 11/1983 |
| JP | 58-501458 | 9/1983 |
| JP | 62-213762 | 9/1987 |
| JP | 62-231657 | 10/1987 |
| JP | 62-235496 | 10/1987 |
| JP | 63-214264 | 9/1988 |
| JP | 01083685 | 3/1989 |
| JP | 1299550 | 12/1989 |
| JP | 2-174859 | 7/1990 |
| JP | 2-255157 | 10/1990 |
| JP | 03009745 | 1/1991 |
| JP | 03009746 | 1/1991 |
| JP | 3-57465 | 3/1991 |
| JP | 3-151983 | 6/1991 |
| JP | 4-25755 | 2/1992 |
| JP | 63-246178 | 10/1998 |
| WO | WO-89/01798 | 3/1989 |
| WO | WO-89/08433 | 9/1989 |
| WO | WO-91/07139 | 5/1991 |
| WO | WO-92/06734 | 4/1992 |
| WO | WO-92/09246 | 6/1992 |
| WO | WO-9640325 | 12/1996 |
| WO | WO-9742998 | 11/1997 |
| WO | WO-99/66970 | 12/1999 |
| WO | WO-0067825 | 11/2000 |
| WO | WO-01/41861 | 6/2001 |
| WO | WO-01/82835 | 11/2001 |
| WO | WO-03/068306 | 8/2003 |

OTHER PUBLICATIONS

Abbott Cardiovascular Systems, Final Office Action mailed Jul. 30, 2014, U.S. Appl. No. 12/902,405.

Abbott Cardiovascular Systems, First Action Interview Pilot Program Pre-Interview Communication mailed Dec. 3, 2014, U.S. Appl. No. 13/154,258.

Abbott Cardiovascular Systems, Non-Final Office Action mailed Dec. 5, 2014, U.S. Appl. No. 12/902,405.

Non-Final Office Action mailed Jan. 13, 2015 for U.S. Appl. No. 13/446,768.

"70th Scientific Assembly and Annual Meeting: Scientific Program", Radiology, Special Edition, vol. 153(P), Washington, D.C., (Nov. 1984), 206.

"72nd Scientific Assembly and Annual Meeting: RSNA Scientific Program", Radiology, Special Edition, vol. 161(P), Chicago, IL, (Nov. 1986), 40.

"PE Plus Peripheral Balloon Dilation Catheter", C.R. Bard, Inc., USCI Division, (Aug. 1985).

Abbott Cardiovascular Systems, Final office action dated Jun. 30, 2009 for U.S. Appl. No. 10/802,435.

Abbott Cardiovascular Systems, Non final office action dated Dec. 3, 2009 for U.S. Appl. No. 10/802,435.

Abbott Cardiovascular Systems, International Preliminary Report on Patentability dated Dec. 10, 2009 for PCT/US2008/005947.

Abbott Cardiovascular Systems, Non final office action dated Feb. 24, 2010 for U.S. Appl. No. 11/756,376.

Abbott Cardiovascular Systems, Final office action dated Jun. 2, 2010 for U.S. Appl. No. 10/802,435.

Abbott Cardiovascular Systems, Final Office Action mailed Nov. 22, 2010 for U.S. Appl. No. 11/756,376.

Abbott Cardiovascular Systems, Non-final Office Action mailed May 24, 3011 for U.S. Appl. No. 11/756,376.

Abbott Cardiovascular Systems, Non final office action mailed Aug. 10, 2012 for U.S. Appl. No. 13/446,761.

Abbott Cardiovascular Systems, Final Office Action dated Mar. 28, 2013 for U.S. Appl. No. 13/446,761.

Abbott Cardiovascular Systems, "PCT Invitation to Pay Additional Fees and Partial Search Report mailed Aug. 27, 2008", PCT Application No. PCT/US2008/005947, 9 pages.

Abbott Cardiovascular Systems, "PCT Search Report and Written Opinion mailed Nov. 20, 2008", PCT Application No. PCT/US2008/005947, 26 pages.

Bonzel, T., et al., "The Sliding Rail System (Monorail): Description of a New Technique for Intravascular Instrumentation and Its Application to Coronary Angioplasty", Kardiologie, Supplemental 6, (1987), 119-122.

Charnsangavej, D., et al., "Endovascular Stent for Use in Aortic Dissection: An in Vitro Experiment", Radiology, vol. 157, No. 2, (Nov. 1985), 323-324.

Charnsangavej, Chusilp, et al., "Stenosis of the Vena Cava: Preliminary Assessment of Treatment with Expandable Metallic Stents", Radiology, vol. 161, (Nov. 1986), 295-298.

Cragg, et al., "Non-Surgical Placement of Arterial Endoprostheses: A New Technique Using Nitinol Wire", Radiology Journal, (Apr. 1983), 261-263.

(56) References Cited

OTHER PUBLICATIONS

Dotter, Charles T., "Transluminal Expandable Nitinol Coil Stent Grafting: Preliminary Report", Radiology Journal, (Apr. 1983), 259-260.
Dotter, Charles T., "Translumninally Placed Coilspring Endarterial Tube Grafts", Investigative Radiology, (Sep./Oct. 1969), 329-332.
Duprat, et al., "Flexible Balloon-Expanded Stent for Small Vessels", Radiology Journal, (1985), 73-77.
Finci, Leo, et al., "Percutaneous Transluminal Coronary Angioplasty of a Bifurcation Narrowing Using the Kissing Wire Monorail Balloon Technique", The American Journal of Cardiology, vol. 60, (Aug. 1987), 375-376.
Furui, Shigeru , et al., "Hepatic Inferior Vena Cava Obstruction: Treatment of Two Types with Gianturco Expandable Metallic Stents", Radiology, (Sep. 1990), 665-670.
Garasic, Joseph M., et al., "Stent and Artery Geometry Determine Intimal Thickening Independent of Arterial Injury", Circulation, vol. 101, (Feb. 2000), 812-818.
Harrington, J.D., et al., "The Palmaz-Schatz Stent", Handbook of Cardiovascular Interventions/Vascular Interventions, 563-572, Nov. 1996.
Kaltenbach, M., et al., "Zeitschrift fur Kardiologie", Abstracts, German Journal of Cardiology, Band 80, Supplementum 3, (Apr. 1991), 28-29.
Lawrence, David D., Jr. , et al., "Percutaneous Endovascular Graft: Experimental Evaluation", Radiology, vol. 163, (May 1987), 357-360.
Maass, et al., "Radiological Follow-Up of Transluminally Inserted Vascular Endoprosthese: An Experimental Study Using Expanding Spirals", Radiology Journal, (1984), 659-663.
Mirich, et al., "Percutaneously Placed Endovascular Grafts for Aoertic Aneurysms: Feasibility Study", Radiology, Part 2, (1989), 1033-1037.
Palmaz, et al., "Expandable Intraluminal Graft: A Preliminary Study", Raiodiology Journal, (1985), 73-77.
PCT Search Report, PCT/US2007/009418, (Oct. 4, 2007).
Rosch, Josef, et al., "Experimental Intrahepatic Portacaval Anastomosis: Use of Expandable Gianturco Stents", Radiology, vol. 162, (Feb. 1987), 481-485.
Rosch, Josef, et al., "Gianturco Expandable Stents in Experimental and Clinical Use", Twelfth Annual Course of Diagnostic Angiography and Interventional Radiology (Pittsburgh, PA), (Mar. 1987), 121-124.
Rosch, Josef, et al., "Gianturco Expandable Wire Stents in the Treatment of Superior Vena Cava Syndrome Recurring after Maximum-Tolerance Radiation", Cancer, vol. 60, (Sep. 1987), 1243-1246.
Rosch, Josef, et al., "Modified Gianturco Expandable Wire Stents in Experimental and Clinical Use", Annales de Radiologie, vol. 31, No. 2, (1988), 100-103.
Rosch, Jr., M.D. , et al., "Transjugular Intrahepatic Portacaval Shunt: An Experimental Work", The American Journal of Surgery, vol. 121, (May 1971), 588-592.
Strupp, G., et al., "Clinical and Angiographic Short and Medium Term Results after Coronary Stenting", Zeitschrift fur Kardiologie, vol. 81, (1992), 500-506.
Van Der Geissen, Willem J., et al., "Coronary Stenting with a new, Radiopaque Balloon-Expandable Endoprosthesis in Pigs", Circulation, vol. 83, No. 5, (May 1991), 93-149.
Wallace, Michael J., et al., "Tracheobronchia Tree: Expandable Metallic Stents Used in Experimental and Clinical Applications (Work in Progress)", Radiology, vol. 158, (Feb. 1986), 309-312.
Wright, et al., "Percutaneous Endovascular Stents: An Experimental Evaluation", Radiology Journal, (1985), 69-72.
Yoshioka, et al., "Development and Clinical Application of Biliary Endoprosthesis Using Expandable Metallic Stents", Japan Radiological Society, vol. 48, No. 9, (1988), 1183-1185.
Yoshioka, et al., "Self-Expanding Endovascular Graft: An Experimental Study in Dogs", American Journal of Roentgeriology, vol. 151, (Oct. 1988), 673-676.
Zeltinger, J., et al., "Advances in the Development of Coronary Stents", Biomaterials Forum, (2004), pp. 8-9, 24.

* cited by examiner

METHOD AND APPARATUS FOR IMPROVING DELIVERY OF AN AGENT TO A KIDNEY

BACKGROUND

Many diseases that affect organs develop over a decade or more. During this time, the function of the organ diminishes. The end-stage of many of these diseases is a transplant or some other treatment to supply artificially the organ's function—dialysis in the case of kidney disease such as end-stage renal disease, for example. A number of factors including immune system disorders or diabetes can cause these types of diseases.

Different diseases call for different treatments depending upon the dysfunction of the organ. For many of these diseases, the standard for treatment, short of a transplant, is drug-based. Drug-based treatments are usually systemic and typically use a pill or infusion of a solution of the drug in a carrier. These delivery methods are systemic because the patient's whole system is treated. But systemic treatment requires supplying the whole system drugs at levels high enough to be effective at the target organ. Achieving effective levels at the target organ frequently requires delivering toxic levels throughout the remainder of the system.

On the other hand, locally delivering the drug can alleviate some of the problems with systemic treatment. For instance, local delivery sidesteps supplying the drug system-wide allowing for effective local drug levels while maintaining much lower system-wide levels, levels that are frequently benign to the patient.

But local delivery presents its own set of challenges. Typically, with local delivery, the drug enters the bloodstream upstream of the desired treatment site. Another technique involves injecting the drug into a (temporarily) unperfused region of the vasculature near or in the diseased organ. This technique can use an occlusion device upstream of the deliver region to inhibit or stop blood flow. In either case, the natural laminar flow of blood does not always promote effective mixing between the drug and blood.

Ineffective mixing can prevent the drug from evenly reaching its target organ or region's cells. For example, delivery upstream of an arterial branch coupled with ineffective mixing can result in more drug being delivered down one branch than another.

What is needed is a delivery technique for local delivery that provides effective mixing between the blood and the drug. This need is especially acute for delivery to the kidney because the kidney contains a highly branched arterial vasculature.

SUMMARY

The present invention is directed towards a method of delivering drug or therapeutic agent containing solutions to an organ having branched vessels wherein the method uses at least one step that improves the uniformity of the delivery of the drug or therapeutic agent among the branched vessels.

The step can be any one or any combination of normalizing the viscosity of the therapeutic agent solution towards that of blood; delivering a delivery catheter with a delivery port that has a geometry that causes increased mixing between the blood and therapeutic agent solution; delivering a delivery catheter with at least one delivery port wherein the delivery fosters increased turbulence around the delivery port; decreasing the infusion rate of the therapeutic agent solution; or increasing the number of delivery ports.

In some embodiments of the present invention, a step that improves the uniformity of the delivery of the drug or therapeutic agent among the branched vessels is a step that causes the range of therapeutic agent concentrations delivered to the vessels to be small enough so that the total drug delivery to the vessel that receives the lowest concentration exceeds the minimum therapeutic dose, while the total drug delivery to the vessel that receives the highest concentration is 50-200; 75-175; or 90-150 percent of the maximum therapeutic dose.

In some embodiments of the present invention, a step that improves the uniformity of the delivery of the drug or therapeutic agent among the branched vessels is a step that causes the range of therapeutic agent concentrations delivered to the vessels to be small enough so that the total drug delivery to the vessel that receives the highest concentration falls within the maximum therapeutic dose, while the total drug delivery to the vessel that receives the lowest concentration is 100-300; 150-250; 175-225 percent of the minimum therapeutic dose.

In some embodiments of the present invention, a step that improves the uniformity of the delivery of the drug or therapeutic agent among the branched vessels is a step that causes the range of therapeutic agent concentrations delivered to the vessels to be small enough so that the average amount of drug delivered to each vessel falls within a range defined as a 85, 90, 95, 98, or 99 percent confidence interval calculated from the standard deviation of the average amount of drug delivered for the vessel with the highest such standard deviation.

DETAILED DESCRIPTION

The following description of several embodiments describes non-limiting examples that further illustrate the invention. All titles of sections contained herein, including those appearing above, are not to be construed as limitations on the invention, but rather they are provided to structure the illustrative description of the invention that is provided by the specification.

The features, aspects, and advantages of the invention will become more apparent from the following detailed description, appended claims, and accompanying drawings.

Unless defined otherwise, all technical and scientific terms used in this document have the same meanings as commonly understood by one skilled in the art to which the disclosed invention pertains. The singular forms a, an, and the include plural referents unless the context clearly indicates otherwise. Thus, for example, reference to "fluid" refers to one or more fluids, such as two or more fluids, three or more fluids, etc.

For purposes of this document, the portion of a delivery device designed to create turbulence in the blood flow is sometimes called a diffusion member or an expandable diffusion member.

Figure 1:
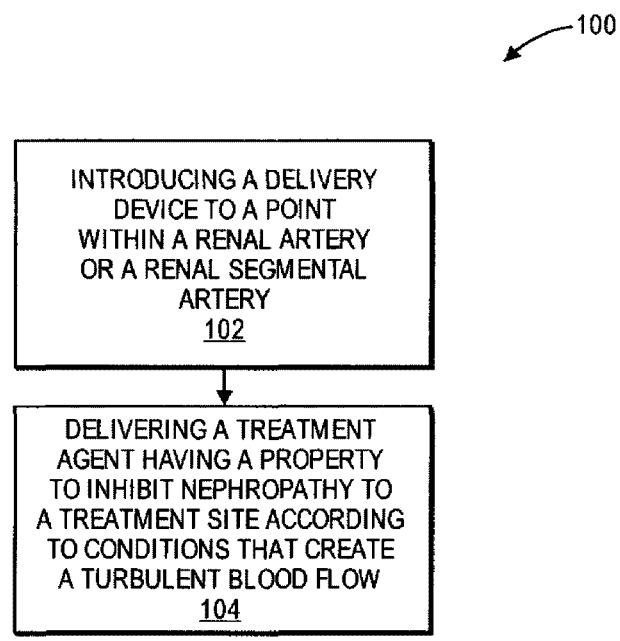
FIG. 1 illustrates a flow chart of a method for delivering a treatment agent to an organ or region.

FIG. 1 shows a flow chart of a method for delivering a treatment agent to a kidney. In one such embodiment, the method includes introducing a delivery device to a point within a renal artery or a renal segmental artery that supplies the renal cortex (block 102). Alternatively, the point may be within the renal cortex. The delivery device broadly includes any medical device for insertion into a physiological lumen to permit injection or withdrawal of fluids of varying viscosities, to maintain patency of a blood vessel lumen or an area defining the lumen, or for other purposes. The delivery device may further include any medical device capable of releasing a treatment agent after insertion into a physiological lumen. The point the delivery device is introduced at may be a treatment site or a region adjacent to a treatment site. The treatment site may be a diseased region within a renal vessel or other tissue of a kidney or other organ.

In one embodiment, the treatment agent is delivered according to conditions that create turbulent blood flow within a vessel region where the treatment agent is delivered (block 104). The term "turbulent blood flow" as used herein generally refers to a flow profile characterized by a chaotic or agitated blood flow or flow profile otherwise modified from a normal or steady state flow. Modified flow profiles may include rapid variations of pressure, flow direction or velocity. For example, in some embodiments, turbulent blood flow arises from partially occluding the vessel lumen by about 60% to about 90%.

Typically, the flow profile of blood flowing through the renal artery to the kidney is laminar, meaning the fluid flows in parallel layers, or streams, with little or no disruption between the layers. This profile continues along the kidney opening, or Ilium, and into the segmental arteries leading to the glomerular capillaries within the renal cortex. Thus, when the delivery device releases the treatment agent from a single point into one of these streams of a healthy kidney, most of the treatment agent is carried only to the kidney region at the end of the stream. In this respect, only a small portion of the kidney receives the treatment agent.

Moreover, the disease may reduce or stop altogether blood flow to those diseased regions especially in need of the treatment agent. In such cases, even when the treatment releases the treatment agent into a path normally destined for the diseased region, it may not reach that region. Treatment may overcome such problems by creating turbulence within the flow profile followed by treatment agent delivery into the turbulent blood flow. In particular, the turbulent conditions will facilitate mixing of the treatment agent with the blood and disrupt the streams typically found within the kidney causing more even distribution of the treatment agent throughout the kidney.

Liquid Flowing Streams

When blood or similar fluids experience flow parameters similar to those seen in a blood vessel, these fluids flow through a vessel lumen in substantially laminar flow—there is little mixing from point to point within the stream, if one looks at a cross-section of the lumen, the mixing between areas in one quadrant or stream and another quadrant or stream is very low. This means that introduction of a therapeutic-agent solution at a single point can result in a heterogeneous mix between the blood and solution. For instance, solution introduction at a lower rate will not substantially disturb the laminar flow behavior of the blood as it moves through the vessel lumen. Thus, downstream of the injection site, the blood is heterogeneous: some sectors contain blood mixed with more therapeutic-agent solution while others contain blood mixed with substantially less therapeutic-agent solution. Of course, one of ordinary skill in the art would expect that over time (distance traveled from the injection site), the blood from these various sectors would eventually mix yielding a substantially homogeneous blood-therapeutic-agent mixture.

This lack of mixing is inconsequential for systemic delivery. Systemic delivery of the injected therapeutic-agent solution provides longer times for the solution and blood to mix. But mixing must occur more quickly for local delivery. Local delivery methodologies frequently employ therapeutic-agent delivery within centimeters of the drug's target region. At typical blood flow rates, this short distance may yield mixing times of a few seconds or less.

It the goal is to uniformly treat a region, the blood and therapeutic-agent solution should mix before the treatment region receives the blood—therapeutic-agent mixture.

Blood from one quadrant or another will travel along one path or another in regions of high tortuosity. If the blood in one quadrant has not mixed with the therapeutic-agent solution, then pathways in the high tortuosity region that are fed by that blood quadrant will not see the same therapeutic-agent concentration as pathways that are fed from other sectors. This difference in therapeutic-agent concentration unavoidably leads to differences in treatment for tissues located along one pathway and those located along another pathway.

So, regional treatment may be better served by locating therapeutic-agent solution delivery points well ahead of the targeted region. But this is only a successful strategy if there is a sufficient vessel length ahead of the treatment region.

For instance, one may desire a longer vessel length within which to accomplish mixing between a therapeutic-agent solution and the blood. But another goal of regional delivery is for the therapeutic agent to substantially remain or arrive at the treatment region without substantial delivery to ancillary regions. There are instances when delivering far enough upstream of the target region to achieve adequate mixing of the therapeutic-agent solution and the blood would likewise require delivering the therapeutic-agent solution upstream of a vessel branch that would allow some of the therapeutic agent to follow the unintended branch rather than the intended one.

This circumstance, among others, leads to other strategies for promoting uniform regional drug delivery.

One class of strategies employs a turbulence-inducing element near the point at which the therapeutic-agent solution enters the vessel. In principle, having a turbulence-inducing member causes the non-mixing sectors discussed above in the laminar-blood-flow portion to mix. This mixing promotes adequate homogenization along a shorter path than if no turbulence-inducing elements were present.

Turbulence-inducing elements come in a variety of forms. Typically, the turbulence-inducing element functions by partially occluding the vessel or by forcing the blood to change directions as it flows by the element.

Another strategy for improving uniform regional drug delivery is to prepare the therapeutic-agent solution so that its viscosity more closely matches that of the blood, e.g. around 3-4 centipoise. Fluids flowing together through a vessel that have mismatched viscosities remain segregated for a longer time as they move through the vessel. The closer the viscosity match between the blood and therapeutic-agent solution, the easier or quicker the two mix.

Yet another strategy is to supply the therapeutic-agent solution at multiple positions near the distal end of a drug delivery device or catheter. This is believed to have at least two important effects: multiple injection positions promote turbulence in the blood flowing past the delivery device and multiple injection positions cause the therapeutic-agent solution to enter more individual streams or sectors within the blood flow.

Decreasing the speed of delivering the therapeutic-agent solution promotes more uniform therapeutic-agent delivery. Also, the geometry of the delivery port can be selected to encourage mixing. Such geometries can include structures with delivery ports that occupy a larger cross sectional area of the vessel, which allows for greater coverage of the fluid flow and improves mixing.

In one aspect, conditions creating turbulent blood flow may include partially occluding a region of the lumen so as to provide a constricted pathway for blood flow (e.g., about 60% to about 90% lumen occlusion). The narrowed pathway causes the speed of the blood flowing through that region to increase resulting in turbulent blood flow. The treatment agent may then be injected into that region. In other embodiments, the conditions creating a turbulent blood flow may include injecting a treatment agent within a vessel lumen in a direction perpendicular to the direction of blood flow. In this aspect, the stream of treatment agent alters the normal direction of blood flow, disturbing the normal flow path, and causing turbulence. This turbulence mixes the treatment agent with the blood for delivery to the treatment site. In addition, this turbulence may disrupt the downstream laminar flow profiles within the kidney. The homogenous distribution of the treatment agent throughout the blood flowing to the kidney and disruption of flow profiles within the kidney facilitates a substantially uniform distribution of the treatment agent solution throughout the kidney tissues or the tissues of other organs.

Representatively, a femoral artery may be punctured and delivery device 224 may be advanced through the femoral artery, to aorta 200, and then into renal artery 202. Alternatively, one may advance the delivery device 224 through a brachial artery, down aorta 200, and into renal artery 202. In still further embodiments, an external iliac artery may be punctured and delivery device 224 may be advanced through the external iliac artery to a common iliac artery, to aorta 200, and then into renal artery 202.

It is further contemplated that delivery device 224 may be introduced to a point within kidney 204 using retroperitoneal insertion. In this aspect, a distal end of delivery device 224 may be inserted through the back of the patient adjacent kidney 204. Delivery device 224 may then be advanced through a surface of kidney 204 to a point within renal cortex 218 adjacent to glomerulus 216. In this aspect, when the treatment agent is delivered with delivery device 224, it localizes within an area proximal to glomerular capillaries within the kidney. Alternatively, delivery device 224 may be introduced through a back region of the patient and into renal artery 202. In this embodiment, the treatment agent may then be delivered by delivery device 224 through renal artery 202 to a desired treatment site.

Figure 2:
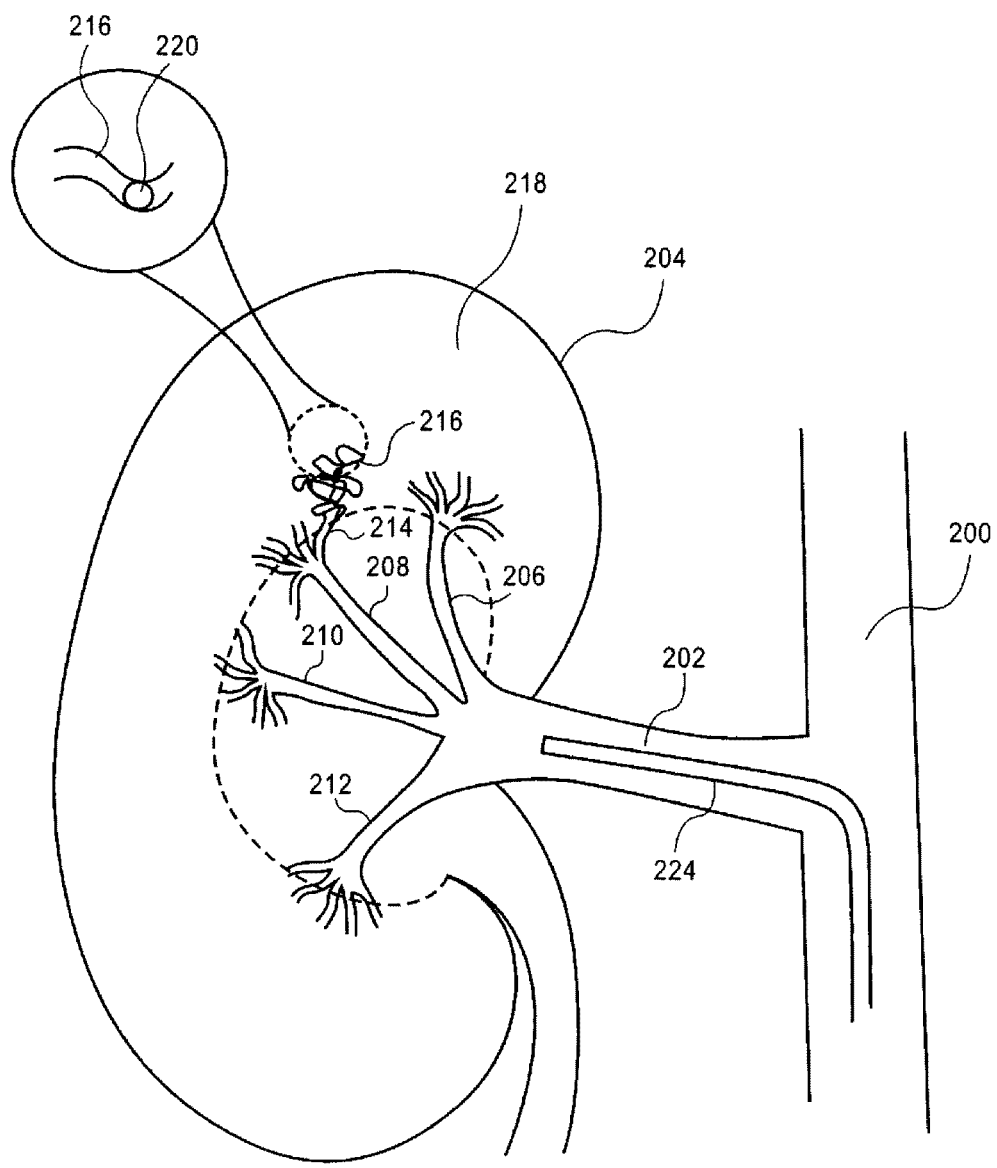
FIG. 2 shows a cross-sectional side view of a kidney and a device for delivering a treatment agent to the kidney.

In an embodiment illustrated in FIG. 2, a treatment agent loaded within delivery device 224 may be released into, for example, renal artery 202 such that the treatment agent flows through segmental artery 208 and into glomerulus 216. In one embodiment, the treatment agent may be loaded into a carrier (such as a particle) having a large enough diameter such that the carrier lodges within a narrow lumen of a capillary within the glomerulus 216. The FIG. 2, exploded-view of glomerulus 216 shows this aspect. In this embodiment, treatment agent 220 flows into glomerulus 216 and lodges within the lumen. For example, in some embodiments the treatment agent may have a diameter from about 8 microns to about 15 microns. Thus, release of the treatment agent from within the carrier localizes it at glomerulus 216, and the treatment agent remains at a specific treatment site within the kidney.

Useful treatment agents will be discussed below after discussing several embodiments of delivery devices according to embodiments of the invention.

Figure 3:
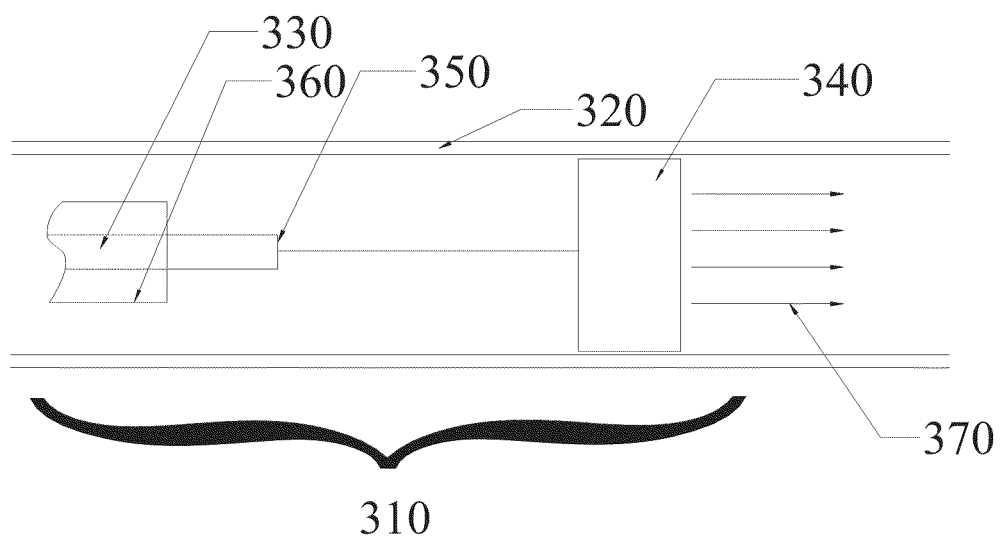
FIG. 3 is a schematic view of a catheter and an expandable diffusion member.

Referring to FIG. 3, the device 310 sits within the lumen of vessel 320 before delivering the drug. As shown in FIG. 3, the device 310 has a catheter portion 330 connected to an expandable diffusion member 340. The catheter portion 330 contains a diffusion member delivery lumen 350 and a drug delivery lumen 360. In the figure, the drug delivery lumen 360 is shown coaxial with the diffusion member delivery lumen 350. But this need not be the case for any embodiments described in this document. For each of the embodiments in this document described as having a diffusion member delivery lumen 350 coaxial with the drug delivery lumen 360, a corresponding embodiment exists in which these lumens are not coaxial.

In operation, the device 310 is placed into a desired vessel 320 upstream of the desired treatment region or organ. The expandable diffusion member 340 is deployed creating a region of increased turbulence in the blood flow near the expandable diffusion member 340. Upstream of the expandable diffusion member 340 within the region of increased blood turbulence or upstream of that region, the therapeutic agent can be released from drug delivery lumen 360.

When the drug reaches the turbulent region, it mixes more thoroughly with the blood than it would have if the expandable diffusion member 340 were not present. Past the turbulent region, the blood and drug mixture returns to laminar flow 370. In some embodiments, the expandable diffusion member 340 creates a turbulent region that ranges from upstream of the diffusion member 340 to downstream of the member. After drug delivery, the expandable diffusion member 340 is retrieved.

Figure 4:
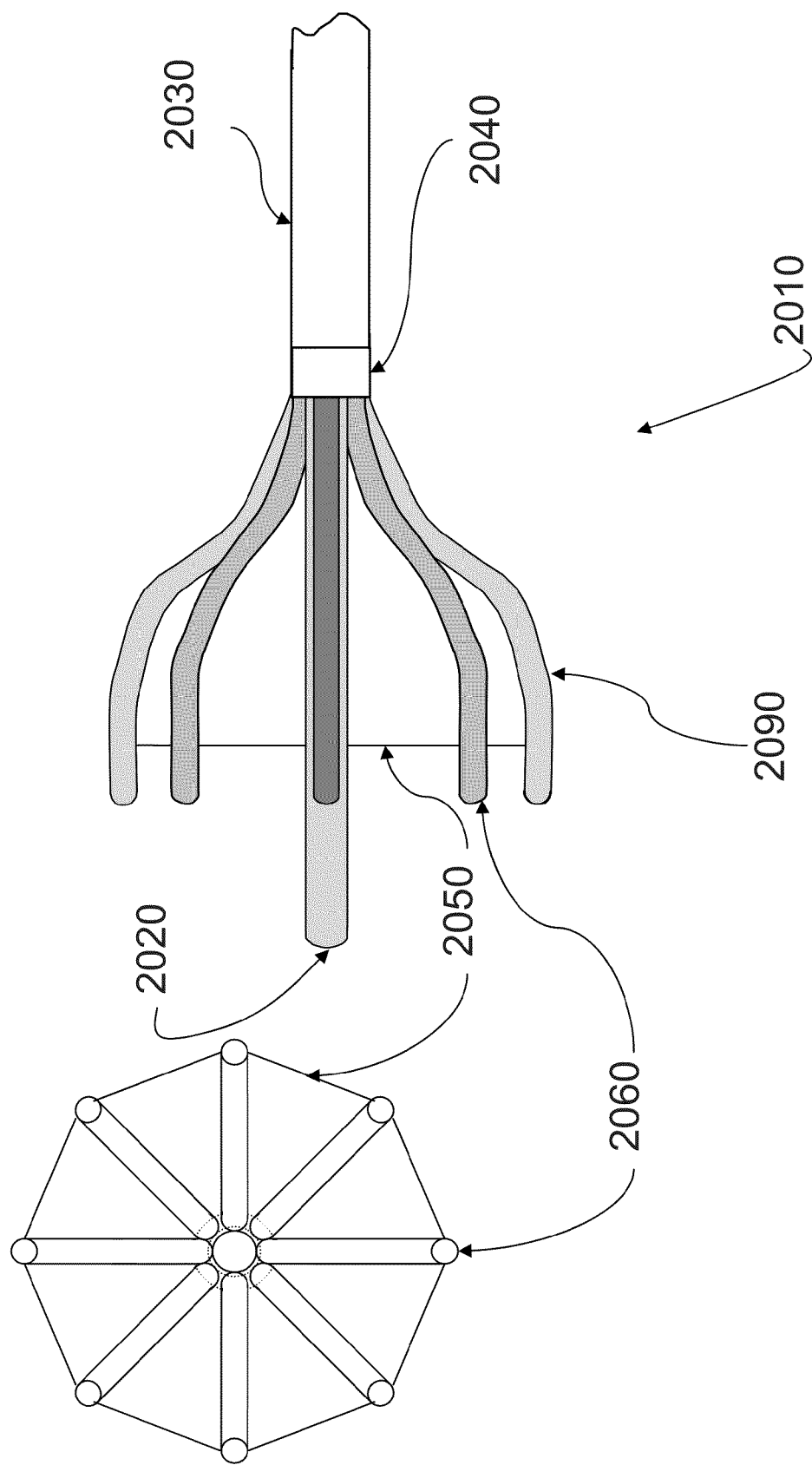
FIG. 4 is a schematic side and end view of an umbrella-like embodiment of a therapeutic agent delivery device.

FIG. 4 shows an embodiment of the therapeutic agent delivery device 2010 of the invention. It comprises, at the distal end, a floppy, guide-wire-like tip 2020. Further back from the guide-wire-like tip 2020 and coaxial to the delivery device's 2010 main wire 2030 sits a self-expanding structure 2090. The self-expanding structure 2090 and struts 2060 connect to a shaft (not shown) by a ring (not shown). In some embodiments, the struts 2060 are constructed from the same material as the ring. In some embodiments, the struts 2060 are integral to the ring.

Further back from the self-expanding structure 2090 and also coaxial to the main wire 2030 is a mounting ring 2040 that attaches to the main wire 2030.

Figure 5:
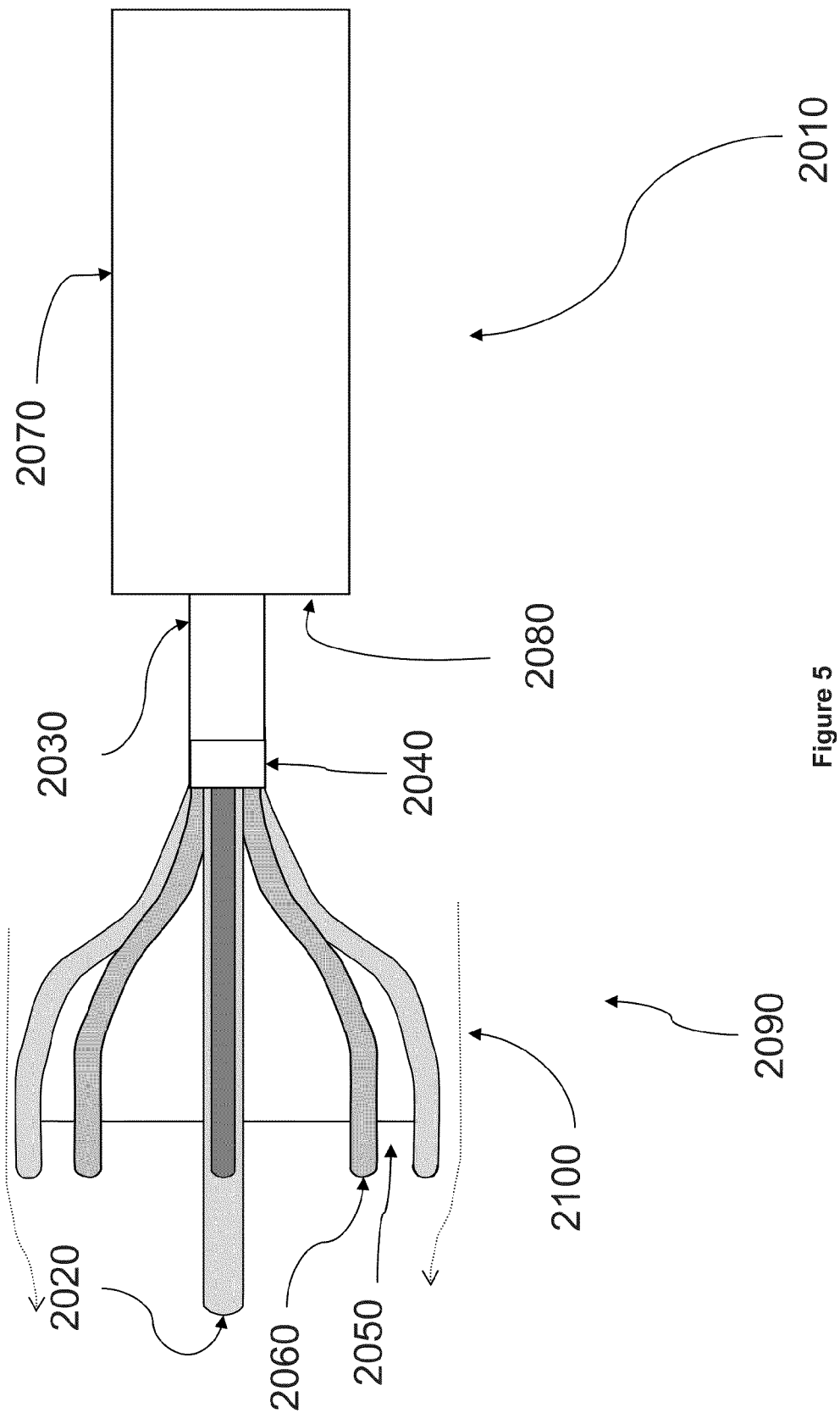
FIG. 5 is a schematic side view of a therapeutic agent delivery device of FIG. 4 situated in the delivery catheter.

As depicted in FIG. 5, the main wire 2030 is situated within an outer sheath 2070. Between the main wire 2030 and outer sheath 2070 is a passageway 2080 with which to infuse drug solutions or other therapeutic agents. The blood flow around the self-expanding structure 2090 is indicated as 2100.

In some embodiments, the self-expanding structure 2090 is composed of struts 2060 and a flexible membrane 2050. In these or other embodiments, the flexible membrane 2050 is composed of polyurethane, nylon, or pebax. It can take a number of different forms. In some embodiments, the flexible membrane 2050 becomes taut when deployed; in other embodiments, the flexible membrane 2050 remains at least somewhat slack when deployed. Similarly, the attachment of flexible membrane 2050 to the strut 2060 can also take a number of different forms. In some embodiments, the flexible membrane 2050 is attached or bonded to strut 2060 within the entire contact region between the flexible membrane 2050 and the strut 2060. In other embodiments, the flexible membrane 2050 is attached or bonded to strut 2060 at the distal end of strut 2060. The struts 2060 are composed of a flexible or elastic material such as nitinol, a polymer, or polymer-coated stainless steel.

Figure 6:
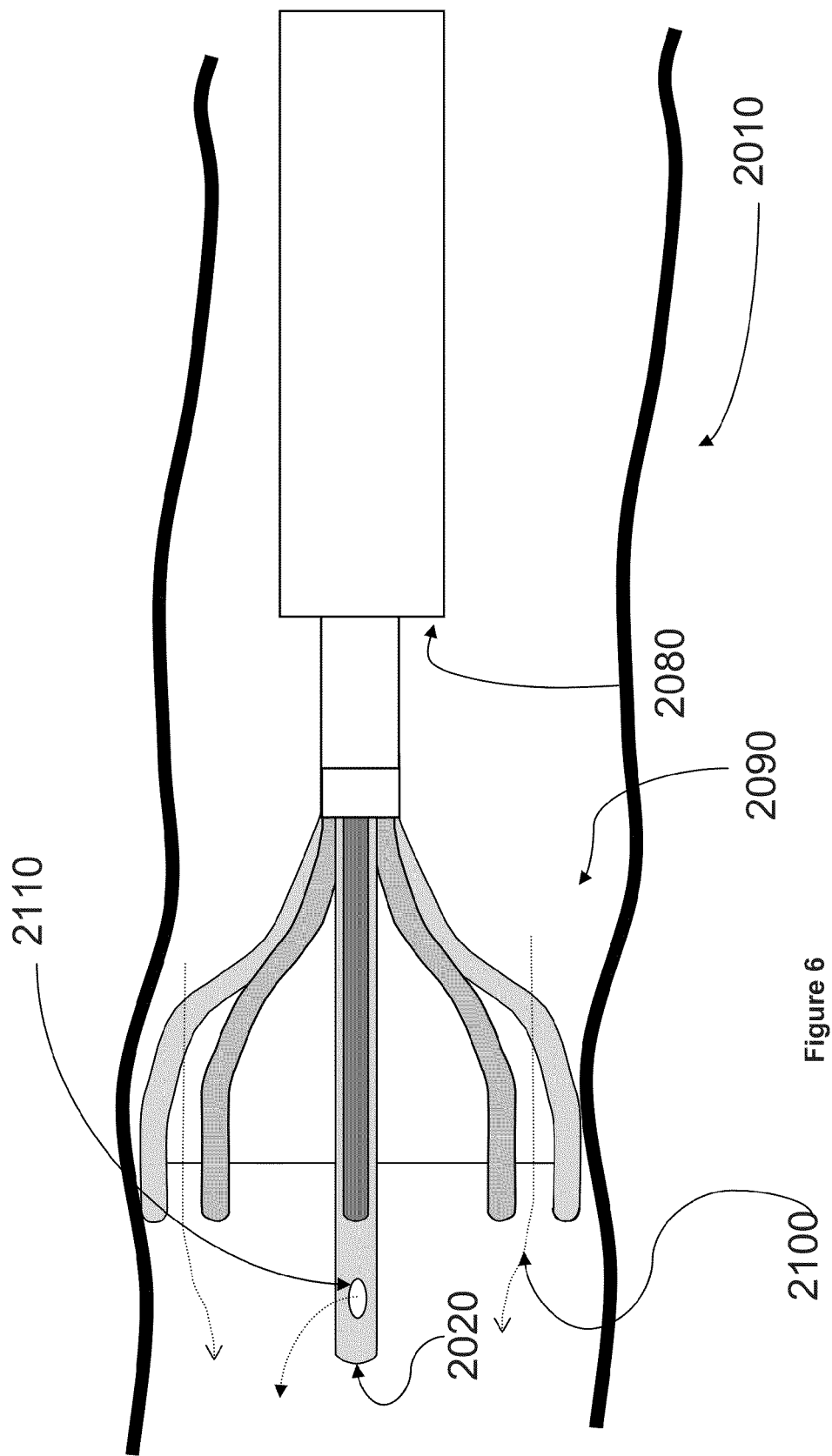
FIG. 6 is a schematic side view of the therapeutic agent delivery device of FIG. 5 situated within the vessel lumen of a mammal.

In some embodiments, such as shown in FIG. 6, the floppy, guide-wire-like tip 2020 also contains a distal infusion port 2110. Some embodiments have both a passageway 2080 and a distal infusion port 2110 for supplying a drug or other therapeutic agent.

Figure 7:
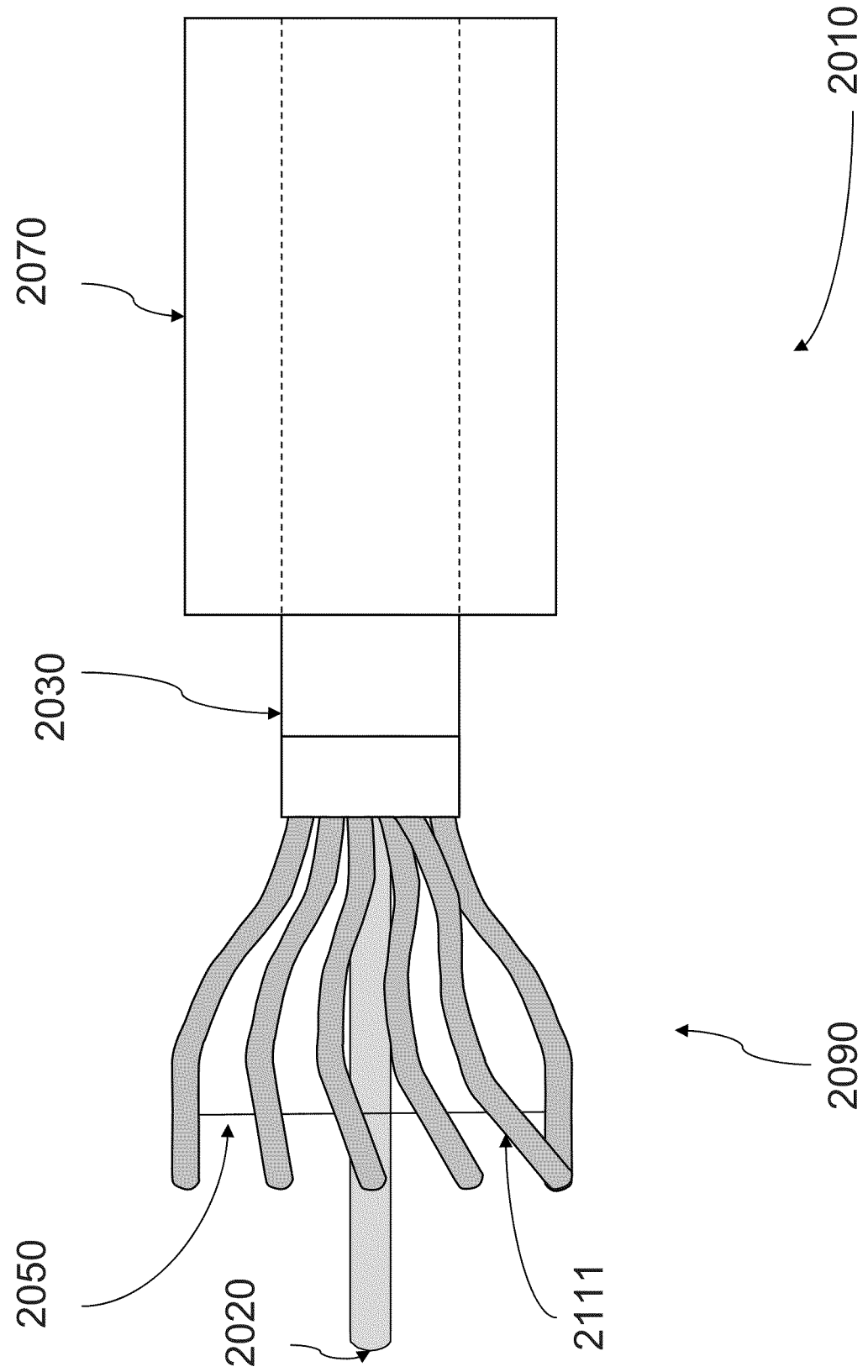
FIG. 7 is a schematic side view of the therapeutic agent delivery device of an embodiment of the invention that has serpentine struts.

In some embodiments, the struts 2060 are serpentine such as shown in FIG. 7—serpentine struts 2111.

In operation, the therapeutic agent delivery device 2010, as shown in FIG. 4, is inserted into the patient percutaneously and then threaded through the patient's vasculature until the device resides near or upstream of the desired treatment region. Threading the device 2010 through the tortuous vasculature uses a guide-wire-like tip 2020 to pass through or to cross the curves of the vasculature. Once positioned, delivery of the therapeutic agent requires the deployment of the self-expanding structure 2090. Typically, deployment employs retraction or other manipulation of the outer sheath 2070, which has been constraining the self-expanding structure 2090, such that the manipulation frees the self-expanding structure 2090.

Without wishing to be bound by any particular theory, the deployed self-expanding structure 2090 is believed to disturb the local blood flow causing a turbulent region near the therapeutic agent delivery device 2010.

After the deployment of the self-expanding structure 2090, drugs or other therapeutic agents are delivered through the passageway 2080. This constitutes delivery of the therapeutic agent or drug upstream of the turbulent blood, region. In an alternative embodiment, such as shown in FIG. 6, drugs or therapeutic agents are delivered from distal infusion port 2110 located distal to the self-expanding number 2090. This results in drug delivery downstream of the turbulent blood region.

Figure 8:
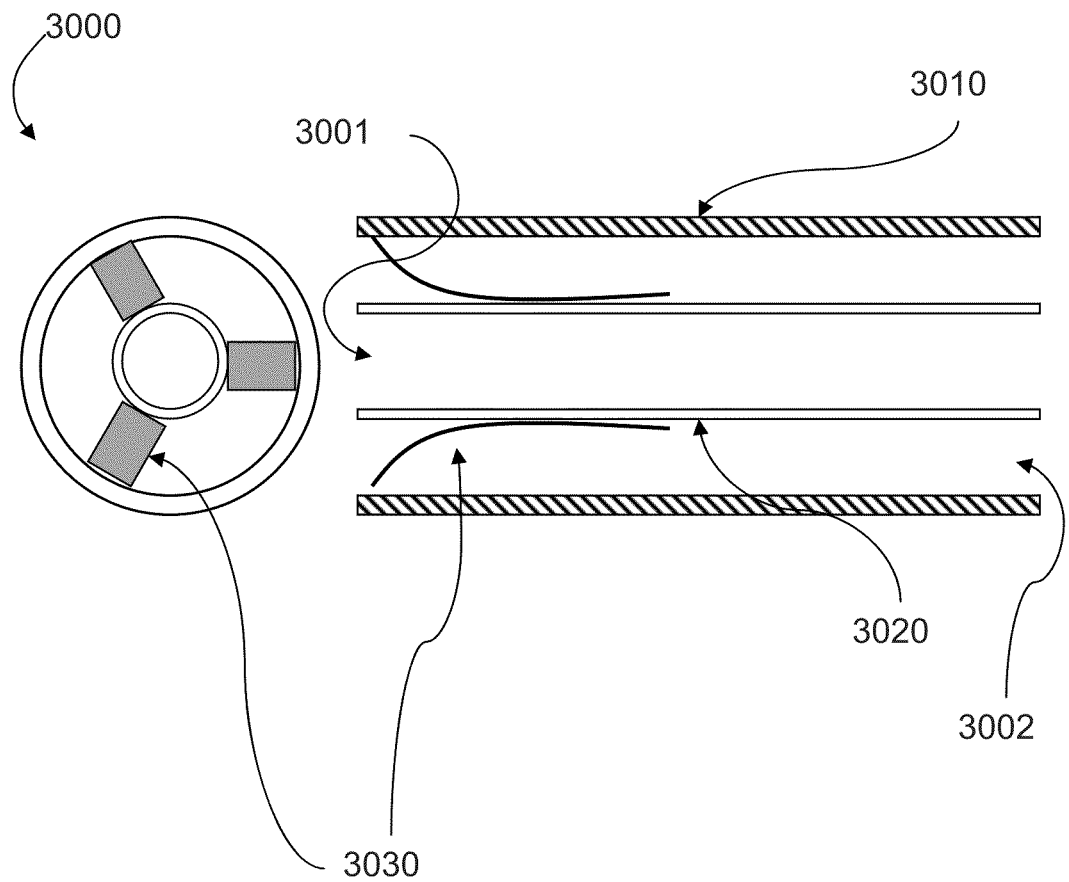
FIG. 8 is a side view and end schematic view of an embodiment of a therapeutic agent delivery device showing retracted coils.

Another embodiment of the invention is also directed at a device adapted for percutaneous delivery into the vasculature of a mammal and adapted to expand the expandable diffusion member within the vessel of the mammal. This class of embodiments includes an infusion catheter for delivering drugs or other therapeutic agents to the mammal's vasculature. In some embodiments, the therapeutic agents are diabetic nephropathy treatment agents. In FIG. 8, the device 3000 includes at least one, standard, single-lumen infusion port 3001 located at or near the distal end of an infusion catheter 3002.

Figure 9:
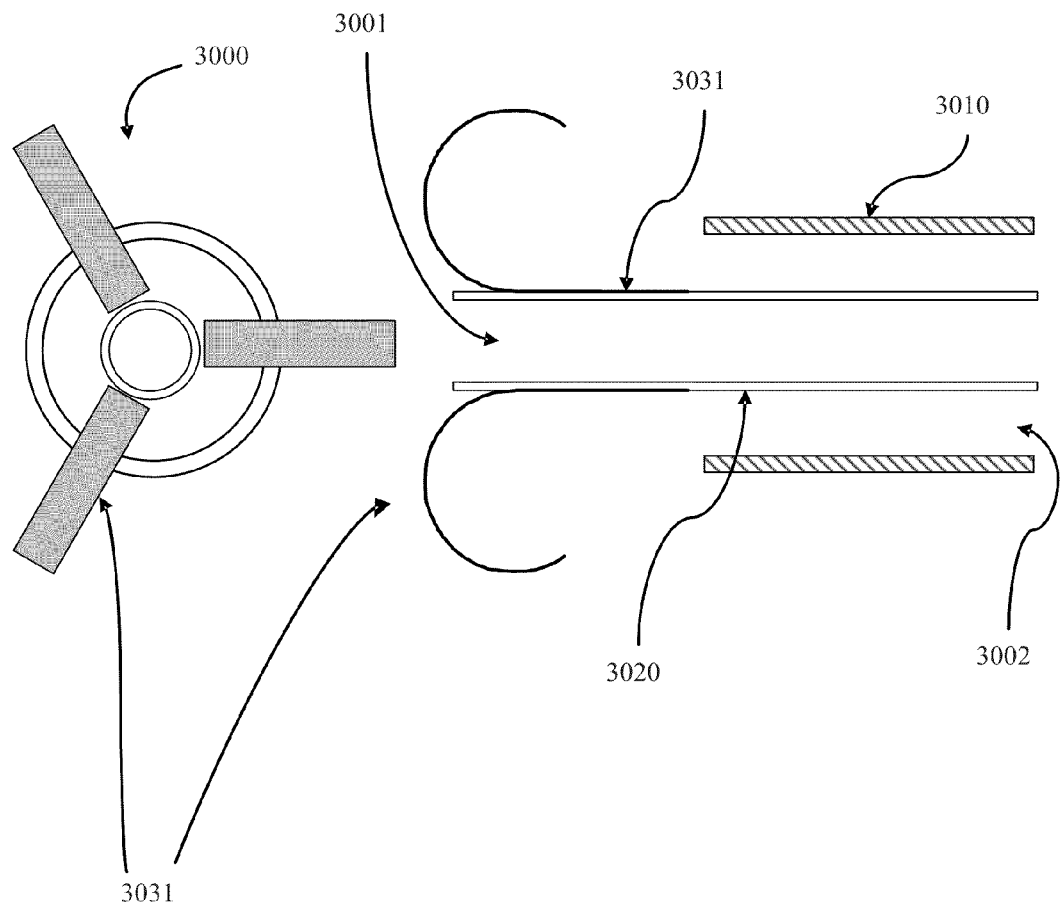
FIG. 9 shows an expanded-coil-view of the therapeutic agent delivery device of FIG. 8.

Coils 3030 connect to the outside of the infusion catheter's walls 3020 near the distal end of the infusion catheter 3002. The coils 3030 have a substantially rectangular shape and are cut from nitinol foil or sheets, but those of ordinary skill in the art will recognize that these coils 3030 can take just about any shape. The coils 3030 are shown collapsed in FIG. 8 and coils 3031 are shown as deployed in FIG. 9. In addition to nitinol, the coils 3030 can be formed of any material capable of springing open or self-expanding from a retracted position to an expanded or deployed position.

The device 3000 also comprises a sheath 3010 that is movably affixed to the distal end of the device 3000, but is manipulable from a control handle (not shown) connected to the proximal end of the device 3000. When in the closed position, the sheath 3010 maintains the coils 3030 in a collapsed configuration. When in the open position, the sheath 3010 no longer interferes with the coils 3030, and they assume the shape shown in FIG. 9 in their deployed position 3031. In addition to providing a turbulence-inducing member, the coils 3030 also serve to center the catheter within the vessel lumen. The coils 3030 allow for adjustments for varied turbulence inducing effect or for varied radial force, as desired. (Varying the radial force varies the force with which each coil 3030 presses against the artery or vein.)

Figure 10:
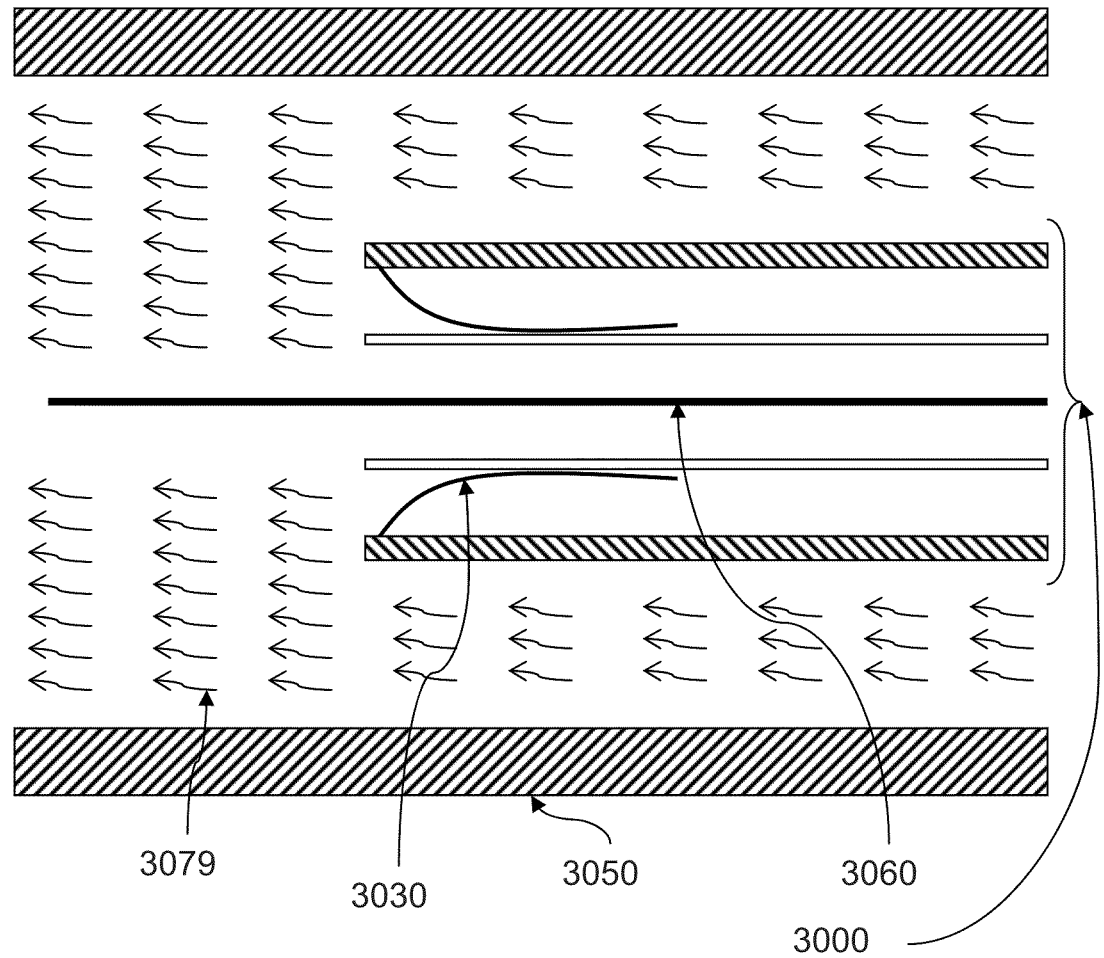
FIG. 10 illustrates a representation of uniform blood flow through a vessel lumen and around the therapeutic agent delivery device of FIG. 8.

FIG. 10 depicts the device 3000 in cross-section situated around guide wire 3060 and within vessel 3050 with coils 3030 in their retracted position. The arrows identified as 3079 indicate the blood flow within the vessel 3050 and the uniformity of the arrows represents substantially laminar flow.

Figure 11:
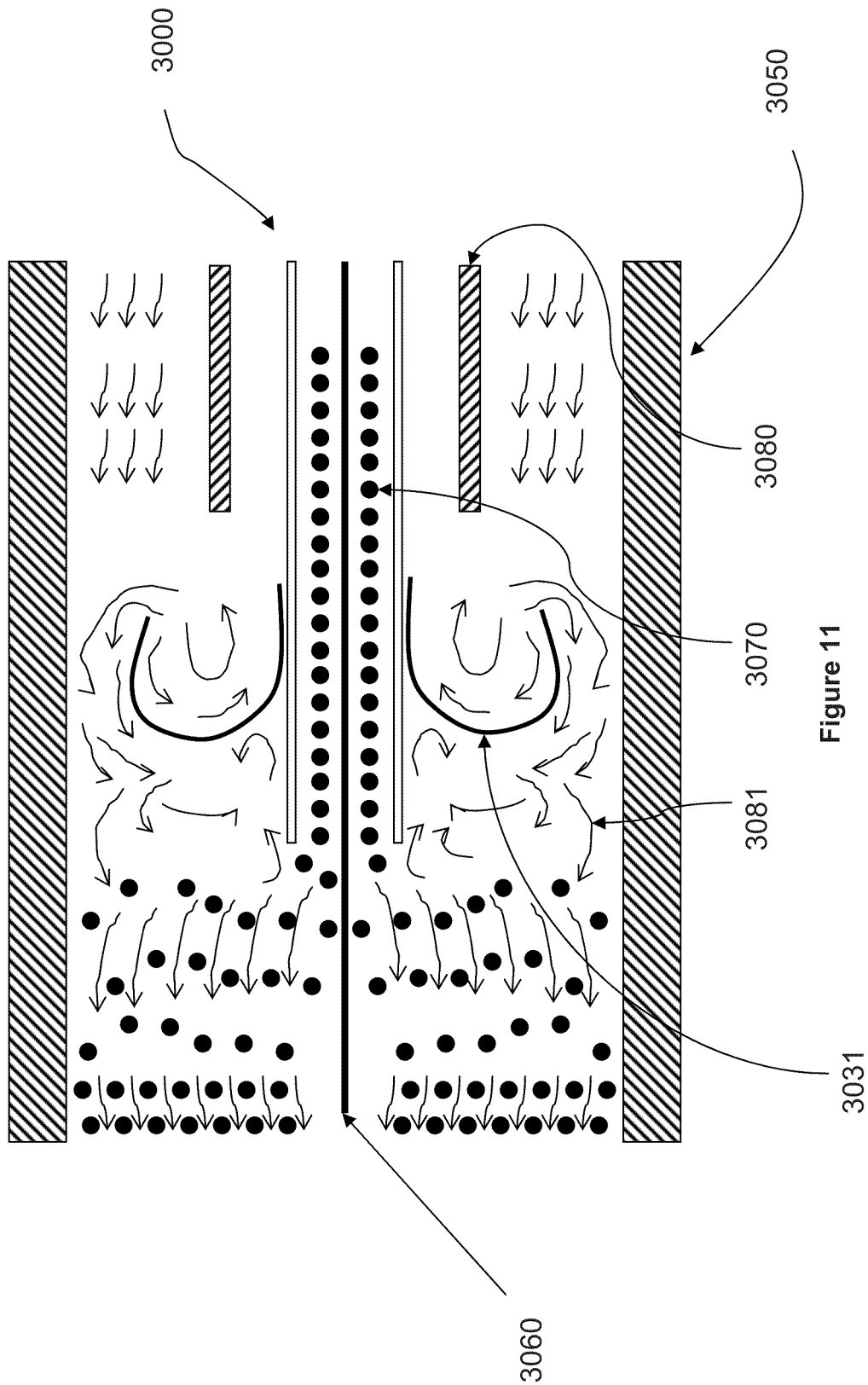
FIG. 11 illustrates a representation of locally turbulent blood flow around the expanded-coil-arrangement of the therapeutic agent delivery device of FIG. 8.

FIG. 11 depicts the device 3000 in cross-section situated around guide wire 3060 and within vessel 3050 with coils 3031 in their deployed position. The arrows identified as 3081 indicate the blood flow within the vessel 3050 and the chaos of the arrows represents turbulent flow. The outer sheath 3080 is shown in its retracted position. Drug particles 3070 are shown emerging from the device 3000 into the turbulent flow, which causes mixing between the drug particles 3070 and the blood.

Figure 12:
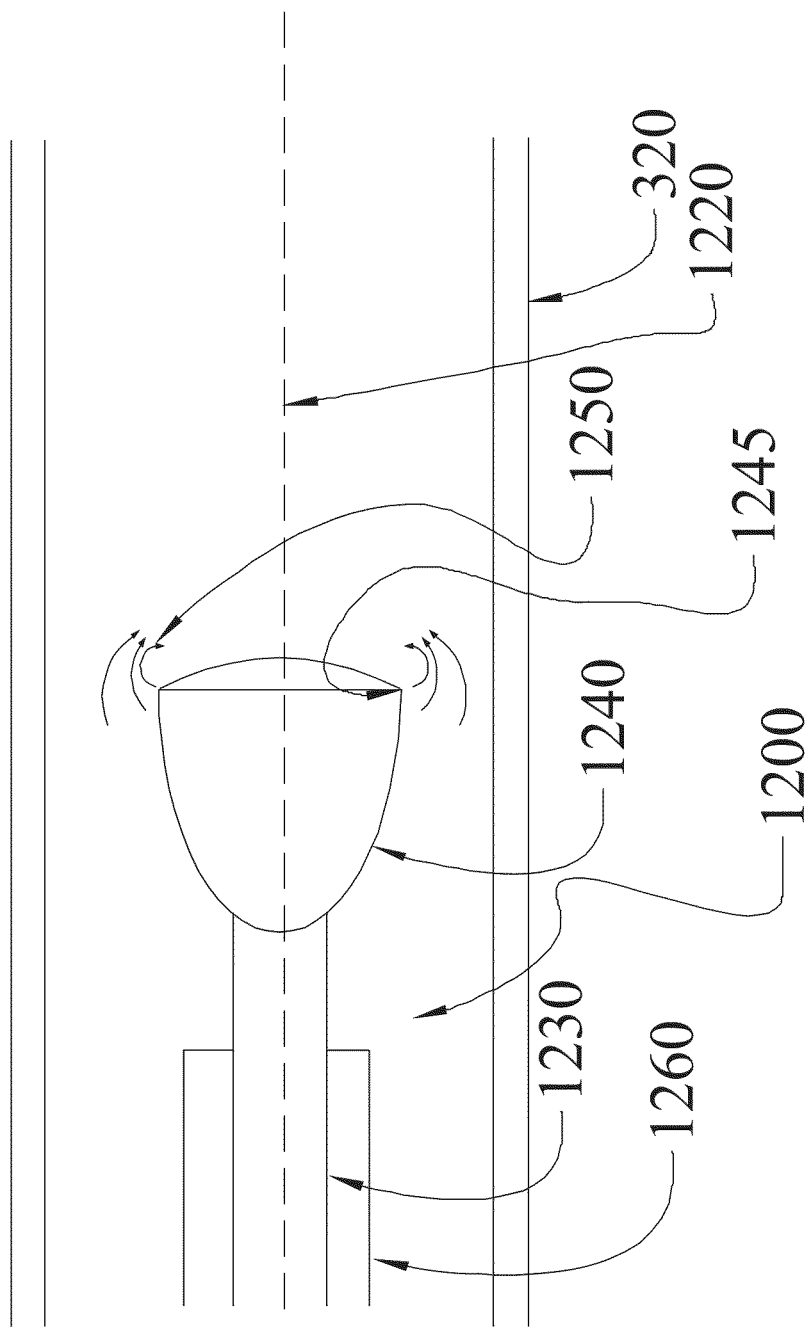
FIG. 12 illustrates a delivery catheter that includes an elongate portion.

As shown in FIG. 12, a delivery catheter 1200 includes an elongate portion adapted, in some embodiments, for percutaneous delivery. The delivery catheter 1200 also includes a catheter portion 1260 coaxial with the drug delivery lumen 1230 through which a drug or pharmaceutical may be delivered to the vessel lumen 320. A guidewire 1220 sits within the delivery catheter 1200, to aid in moving the delivery catheter 1200 to a desired delivery region. To aid its mixing, the drug exits through diffusion member 1240. Diffusion member 1240 causes the blood to divert creating turbulent blood flow 1250 as the blood transitions across the edge 1245 of diffusion member 1240. Diffusion member 1240 can be made from a flexible polymer (Pebax, nylon etc) in order to be expanded and refolded within the catheter sheath. One possible method of diffusion member expansion can be that the drug solution, soluble or microparticles, delivered through drug delivery lumen 1230 inflates diffusion member 1240 by internal pressure. After drug delivery, diffusion member 1240 can be retracted and refolded back into 1260. In an alternative method, nitinol struts as in 2060 can be internal to the diffusion member and can actively expand the element after catheter sheath 1260 is retracted.

Figure 13:
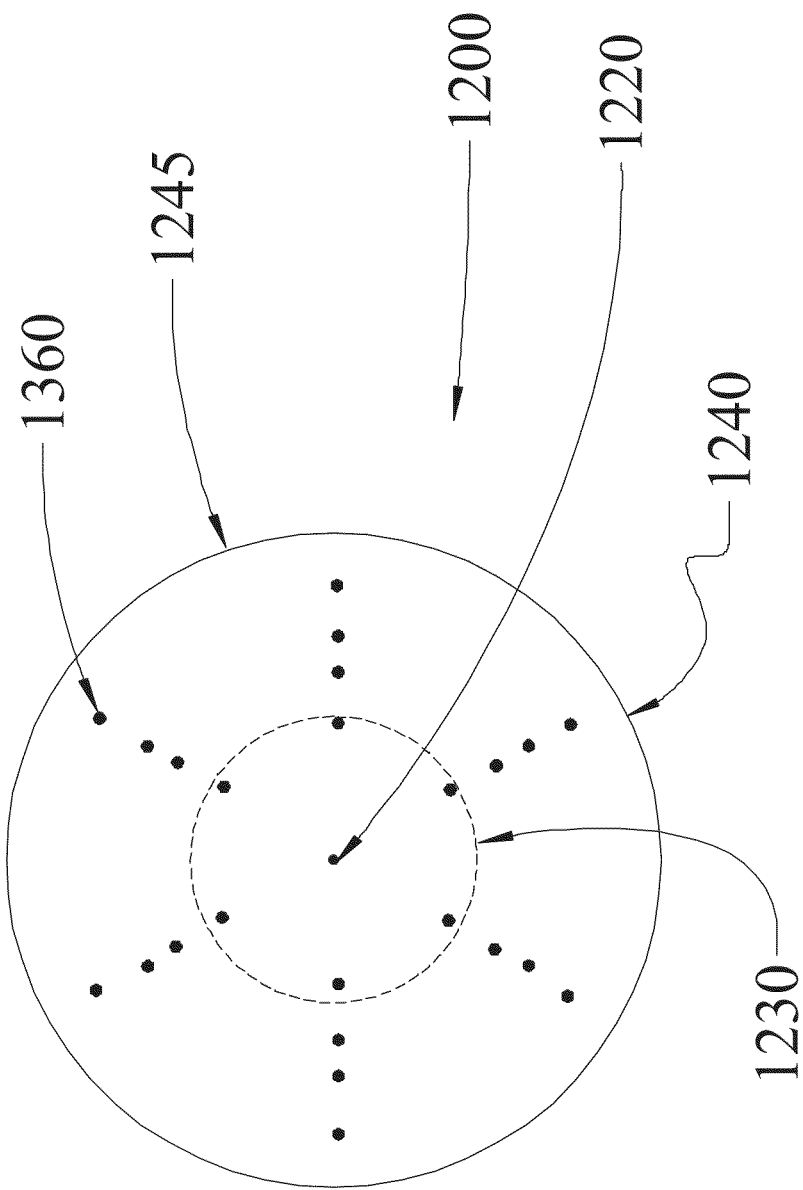
FIG. 13 illustrates the distal end of delivery catheter of FIG. 12.

FIG. 13 shows an alternate view of the delivery catheter 1200 looking at the distal end of the delivery catheter 1200. As can be seen, the guidewire 1220 is centered in the delivery catheter 1200. Diffusion member 1200 predominates in this view. The edge 1245 of diffusion member 1240 appears as a circle in this view. In this embodiment, the multiple delivery ports 1360 are shown located symmetrically on the end of diffusion member 1240, although any arrangement would suit the invention.

In operation, the delivery catheter 1200 is delivered percutaneously (in some embodiments) to blood vessel 320 over guidewire 1220. After delivery, appropriate tension on guidewire 1220 causes diffusion member 1240 to adopt its operational or unfolded position. Once placed into its operational position, drugs or pharmaceuticals travel down drug delivery lumen 1230 through the diffusion member 1240 and then out through delivery port 1360 for delivery.

The edge 1245 of the diffusion member 1240 interferes with blood flow and creates a region of turbulent blood flow 1250 that at least partially extends across the end of diffusion member 1240 moving through the space where delivery ports 1360 deposit the drug or pharmaceutical composition at delivery. The confluence of the turbulent blood flow 1250 and the released drug or pharmaceutical compound promotes quicker mixing between the blood and the drug or pharmaceutical.

Figure 14:
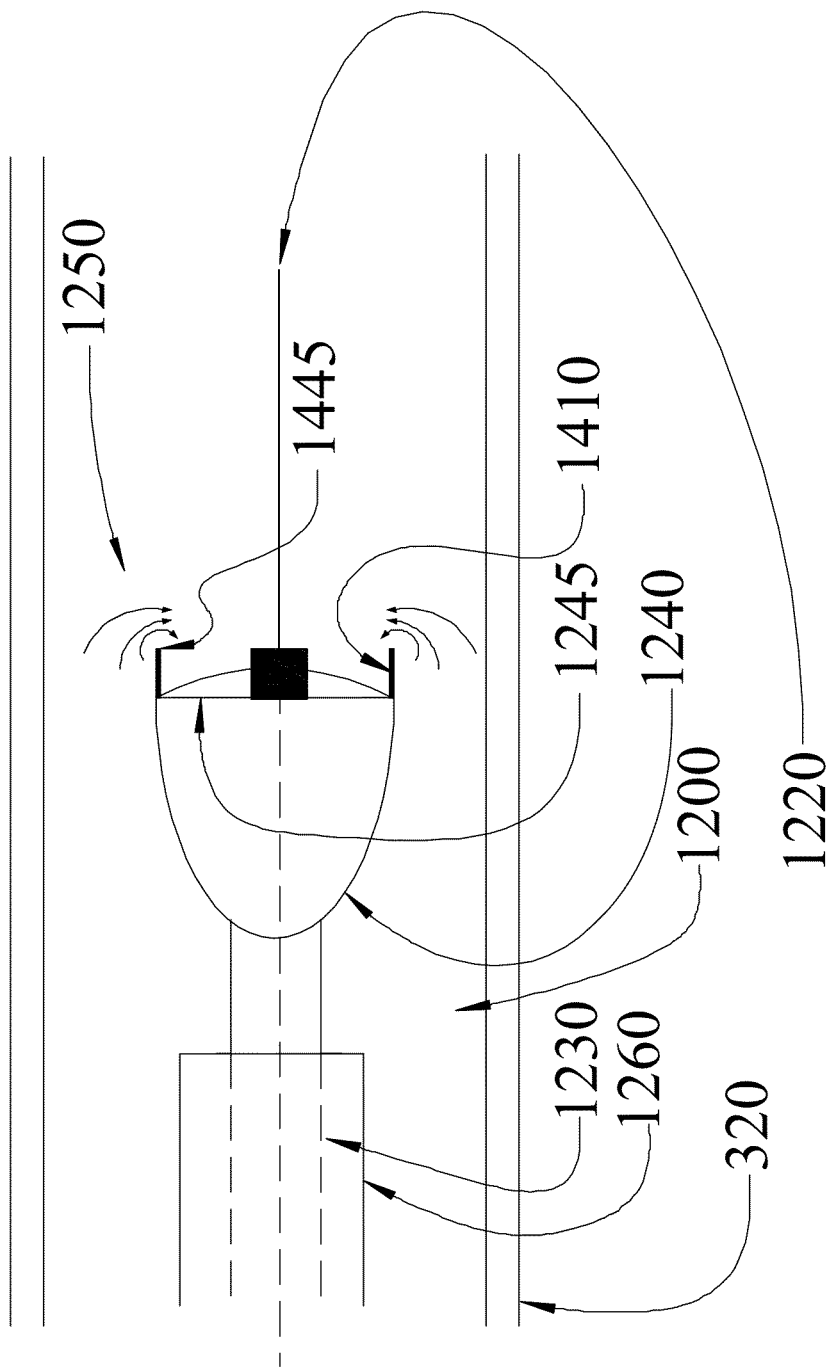
FIG. 14 illustrates a delivery catheter similar to that of FIG. 12 but comprising tabs with trailing edges.

As shown in FIG. 14, a delivery catheter 1200 includes an elongate portion adapted, in some embodiments, for percutaneous delivery. The delivery catheter 1200 also includes a catheter portion 1260 coaxial with the drug delivery lumen 1230 through which a drug or pharmaceutical may be delivered to the vessel lumen 320. A guidewire 1220 sits within the delivery catheter 1200, to aid in moving the delivery catheter 1200 to a desired delivery region. To aid its mixing, the drug exits through diffusion member 1240. Diffusion member 1240 causes the blood to divert creating turbulent blood flow 1250 as the blood transitions across the edge 1245 of diffusion member 1240. Attached to the edge 1245 of diffusion member 1240 are tabs with trailing edges 1410 with inner surface 1445.

Figure 15:
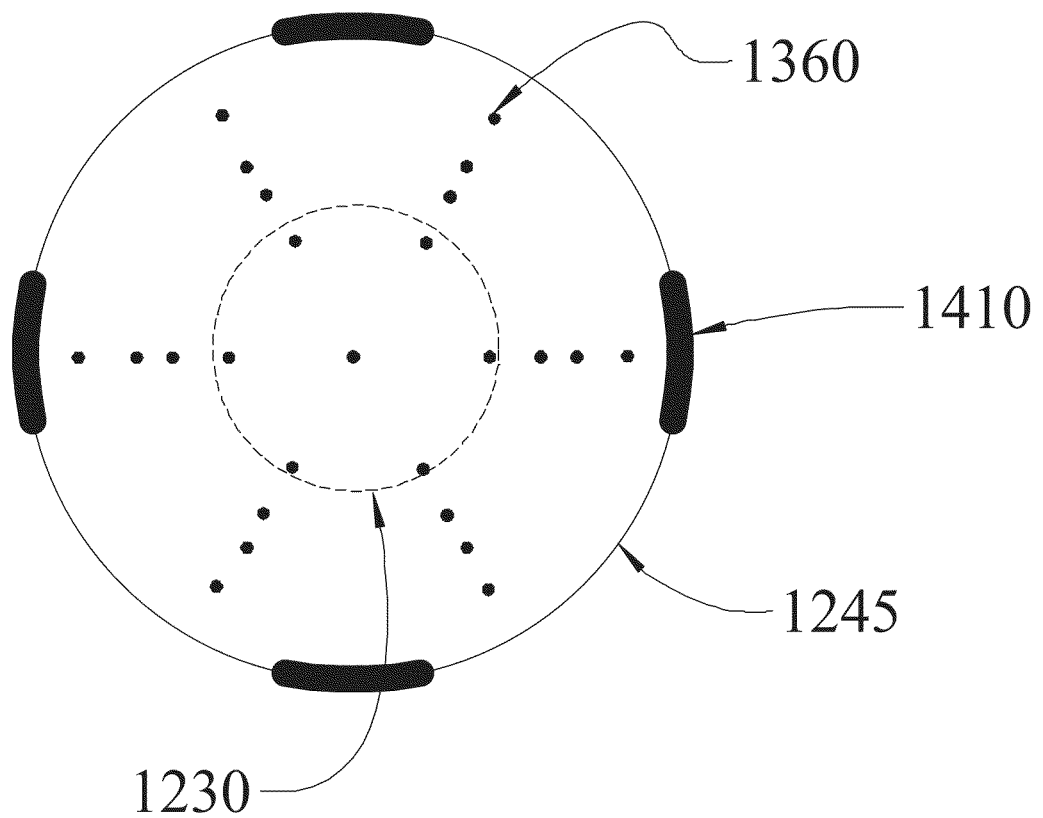
FIG. 15 illustrates the distal end of delivery catheter of FIG. 14.

FIG. 15 shows an alternate view of the delivery catheter 1200 looking at the distal end of the delivery catheter 1200. As can be seen, the guidewire 1220 is centered in the delivery catheter 1200. Diffusion member 1200 predominates in this view. The edge 1245 of diffusion member 1240 appears as a circle with tabs extending out from the circle creating trailing edges 1410. In this embodiment, the multiple delivery ports 1360 are shown located symmetrically, although any arrangement would suit the invention. Tabs with trailing edges 1410 are shown end on, as well.

In operation, the delivery catheter 1200 is delivered percutaneously (in some embodiments) to blood vessel 320 over guidewire 1220. After delivery, appropriate tension on guidewire 1220 causes diffusion member 1240 to adopt its operational or unfolded position. Once placed into its operational position, drugs or pharmaceuticals travel down drug delivery lumen 1230 through the diffusion member 1240 and then out through delivery port 1360.

The tabs with trailing edges 1410 act similarly to the plain edge, edge 1245 of FIG. 12 and FIG. 13. The trailing edge 1410 provides additional length to the edge structure and by this length creates a longer region of turbulent blood flow 1250. As before, the confluence of the turbulent blood flow 1250 and the released drug or pharmaceutical compound promotes quicker mixing between the blood and drug or pharmaceutical.

Figure 16:
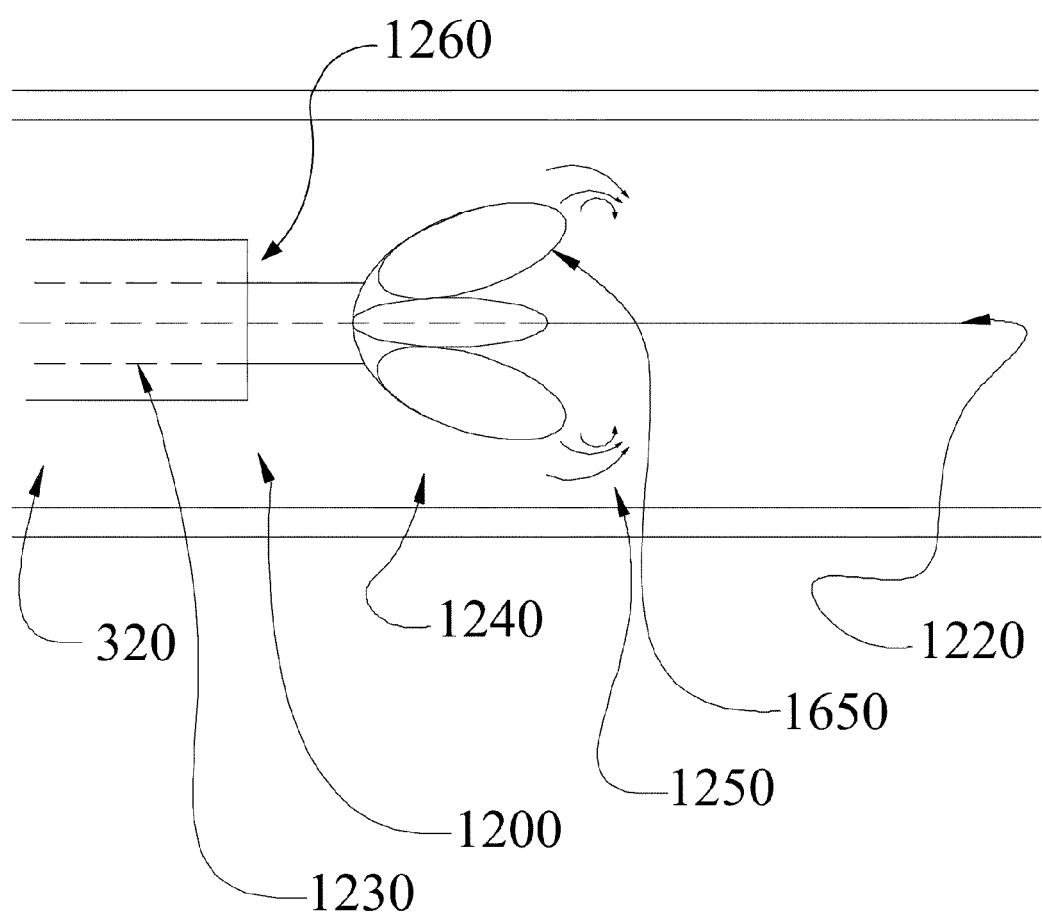
FIG. 16 illustrates a delivery catheter that includes a finned elongate portion.

As shown in FIG. 16, a delivery catheter 1200 includes an elongate portion adapted, in some embodiments, for percutaneous delivery. The delivery catheter 1200 also includes a catheter portion 1260 coaxial with the drug delivery lumen 1230 through which a drug or pharmaceutical may be delivered to the vessel lumen 320. A guidewire 1220 sits within the delivery catheter 1200, to aid in moving the delivery catheter 1200 to a desired delivery region. To aid its mixing, drug exits through diffusion member 1240. Diffusion member 1240 causes the blood to divert creating turbulent blood flow 1250 as the blood transitions across the edge 1745 (show in FIG. 17) of diffusion member 1240. The FIG. 16 embodiment has a diffusion member 1240 that comprises two or more fins 1650. The delivery ports 1360 sit along the fins 1650. The fins 1650 have edges 1745 to create turbulent blood flow 1250. Diffusion member 1240 can be made from a flexible polymer (Pebax, nylon etc) in order to be expanded and refolded within the catheter sheath. One method of diffusion member expansion is that the drug solution, soluble or microparticles, delivered through drug delivery lumen 1230 inflates 1240 by internal fluid pressure.

Figure 17:
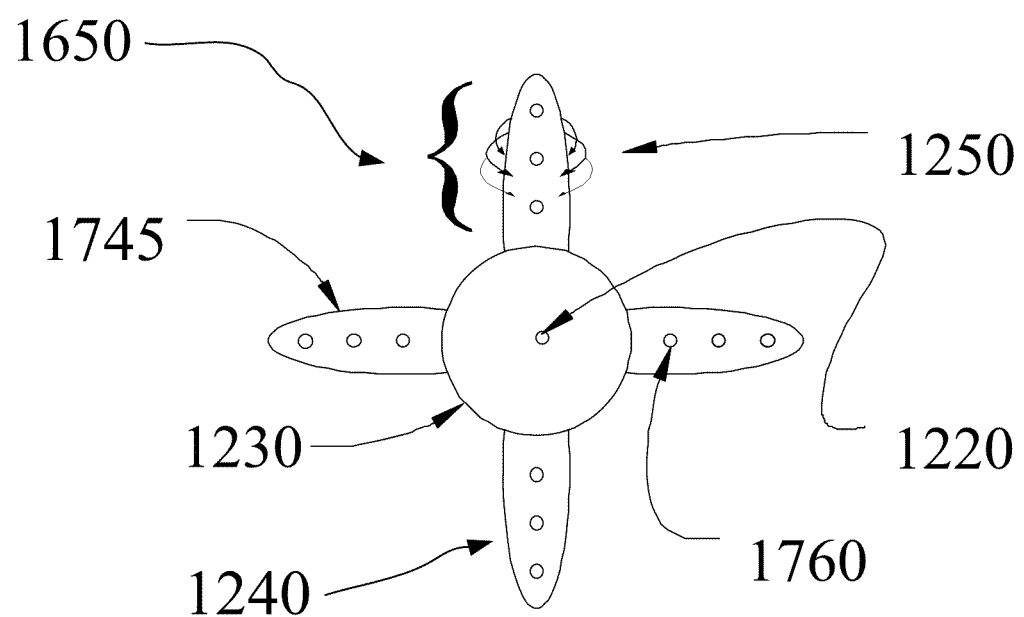
FIG. 17 illustrates the distal end of the delivery catheter of FIG. 16.
Figure 18:
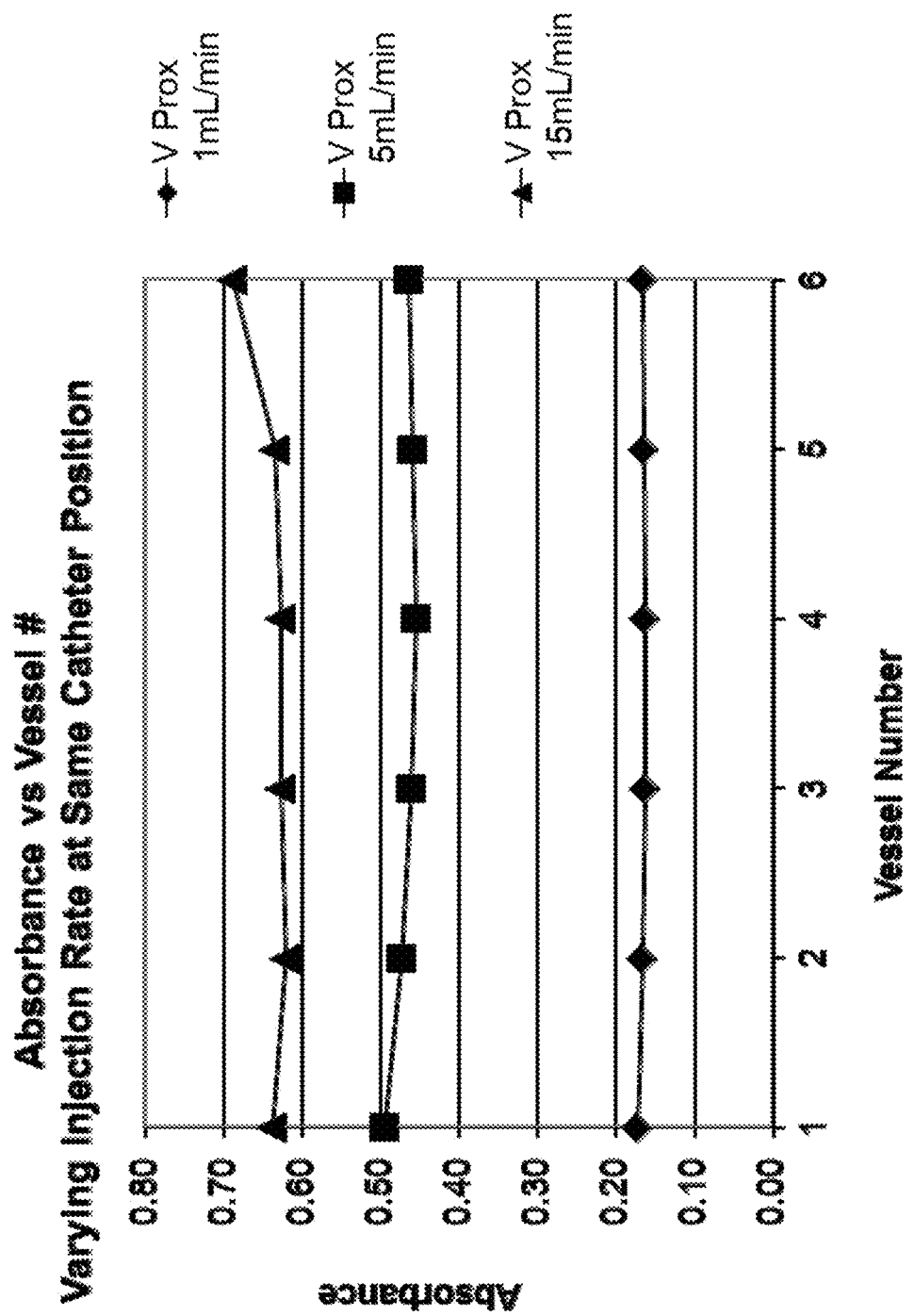
FIG. 18 is a graph showing absorbance versus vessel number for experiments in which the catheter injection position was placed at the proximal position and held constant and the infusion rate was varied.
Figure 19:
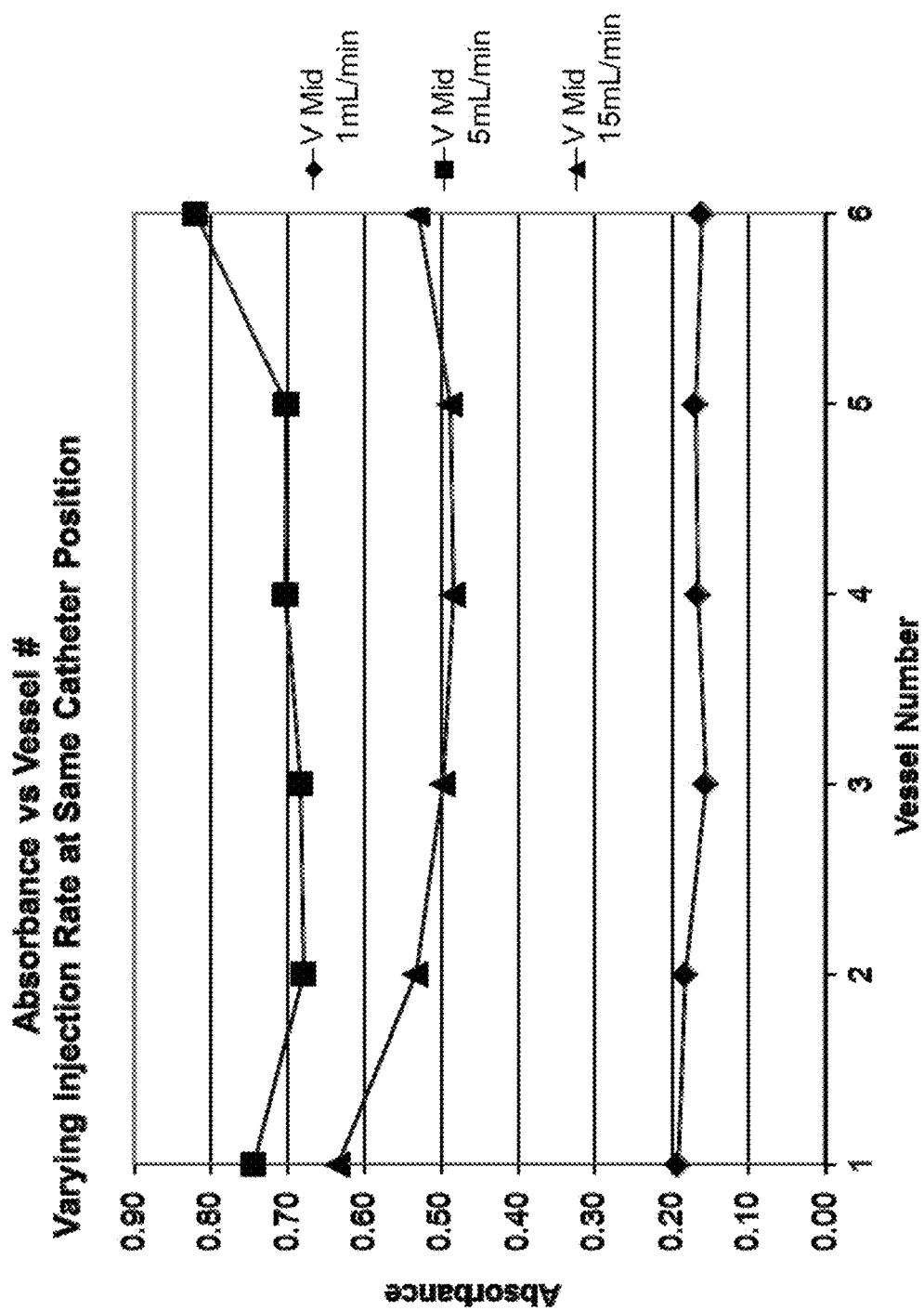
FIG. 19 is a graph showing absorbance versus vessel number for experiments in which the catheter injection position was placed at the middle position and held constant and the infusion rate was varied.

FIG. 17 shows an alternate view of the delivery catheter 1200 looking at the distal end of the delivery catheter 1200. As can be seen, the guidewire 1220 is centered in the delivery catheter 1200. Diffusion member 1200 predominates in this view. The edge 1745 of diffusion member 1240 appears as a series of pseudo-elliptical shapes in this view. In this embodiment, the multiple delivery ports 1760 are shown located symmetrically, although any arrangement would suit the invention. As can be seen in this edge-on view, the fins 1650 create a longer edge 1745 than the FIG. 16 embodiment's circular edge.

In operation, the delivery catheter 1200 is delivered percutaneously (in some embodiments) to blood vessel 320 over guidewire 1220. After delivery, appropriate tension on guidewire 1220 causes diffusion member 1240 to adopt its operational or unfolded position. Once placed into its operational position, drugs or pharmaceuticals travel down drug delivery lumen 1230 through the diffusion member 1240 and then out through delivery port 1360.

The edge 1745 of the diffusion member 1240 interferes with blood flow and creates a turbulent blood flow region 1250 that at least partially extends across the end of diffusion member 1240 moving through the region where delivery ports 1360 deposit the drug or pharmaceutical composition. The confluence of the turbulent blood flow 1250 and the released drug or pharmaceutical compound promotes quicker mixing between the blood and drug or pharmaceutical.

Figure 20:
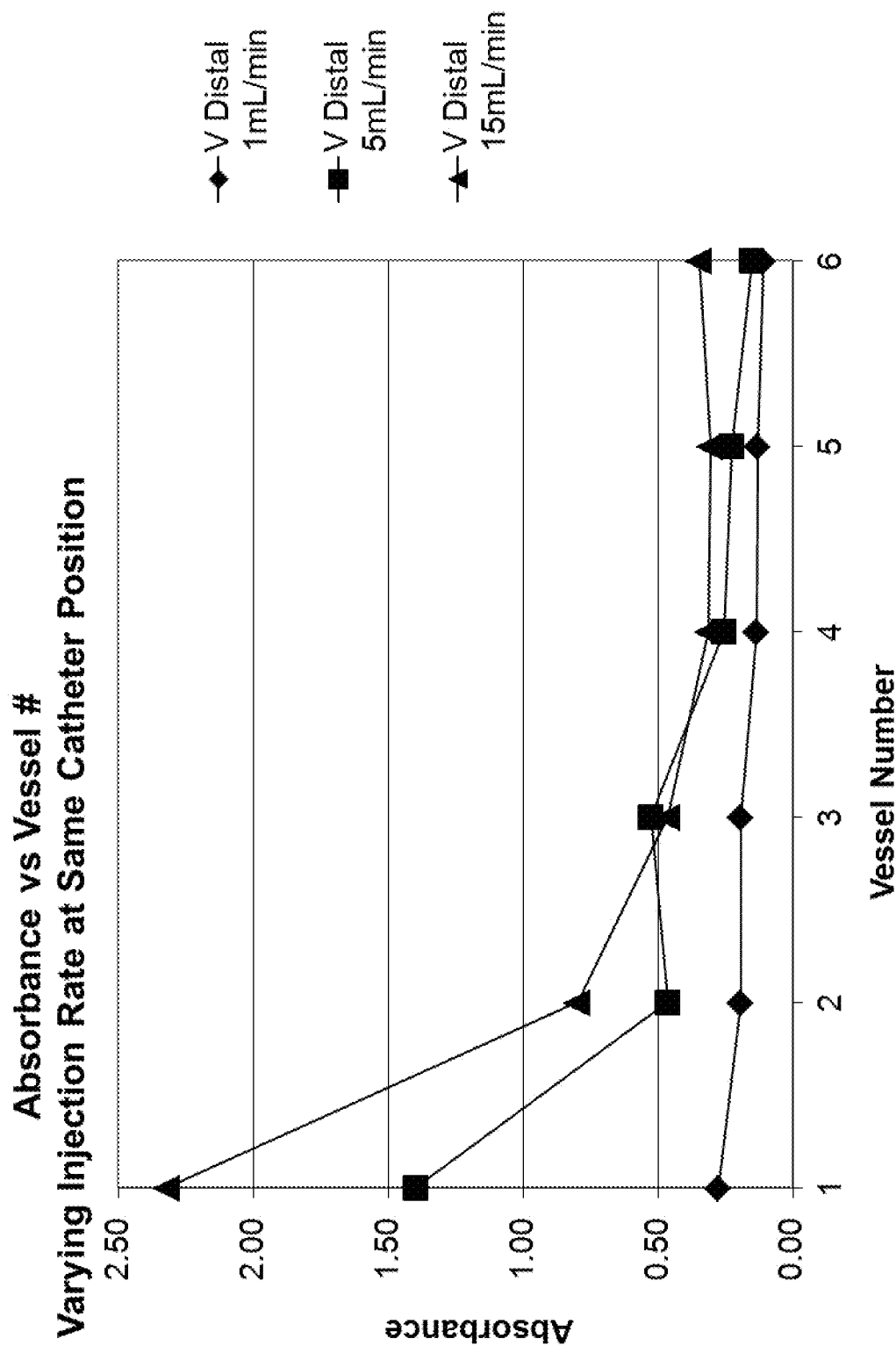
FIG. 20 is a graph showing absorbance versus vessel number for experiments in which the catheter injection position was placed at the distal position and held constant and the infusion rate was varied.

As can be seen in FIG. 18-FIG. 21, the degree that the absorbance changes from one vessel to the next as the injection rate changes depends upon the distance between the arterial branches and the injection position. Further distances, for example, proximal (FIG. 18) and middle (FIG. 19) show less dependence on injection rate than shorter distances such as distal (FIG. 20).

Without wishing to be bound by any theory, the data supports the observation that injection rate does correlate with absorbance uniformity. In FIG. 20, the higher injection rate shows less uniform absorbances among the vessels than the lower injection rates when the catheter is positioned distally. Despite this correlation for distally injected drugs solutions, the absorbances for the middle and proximal injection positions do not correlate with injection rate. This difference seems to indicate that injection position more strongly affects absorbance uniformity than does injection rate. Perhaps the higher injection rates yield, less uniform mixing of the blood initially, but having a longer mixing time or perhaps distance overcomes this initially poor mixing.

Figure 21:
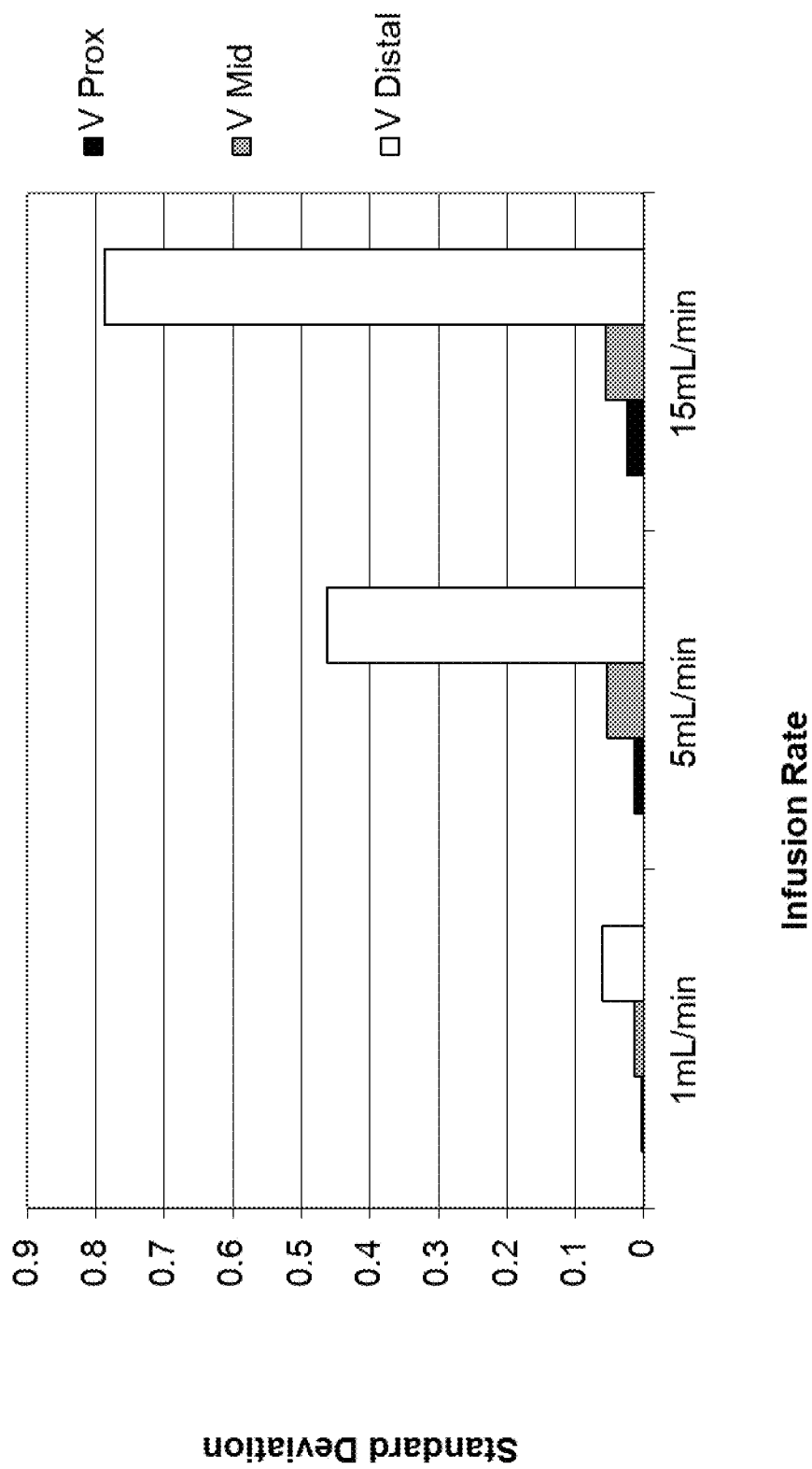
FIG. 21 is a graph showing standard deviation of the absorbance values for 6 vessels versus catheter injection position for a Veripath catheter.
Figure 22:
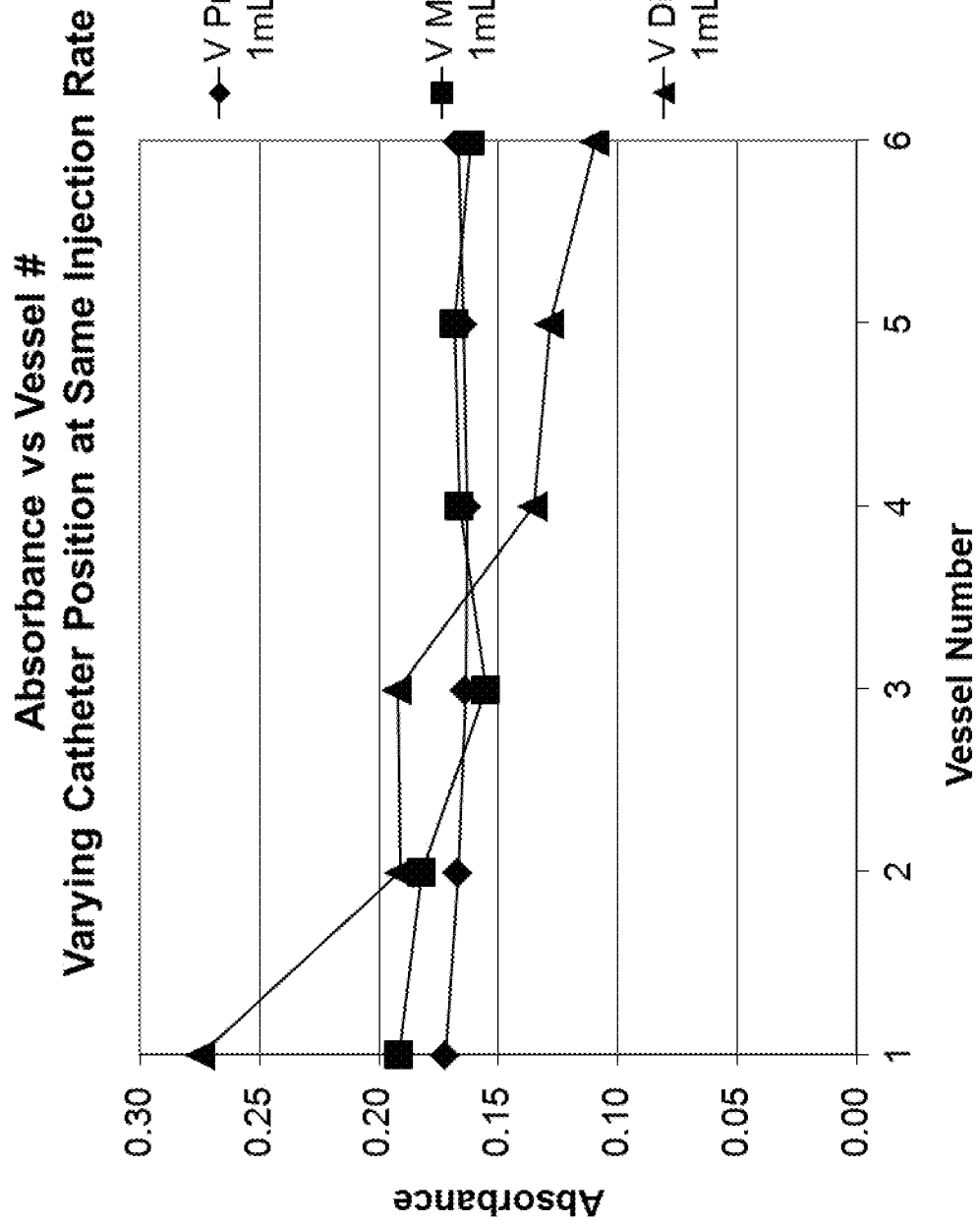
FIG. 22 is a graph showing absorbance versus vessel number for experiments in which the infusion rate was held constant at 1 mL per minute and the catheter injection position was varied.
Figure 23:
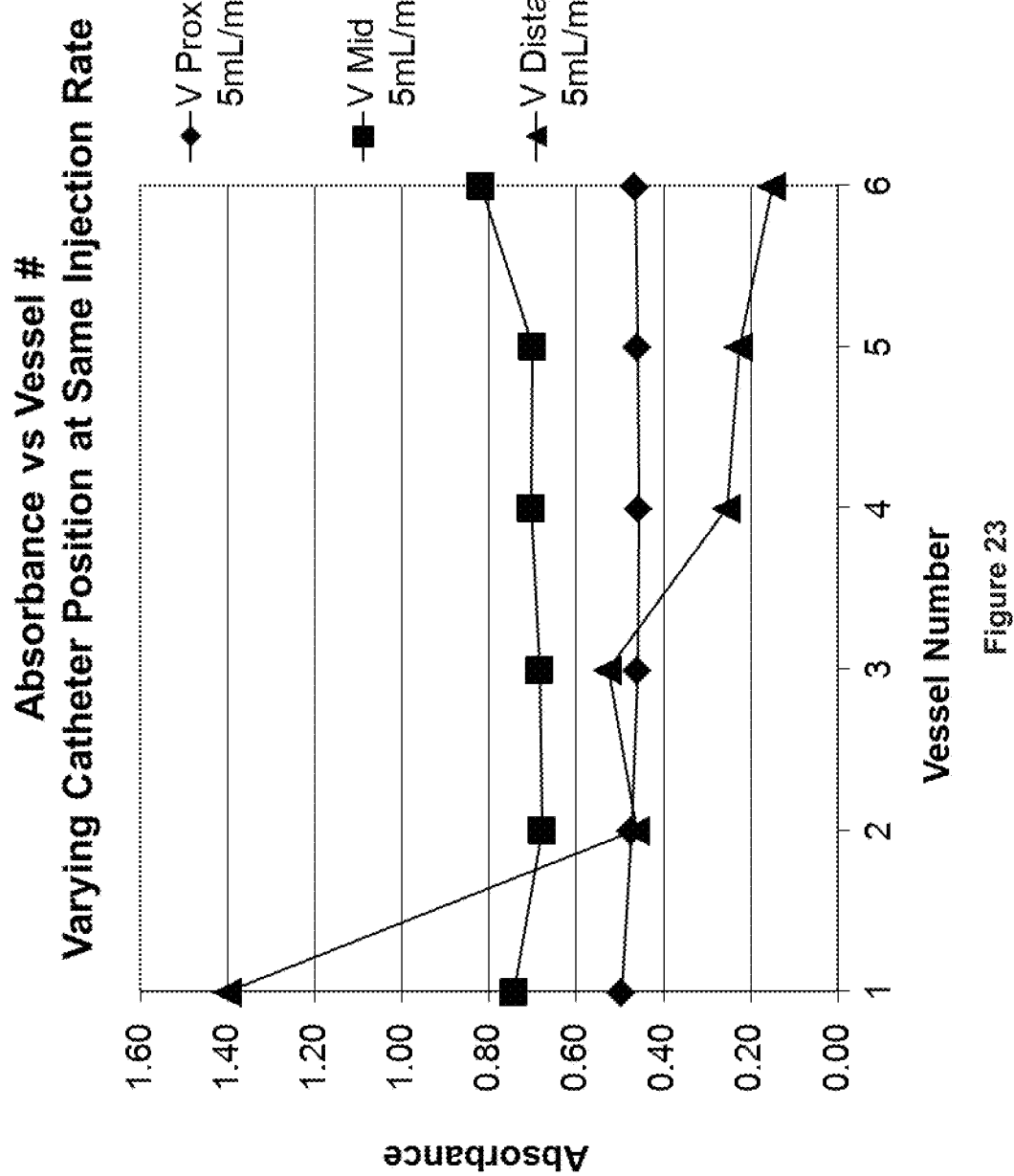
FIG. 23 is a graph showing absorbance versus vessel number for experiments in which the infusion rate was held constant at 5 mL per minute and the catheter injection position was varied.
Figure 24:
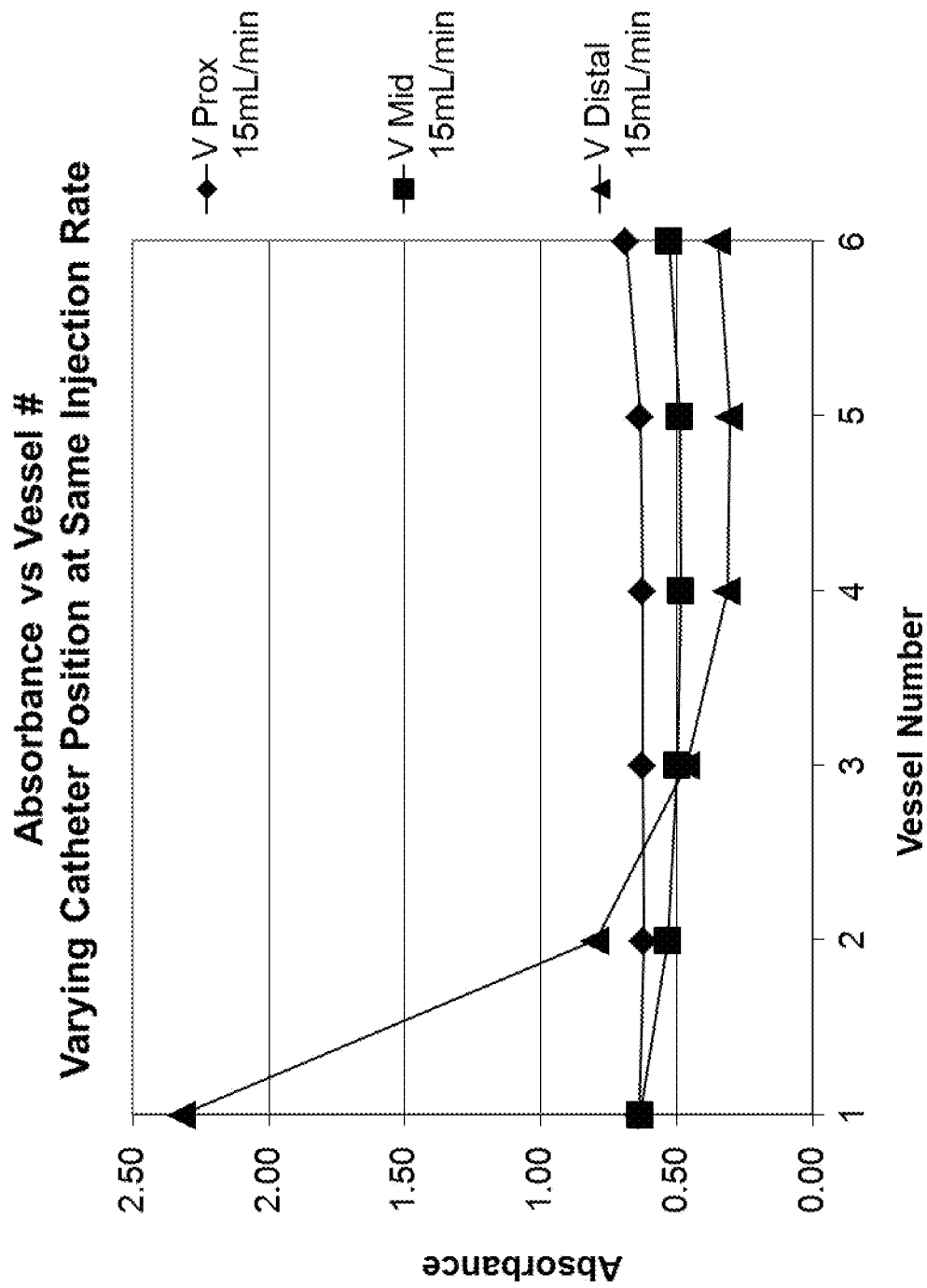
FIG. 24 is a graph showing absorbance versus vessel number for experiments in which the infusion rate was held constant at 15 mL per minute and the catheter injection position was varied.

FIG. 22-FIG. 24 shows the difference in absorbance for each of six vessels in a kidney model while maintaining the injection rate and catheter design). As discussed above for FIG. 18-FIG. 21, the data appears to show that injection rate matters to absorbance uniformity but less so than does catheter position.

Figure 25:
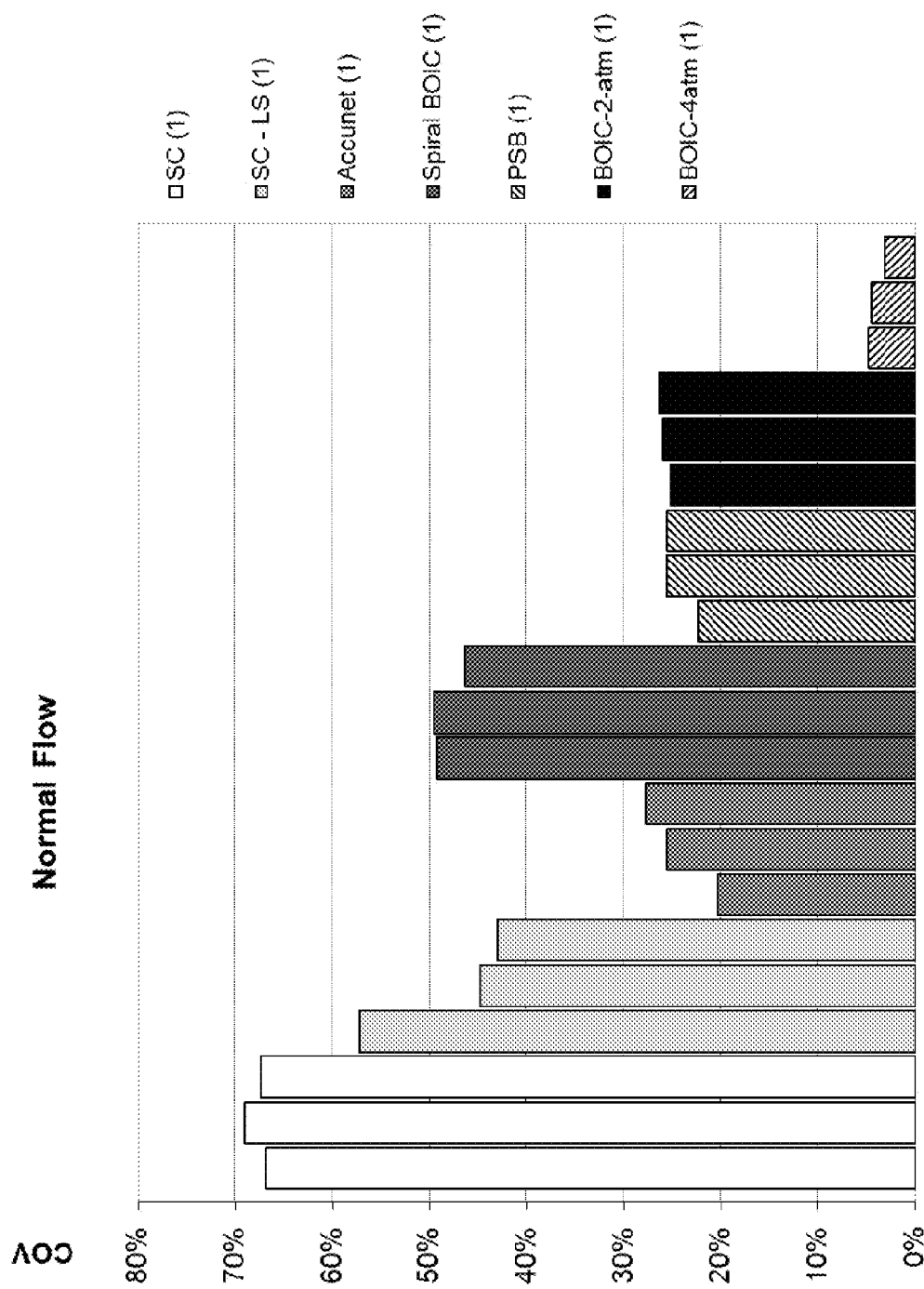
FIG. 25 shows the coefficient of variance (COV) for a variety of catheter designs as described in Example 15.

FIG. 25 shows the coefficient of variance (COV) for a variety of catheter designs as described in Example 15.

The experimental section contains a description of these catheter designs. Each design was used three times for each regimen. The COV is a measure of the variance of the standard deviations of the six vessels in a kidney model. Thus, smaller values indicate smaller standard deviations of absorbance among the vessels. And therefore, they indicate higher uniformity in drug distribution among the vessel and ultimately better mixing upstream of the vessel branches.

For most of the catheter designs, the data shows similar COVs for each of the separate runs, which indicates that the experiments yield reproducible results.

The date illustrates the catheter design matters to drug mixing. Generally, the SC design induces less turbulence than the SCLS design followed by BOIC-2-atm and BOIC-4-atm. Therefore, apparently increasing turbulence around the injection position increases mixing between the blood and the drug solution.

Treatment Agents

As used herein, treatment agents are intended to include, but are not limited to, drugs, biologically active agents, chemically active agents, therapeutic agents, and the like, and pharmaceutical compositions thereof, which can be used to deliver a treatment agent to a treatment site within a kidney as described herein. Treatments agents may contain a mixture of active agents.

In one embodiment, the treatment agent may include a property to inhibit a biological process contributing to nephropathy. Such biological processes may include, but are not limited to, changes in glomerular basement membrane, changes in mesangial matrix deposition and podocyte attachment or apoptosis.

In one embodiment, the treatment agent may include a drug. The drug may have a property to inhibit undesirable effects of the renin-angiotensin system in the kidneys. The renin-angiotensin system responds to a decrease in the perfusion of the juxtaglomerular apparatus found in afferent arterioles of the glomerulus of the kidney by constricting glomerular arterioles. Such constriction causes blood to build up in the glomerulus and increase glomerular pressure. Representative drugs that may act to inhibit this process include, but are not limited to, angiotensin converting enzyme (ACE) inhibitors, angiotensin receptor blockers (ARBs) and renin inhibitors.

In still further embodiments, the treatment agent may include a drug to inhibit protein kinase C. Representative drugs may include, but are not limited to, ruboxistaurin (LY333531), enzastau (LY317615), bisindolylmaleimide IX, chelerythrine, edelfosine, edelfosina, ET180CH3, H7, HA-100, H89, HA-1004, Ro 31-8220, rottlerin, staurosporine and quercetin.

The transforming-growth-factor-beta system contributes to the progression of renal damage due to stimulation of extracellular matrix deposition. Thus, in some embodiments, the treatment agent may include an agent having a property to inhibit transforming growth factor beta, its receptor and SMAD and other signaling molecules downstream of the receptor. Representative inhibitors may include, but are not limited to antisense molecules, ribozymes, siRNA, antibodies, receptor kinase inhibitors and other small molecule inhibitors such as halofuginone, sirolimus, everolimus, biolimus ABT578 and nuclear receptor agonists such as estradiol, retinoids, and peroxisome proliferator-activated receptors (PPAR) agonists.

It is further recognized that connective tissue growth factor (CTGF) is present in glomeruli in patients with diabetic nephropathy. CTGF is a member of the centrosomin (CCN) family of proteins, which regulate biological processes including stimulation of cell proliferation, migration, and adhesion. Probably, expression of CTGF in diabetic kidneys contributes to the development of glomerulosclerosis by affecting matrix synthesis and its turnover. In this aspect, the treatment agent may include an agent having a property to inhibit connective tissue growth factor. Representative agents having a property to inhibit connective tissue growth factor may include, but are not limited to antibodies, interleukin-1 (IL-1) alpha and beta, Rho A GTPase inhibitors, and p38 MAP kinase inhibitors.

In some embodiments, the treatment agent may be modified to enhance its uptake into the desired tissue. In this aspect, the treatment agent may be delivered to the desired tissue in a formulation that may include vasoactive agents as enhancers of vascular permeability called excipients, such as thrombin, bradykinin and histamine. These excipients have properties that increase endothelial porosity and thereby enhance uptake of the treatment agent into the tissue.

The treatment agent may be delivered in a form including, but not limited to, a solution. For example, in some embodiments, a desired amount of treatment agent is mixed with saline or an iodine-free contrast media to form the solution.

In some embodiments, the treatment agent may be delivered to the desired tissue in a carrier. In one aspect, the carrier may be a sustained-release carrier that allows for controlled release of the treatment agent over time at the desired treatment site. "Carrier" includes a matrix that contains one or more treatment agents. A suitable carrier may take the form of a nanoparticle (e.g., nanosphere), microparticle (e.g., microsphere) or liposome as the situation may dictate. The carrier with encapsulated treatment agent may be incorporated into a solution including an oily material for delivery to the desired tissue.

The carrier may be a bioerodable carrier (hereinafter interchangeably referred to as sustained-release carriers) infused with a treatment agent. Suitable materials for sustained-release carriers include, but are not limited to, encapsulation polymers such as poly (L-lactide), poly (D,L-lactide), poly (glycolide), poly (lactide-co-glycolide), polycaprolactone, polyanhydride, polydioxanone, polyorthoester, polyamino acids, or poly (trimethylene carbonate), and combinations of these materials.

Treatment agents, including treatment agents combined with a carrier (e.g., a sustained release carrier), having a size greater than about 10 microns can become trapped in the glomerular capillaries when introduced into the renal artery. In this aspect, the treatment agent may be released over time at a point within the glomerular capillaries. In other embodiments, the carrier size may be between about 1 micron to 100 microns, still further between about 8 microns to about 15 microns and in some embodiments between about 1 micron to 2 microns. In other embodiments, the carrier size may be between about 10 microns and 14 microns. In still further embodiments where the treatment agent is delivered at a point outside of a vessel lumen, such as the kidney cortex, the treatment agent or a carrier encapsulating the treatment agent may be any size capable of being delivered through a lumen of the delivery device, such as for example, a size as small as one nanometer to as large as about 100 microns.

Various methods may be employed to formulate and infuse the carrier with one or more treatment agents. The embodiments of the composition of infused carrier may be prepared by conventional methods where all components are combined then blended. In some embodiments, carriers may be prepared using a predetermined amount of a polymer or a prepolymer that is added to a predetermined amount of a solvent or a combination of solvents. The solvent is mutually compatible with the polymer and is capable of dissolving the polymer into solution at the desired concentration. Examples of solvents may include, but are not limited to, dimethylsulfoxide (DMSO), Dimethyl Acetamide (DMAC), chloroform, acetone, water (buffered saline), xylene, acetone, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, N-methyl pyrrolidinone, toluene and mixtures of these materials.

By way of example, and not limitation, the polymer may comprise from about 0.1% to about 35%, more narrowly about 2% to about 20% by weight of the total weight of the total solution, and the solvent may comprise from about 65% to about 99.9%, more narrowly about 80% to about 98% by weight, of the total weight of the total solution. Specific weight ratios depend on factors such as the material from which the delivery device is made and the geometrical structure of the device.

Sufficient amounts of treatment agent are dispersed or dissolved in the carrier. The amount of treatment agent introduced into the carrier may be any amount sufficient to inhibit a biological process, such as a biological process contributing to nephropathy, when released within the renal system. The treatment agent may be dissolved or suspended. If the treatment agent is not completely soluble in the composition, operations including mixing, stirring, or agitation may be employed to effect homogeneity. The treatment agent may be added so that the dispersion is in fine particles. The mixing of the treatment agent may be conducted in an anhydrous atmosphere, at ambient pressure and at room temperature.

In some embodiments using microparticles or nanoparticles, the microparticles or nanoparticles may be sustained release carriers prepared by a water/oil/water (WOW) double emulsion method. The WO phase, an aqueous phase containing treatment agent, is dispersed into the oil phase containing polymer dissolved in organic solvent (e.g., dichloromethane) using a high-speed homogenizer. Examples of sustained-release polymers that may be used include, but are not limited to, poly(D,L-lactide-co-glycolide) (PLGA), poly(D,L-lactide) (PLA) or PLA-PEEP co-polymers, poly-ester-amide co-polymers (PEA) and polyphophazines. The primary water-in-oil (WO) emulsion is then dispersed to an aqueous solution containing a polymeric surfactant, e.g., polyvinyl alcohol) (PVA), and further homogenized to produce a WOW emulsion. After stirring for several hours, the microparticles or nanoparticles are collected by filtration.

In some embodiments, the sustained-release carrier is a liposome. "Liposomes" are approximately spherical artificial vesicles and can be produced from natural phospholipids and cholesterol. In one method, phospholipids are mixed with cholesterol in chloroform. Suitable phospholipids include, but are not limited to, dimyristoyl phosphatidyl choline or dipalmitoyl phosphatidyl ethanolamine. In some embodiments, a hydrophobic treatment agent may be added with an optional co-solvent. After mixing, the solvent (and optional co-solvent) may be evaporated with heat or ambient temperature in a round bottom flask. Resultant lipids may be deposited on the glass surface. In some embodiments, a hydrophilic treatment agent and water may be added to the flask and sonicated to form liposomes. The resultant solution may be pressure filtered through ceramic pore size controlled filters to reduce liposome particle size. In still further embodiments, the carrier is a microbubble formed by any technique deemed desirable.

In some embodiments, a surface of the carrier may be modified to enhance affinity of the encapsulated treatment agent to tissue lining the walls of the glomerular capillaries. In this aspect, the surface may be coated with binding agents. The binding agent may include a protein or small molecule that will facilitate retention of the carrier and encapsulated treatment agent at the treatment site to induce or modulate a therapeutic response through interaction with a specific binding site (e.g., a receptor within a cell or on a cell surface). Representative binding agents and their associated receptors include, but are not limited to, CD1 Ib/CD1 8 (MAC-1) or aL/beta2 integrin (LFA-1) and intracellular adhesion molecule-1 (ICAM-1) receptor, integrin avb3 which binds to RGD-containing peptide and E-selectin which binds to Sialyl-Lewis glycoprotein.

A surface charge of the carrier may further be modified (e.g. positively, negatively or neutral) to accommodate and enhance binding characteristics to the glomerular tissue. The endothelial cells and basement membrane along the normal glomerular capillary walls are typically electronegatively charged. As diseases such as glomerulosclerosis and diabetic nephropathy progress, however, these cells slowly lose the electronegative charge. It is believed that modifying the carriers to have an electropositive charge will enhance binding of the carrier and encapsulated agent to the cells or membrane.

In this aspect, a carrier encapsulating the treatment agent may be modified by any standard method suitable for providing the carrier surface with an electropositive charge. In one embodiment, positively charged carriers may be synthesized by coating carriers with Chitosan. Alternatively, positively charged carriers may be made, for example, entirely of Chitosan in a water-in-oil emulsion process and crosslinked with glutaral-dehye or genipin. In this aspect, the treatment agent may be swell-loaded in the crosslinked spheres. Still further, if the treatment agent is soluble at pH 5, the treatment agent may be incorporated into the initial Chitosan solution, if it does not subsequently react with the aldehyde crosslinker. Another approach for forming cationic carriers may include using a polylysine graft of PLGA.

In still further embodiments, a surface of the carrier may beh coated with active agents or other species to enhance the range of functionalities of the product. For example, the surface may be coated with a monoclonal antibody that selectively binds to proteins expressed within the glomerulus (glomerular endothelium, basement membrane, podocytes) and tubules (tubular epithelium and basement membrane). A representative example is the monoclonal antibody anti CD90/Thy 1 that binds to OX-7 a glomerular basement membrane protein. Other useful proteins include nephrin and podocin.

EXPERIMENTAL

The data set out below were collected on a kidney model. This model allows the investigation of the degree of mixing between the blood and the administered therapeutic-agent solution. For accurate data collection, the model has several components: a model of the kidney vasculature; a fluidics system; an infusion system; a sample collection system, and ancillary data analysis systems or methods.

The vascular model contains an anatomically correct, 1:1 scale model of the renal arteries of a human kidney. This model is constructed from silicone. The vascular anatomy model was constructed in two different versions: one with a tortuous anatomy and one with a straight anatomy. The tortuous anatomy features a curved renal artery section between the model aorta and the arterial branches within the model kidney. And the straight anatomy features a straight and slightly shorter section in place of the curve renal artery section of the tortuous version.

At the ends of the six main kidney vessels, the anatomical model transitions back to standard tubing. Each tube is segregated so that solution can be collected individually so that the concentration of the therapeutic agent can be determined for each of the arteries in the model separately.

The fluidics system provides the fluid input to the model and sends the fluid output from the model arteries to the sample collection portion. To provide a realistic model of mixing in the kidney vasculature, the fluid flow through the model arteries should simulate the fluid flow through a real kidney. Fluid flow through this model kidney is marked by a flow rate and a pulsating pressure (just as in a real kidney, which exhibits a systolic and diastolic blood pressure).

For the data collected below, the flow rate was set to 600 mL per minute and the blood pressure was set at approximately 120 over 80 mmHg.

A standard roller pump provided the baseline flow rate. The pulsing pressure came from a pulsing pump. The pressures and flow rates are measured and controlled with pressure sensors.

Carrier Fluid for this data collection is either water or a water solution with 36% glycerol (which has a viscosity of around four centipoise). See Example 1.

For supplying the model drug solution, the model used an automated infusion pump. The pump for the infusion system was a Harvard syringe pump. For a typical experiment, the volume of model drug solution was one milliliter typically delivered at a rate of 5 mL per minute. The model drug solution for these data was a 35% solution of red food coloring in water. Thus, the model drug is red food coloring.

As discussed above, each model artery discharges into a dedicated collection vessel. Once collected, the concentration of drug (red dye) is measured using absorbance spectroscopy (Spectramax unit). The closer the concentrations of dye in the samples from each model artery are to each other, the more uniform the drug delivery down each artery. Thus, lower standard deviations of the concentrations from each of the individual model arteries indicate better mixing.

To represent homogeneity of mixing between the six independent vessels, the coefficient of variation (COV) is calculated. The COV is the ratio of the standard deviation to the mean. It can be used to compare the amount of variance between populations with different means. The absolute value of the coefficient of variation is referred to as the relative standard deviation (RSD) and is measure of precision among a set of data points. As it pertains to this invention, the COV or RSD is a measure of the variance of the standard deviations of the six vessels in a kidney model. A smaller COV or RSD value indicates smaller standard deviations of absorbance among the six vessels and thus, indicates higher uniformity in drug distribution among the vessel and ultimately better mixing.

These examples use a variety of delivery catheters:

A "Veripath catheter" is a Veripath brand catheter, which is a delivery catheter with a tapered tip and a single delivery port located at the distal end of the catheter;

A "VSH" is a Veripath brand catheter modified with side holes, which is a delivery catheter with a tapered tip and a delivery port located at the distal end of the catheter. The catheter has 15 additional holes placed near the distal end of the catheter but emerging from the sides of the catheter rather than the tip. Each of the holes is approximately 250 μm in diameter;

An "SCLS" is a Support Catheter Lifestream brand catheter. This catheter has 8 holes of around 300 micrometers diameter that are formed in the side of the catheter tip and spaced back from the tip of the catheter, which also as a single delivery located at the distal end of the catheter body;

An "SCE" is a Support Catheter Esprit brand catheter. This catheter has 9 holes of around 320 micrometers diameter that are formed in the side of the catheter tip and spaced back from the tip of the catheter, which also has a single delivery located at the distal end of the catheter body;

An "SC" is an Abbott Support Catheter, which is a single lumen catheter used for assisting guide wire delivery or infusing therapeutic agents;

An "AN" is an Accunet brand embolic protection device;

An "SB" is a spiral balloon infusion catheter with an independent infusion lumen.

A "PSB" is a Porous Spiral Balloon with a holes in a proximal taper;

A "BOIC2" is a balloon occlusion infusion catheter inflated to 2.0 atmospheres of pressure;

A "BOIC4" is a balloon occlusion infusion catheter inflated to 4.0 atmospheres of pressure;

Example 1

The circulating fluid in this example was a blood substitute (mixture of water and glycerol) with a viscosity of roughly 4 centipoise. An infusion catheter was tracked to the entry of the renal artery proximal to the branching of the main renal artery into the six smaller diameter branches. Each of the six branches emptied into separate vials. The model drug fluid contained red dye so that after its infusion, each of the six vials would receive a certain concentration of dye. Therefore, using an absorbance measurement device (SpectraMax), the absorbance value is linkable to an amount of dye. With this system, the lower the standard deviation between vials, the better or more uniform the mixing of the drug in the blood upstream of the arterial branch.

Two fluids (water and the blood substitute) containing the same concentration of dye were chosen as the model drug fluid to understand the influence of viscosity on mixing. The data verified that solutions with viscosity more alike the main fluid stream would exhibit better mixing. In this case, the model drug fluid, which was the blood substitute+dye, mixed more completely than when the model drug fluid was water+dye.

Table 1 and Table 2 show the data.

TABLE 1

|  |  | Vessel 1 | Vessel 2 | Vessel 3 | Vessel 4 | Vessel 5 | Vessel 6 |
|---|---|---|---|---|---|---|---|
| Water and | Run 1 | 0.539 | 0.656 | 0.727 | 0.691 | 0.781 | 1.145 |
| Dye Solution | Run 2 | 0.519 | 0.639 | 0.692 | 0.652 | 0.777 | 1.181 |
| Absorbance | Run 3 | 0.505 | 0.632 | 0.710 | 0.623 | 0.748 | 1.138 |
| Average |  | 0.521 | 0.642 | 0.710 | 0.655 | 0.769 | 1.154 |

Infusion rate is 1.5 ml at 5 ml/min

| Average | St. Dev. | % RSD |
|---|---|---|
| 0.742 | 0.218 | 29.4% |

TABLE 2

| Glycerol and | 0.585 | 0.730 | 0.841 | 0.863 | 0.782 | 0.825 |
|---|---|---|---|---|---|---|
| Dye Solution | 0.604 | 0.727 | 0.826 | 0.868 | 0.778 | 0.819 |
| Absorbance | 0.618 | 0.713 | 0.808 | 0.856 | 0.787 | 0.821 |
| Average | 0.603 | 0.723 | 0.825 | 0.862 | 0.782 | 0.821 |

Infusion rate is 1.5 ml at 5 ml/min

| Avg. | St. Dev. | % RSD |
|---|---|---|
| 0.769 | 0.094 | 12.3% |

In Table 1 and Table 2, above, the data points are the absorbance values from each of the six branches. The % RSD values are the most important values to note. The experiments with the lower % RSD exhibited more uniform mixing. Therefore, as the data shows, the glycerol and dye solution (which is actually glycerol+water+dye) has a lower % RSD than the water and dye solution.

In summary, the uniformity or level of mixing can be seriously influenced by the viscosity of the model drug fluid and the difference between that viscosity and the viscosity of the main fluid stream (usually blood). The more similar the viscosities of the model drug fluid and the main fluid stream, the better the mixing. Therefore, one can tune the level of mixing desired by adjusting the viscosity of the deliverable.

Example 2

This set of experiments varies the distance from the delivery port of the catheter to the first branch point in the multi-branched vessels. The data is set out in Table 3, Table 4, and Table 5.

Each set of experiments uses a Veripath catheter. The model renal flow rate is 10 mL per second.

Table 3 shows the absorbance data for a variety of model infusion rates and model drug volumes with the delivery port located at a proximal position—15 mm downstream of the aorta-renal-artery branch.

Table 4 shows the absorbance data for a variety of model infusion rates and model drug volumes with the delivery port located at a middle position—40 mm downstream of the aorta-renal-artery branch.

Table 5 shows the absorbance data for a variety of model infusion rates and model drug volumes with the delivery port located at a distal position—60 mm downstream of the aorta-renal-artery branch.

FIG. 21 displays the standard deviations from Table 3, Table 4, and Table 5 for all three infusion rates and three delivery locations. As stated previously, this data supports the claims that for simple, single lumen catheter designs (Veripath), increased distance before bifurcations allows for better mixing. As ones moves closer to the bifurcations, mixing is increasingly difficult but lower injection rates can improve it.

TABLE 3

| Infusion Rate (mL/Min) | Infusion Vol (mL) | Absorbance | | | | | |
|---|---|---|---|---|---|---|---|
|  |  | 1 | 2 | 3 | 4 | 5 | 6 |
| 1.0 | 0.2 | 0.1821 | 0.1607 | 0.1604 | 0.1601 | 0.1592 | 0.16 |
|  |  | 0.1618 | 0.1693 | 0.1657 | 0.1656 | 0.1684 | 0.1702 |
|  |  | 0.1723 | 0.17 | 0.165 | 0.1644 | 0.1669 | 0.17 |
|  | Average | 0.1721 | 0.1667 | 0.1637 | 0.1634 | 0.1648 | 0.1667 |
|  | Stdev | 0.010 | 0.005 | 0.003 | 0.003 | 0.005 | 0.006 |
|  | Average | 0.1662 |  | COV | 0.01923 |  |  |
|  | Stdev | 0.003196 |  |  |  |  |  |
| 5.0 | 1.0 | 0.5315 | 0.4689 | 0.4545 | 0.4326 | 0.456 | 0.462 |
|  |  | 0.4767 | 0.4738 | 0.4655 | 0.4774 | 0.4616 | 0.466 |
|  |  | 0.4774 | 0.4757 | 0.4615 | 0.4562 | 0.4618 | 0.4655 |
|  | Average | 0.4952 | 0.4728 | 0.4605 | 0.4554 | 0.4598 | 0.4645 |
|  | Stdev | 0.031 | 0.004 | 0.006 | 0.022 | 0.003 | 0.002 |
|  | Average | 0.4680 |  | COV | 0.03107 |  |  |
|  | Stdev | 0.014542 |  |  |  |  |  |
| 15 | 1.0 | 0.6828 | 0.6158 | 0.6181 | 0.6291 | 0.6297 | 0.6851 |
|  |  | 0.6213 | 0.629 | 0.6313 | 0.6287 | 0.6411 | 0.6866 |
|  |  | 0.611 | 0.619 | 0.6315 | 0.6227 | 0.635 | 0.6933 |
|  | Average | 0.6384 | 0.6213 | 0.6270 | 0.6268 | 0.6353 | 0.6883 |
|  | Stdev | 0.039 | 0.007 | 0.008 | 0.004 | 0.006 | 0.004 |
|  | Average | 0.6395 |  | COV | 0.03864 |  |  |
|  | Stdev | 0.024714 |  |  |  |  |  |

TABLE 4

| Infusion Rate (mL/Min) | Infusion Vol (mL) | Absorbance | | | | | |
|---|---|---|---|---|---|---|---|
| | | 1 | 2 | 3 | 4 | 5 | 6 |
| 1.0 | 0.2 | 0.2018 | 0.182 | 0.1486 | 0.1659 | 0.1698 | 0.1604 |
| | | 0.1879 | 0.1835 | 0.1584 | 0.1641 | 0.1698 | 0.1615 |
| | | 0.1852 | 0.1809 | 0.1584 | 0.1695 | 0.1662 | 0.1619 |
| | Average | 0.1916 | 0.1821 | 0.1551 | 0.1665 | 0.1686 | 0.1613 |
| | Stdev | 0.009 | 0.001 | 0.006 | 0.003 | 0.002 | 0.001 |
| | Ave | 0.1709 | | COV | 0.07946 | | |
| | Stdev | 0.01358 | | | | | |
| 5.0 | 1.0 | 0.7179 | 0.6619 | 0.696 | 0.706 | 0.7029 | 0.8401 |
| | | 0.7509 | 0.7018 | 0.6852 | 0.6962 | 0.6973 | 0.8145 |
| | | 0.7637 | 0.6759 | 0.671 | 0.7062 | 0.7032 | 0.8071 |
| | Average | 0.7442 | 0.6799 | 0.6841 | 0.7028 | 0.7011 | 0.8206 |
| | Stdev | 0.024 | 0.020 | 0.013 | 0.006 | 0.003 | 0.017 |
| | Ave | 0.7221 | | COV | 0.07387 | | |
| | Stdev | 0.053338 | | | | | |
| 15 | 1.0 | 0.6306 | 0.5238 | 0.4875 | 0.4708 | 0.4626 | 0.5298 |
| | | 0.6399 | 0.5278 | 0.497 | 0.4814 | 0.5057 | 0.5285 |
| | | 0.6324 | 0.547 | 0.5078 | 0.5009 | 0.4968 | 0.5315 |
| | Average | 0.6343 | 0.5329 | 0.4974 | 0.4844 | 0.4884 | 0.5299 |
| | Stdev | 0.005 | 0.012 | 0.010 | 0.015 | 0.023 | 0.002 |
| | Ave | 0.5279 | | COV | 0.10627 | | |
| | Stdev | 0.0561 | | | | | |

TABLE 5

| Infusion Rate (mL/min) | Infusion Vol (mL) | Absorbance | | | | | |
|---|---|---|---|---|---|---|---|
| | | 1 | 2 | 3 | 4 | 5 | 6 |
| 1.0 | 0.2 | 0.2739 | 0.1918 | 0.1928 | 0.1378 | 0.1291 | 0.1098 |
| | | 0.2723 | 0.1909 | 0.1921 | 0.1346 | 0.1275 | 0.1091 |
| | | 0.2767 | 0.191 | 0.1915 | 0.1332 | 0.1278 | 0.1096 |
| | Average | 0.2743 | 0.1912 | 0.1921 | 0.1352 | 0.1281 | 0.1095 |
| | Stdev | 0.002 | 0.000 | 0.001 | 0.002 | 0.001 | 0.000 |
| | Average | 0.1718 | | COV | 0.35334 | | |
| | Stdev | 0.060704 | | | | | |
| 5.0 | 1.0 | 1.3997 | 0.4679 | 0.5333 | 0.2654 | 0.2274 | 0.1467 |
| | | 1.4012 | 0.4615 | 0.522 | 0.2522 | 0.2284 | 0.1568 |
| | | 1.3916 | 0.4545 | 0.521 | 0.2451 | 0.2211 | 0.1456 |
| | Average | 1.3975 | 0.4613 | 0.5254 | 0.2542 | 0.2256 | 0.1497 |
| | Stdev | 0.005 | 0.007 | 0.007 | 0.010 | 0.004 | 0.006 |
| | Average | 0.5023 | | COV | 0.91925 | | |
| | Stdev | 0.461737 | | | | | |
| 15 | 1.0 | 2.2887 | 0.7998 | 0.4672 | 0.3156 | 0.3053 | 0.3499 |
| | | 2.3906 | 0.8032 | 0.4609 | 0.3144 | 0.3043 | 0.3466 |
| | | 2.2784 | 0.7921 | 0.462 | 0.3126 | 0.3008 | 0.3468 |
| | Average | 2.3192 | 0.7984 | 0.4634 | 0.3142 | 0.3035 | 0.3478 |
| | Stdev | 0.062 | 0.006 | 0.003 | 0.002 | 0.002 | 0.002 |
| | Average | 0.7577 | | COV | 1.03882 | | |
| | Stdev | 0.787113 | | | | | |

Example 3

This set of experiments varies the distance from the delivery port of the catheter to the first branch point in the multi-branched vessels. The data is shown in Table 6, Table 7, and Table 8.

Each set of experiments uses a VSH catheter. The model renal flow rate is 10 mL per second.

Table 6 shows the absorbance data for a variety of model infusion rates and model drug volumes with the delivery port located at a proximal position—15 mm downstream of the aorta-renal-artery branch.

Table 7 shows the absorbance data for a variety of model infusion rates and model drug volumes with the delivery port located at a middle position—40 mm downstream of the aorta-renal-artery branch.

Table 8 shows the absorbance data for a variety of model infusion rates and model drug volumes with the delivery port located at a distal position—60 mm downstream of the aorta-renal-artery branch.

TABLE 6

| Infusion Rate (mL/min) | Infusion Vol (mL) | Absorbance 1 | 2 | 3 | 4 | 5 | 6 |
|---|---|---|---|---|---|---|---|
| 1 | 0.2 | 0.1629 | 0.1597 | 0.1591 | 0.1588 | 0.1558 | 0.1602 |
| | | 0.1592 | 0.1593 | 0.1579 | 0.1576 | 0.1625 | 0.1622 |
| | | 0.161 | 0.1645 | 0.1697 | 0.1689 | 0.1678 | 0.1676 |
| | Average | 0.1610 | 0.1612 | 0.1622 | 0.1618 | 0.1620 | 0.1633 |
| | Stdev | 0.002 | 0.003 | 0.006 | 0.006 | 0.006 | 0.004 |
| | Ave | 0.1619 | | COV | 0.00516 | | |
| | Stdev | 0.000835 | | | | | |
| 5 | 1 | 0.4937 | 0.4959 | 0.4923 | 0.49 | 0.4886 | 0.494 |
| | | 0.5085 | 0.4959 | 0.4926 | 0.4932 | 0.4925 | 0.4939 |
| | | 0.51 | 0.5061 | 0.4943 | 0.4957 | 0.4844 | 0.492 |
| | Average | 0.5041 | 0.4993 | 0.4931 | 0.4930 | 0.4885 | 0.4933 |
| | Stdev | 0.009 | 0.006 | 0.001 | 0.003 | 0.004 | 0.001 |
| | Ave | 0.4952 | | COV | 0.01119 | | |
| | Stdev | 0.00554 | | | | | |
| 15 | 1 | 0.7234 | 0.7104 | 0.7177 | 0.7188 | 0.7133 | 0.7274 |
| | | 0.7139 | 0.7146 | 0.7238 | 0.7129 | 0.7174 | 0.7135 |
| | | 0.7073 | 0.7089 | 0.7113 | 0.7085 | 0.7165 | 0.7232 |
| | Average | 0.7149 | 0.7113 | 0.7176 | 0.7134 | 0.7157 | 0.7214 |
| | Stdev | 0.008 | 0.003 | 0.006 | 0.005 | 0.002 | 0.007 |
| | Ave | 0.7157 | | COV | 0.00488 | | |
| | Stdev | 0.003495 | | | | | |

TABLE 7

| Infusion Rate (mL/min) | Infusion Vol (mL) | Absorbance 1 | 2 | 3 | 4 | 5 | 6 |
|---|---|---|---|---|---|---|---|
| 1 | 0.2 | 0.225 | 0.2063 | 0.2107 | 0.1777 | 0.1676 | 0.1672 |
| | | 0.1822 | 0.1872 | 0.1856 | 0.1824 | 0.1758 | 0.1693 |
| | | 0.1826 | 0.1795 | 0.1779 | 0.1709 | 0.1681 | 0.1676 |
| | Average | 0.1966 | 0.1910 | 0.1914 | 0.1770 | 0.1705 | 0.1680 |
| | Stdev | 0.025 | 0.014 | 0.017 | 0.006 | 0.005 | 0.001 |
| | Average | 0.1824 | | COV | 0.06641 | | |
| | Stdev | 0.012114 | | | | | |
| 5 | 1 | 0.5316 | 0.4874 | 0.4835 | 0.4611 | 0.4737 | 0.4839 |
| | | 0.4962 | 0.4846 | 0.4863 | 0.4831 | 0.4727 | 0.4753 |
| | | 0.4961 | 0.4857 | 0.4804 | 0.4753 | 0.4768 | 0.477 |
| | Average | 0.5080 | 0.4859 | 0.4834 | 0.4732 | 0.4744 | 0.4787 |
| | Stdev | 0.020 | 0.001 | 0.003 | 0.011 | 0.002 | 0.005 |
| | Average | 0.4839 | | COV | 0.02639 | | |
| | Stdev | 0.012772 | | | | | |
| 15 | 1 | 0.7906 | 0.7414 | 0.7416 | 0.7536 | 0.7344 | 0.7422 |
| | | 0.7505 | 0.7247 | 0.6959 | 0.7151 | 0.7118 | 0.7239 |
| | | 0.7381 | 0.6975 | 0.7035 | 0.7206 | 0.6962 | 0.7096 |
| | Average | 0.7597 | 0.7212 | 0.7137 | 0.7298 | 0.7141 | 0.7252 |
| | Stdev | 0.027 | 0.022 | 0.024 | 0.021 | 0.019 | 0.016 |
| | Average | 0.7273 | | COV | 0.02348 | | |
| | Stdev | 0.01708 | | | | | |

TABLE 8

| Infusion Rate (mL/min) | Infusion Vol (mL) | Absorbance 1 | 2 | 3 | 4 | 5 | 6 |
|---|---|---|---|---|---|---|---|
| 1 | 0.2 | 0.1345 | 0.1906 | 0.1985 | 0.1806 | 0.1754 | 0.1486 |
| | | 0.1296 | 0.176 | 0.1892 | 0.1722 | 0.1686 | 0.1462 |
| | | 0.128 | 0.1787 | 0.1899 | 0.1689 | 0.167 | 0.1466 |

TABLE 8-continued

| Infusion Rate (mL/min) | Infusion Vol (mL) | Absorbance | | | | | |
|---|---|---|---|---|---|---|---|
| | | 1 | 2 | 3 | 4 | 5 | 6 |
| | Average | 0.1307 | 0.1818 | 0.1925 | 0.1739 | 0.1703 | 0.1471 |
| | Stdev | 0.003 | 0.008 | 0.005 | 0.006 | 0.004 | 0.001 |
| | Average | 0.1661 | | COV | 0.13823 | | |
| | Stdev | 0.02296 | | | | | |
| 5 | 1 | 0.3901 | 0.6497 | 0.7698 | 0.5992 | 0.5672 | 0.3699 |
| | | 0.3751 | 0.6409 | 0.7499 | 0.6007 | 0.5663 | 0.3715 |
| | | 0.3867 | 0.633 | 0.7667 | 0.6166 | 0.5717 | 0.3675 |
| | Average | 0.3840 | 0.6412 | 0.7621 | 0.6055 | 0.5684 | 0.3696 |
| | Stdev | 0.008 | 0.008 | 0.011 | 0.010 | 0.003 | 0.002 |
| | Average | 0.5551 | | COV | 0.27519 | | |
| | Stdev | 0.15276 | | | | | |
| 15 | 1 | 0.5215 | 0.7946 | 0.9082 | 0.7524 | 0.6557 | 0.4282 |
| | | 0.5231 | 0.7502 | 0.8918 | 0.7608 | 0.6741 | 0.4198 |
| | | 0.4857 | 0.7351 | 0.8893 | 0.7467 | 0.6666 | 0.4313 |
| | Average | 0.5101 | 0.7600 | 0.8964 | 0.7533 | 0.6655 | 0.4264 |
| | Stdev | 0.021 | 0.031 | 0.010 | 0.007 | 0.009 | 0.006 |
| | Average | 0.6686 | | COV | 0.26009 | | |
| | Stdev | 0.1739 | | | | | |

Example 4

This set of experiments uses water as the carrier or system fluid. The model drug solution (red dye) is injected at a rate of 1 or 5 mL/min through a delivery catheter that is either a SCLS or SCE. The output of the catheter is located at a middle position (Mid) that is 40 mm downstream of the aorta-renal-artery branch or at a distal position (Distal) that is 60 mm downstream of the aorta-renal-artery branch.

The model kidney vasculature is the tortuous form. Table 9 sets out the data from this example.

Example 5

This set of experiments uses water as the carrier or system fluid. The model drug solution (red dye) is injected at a rate of 1 or 5 mL/min through a delivery catheter that is either a SCLS or SCE. The output of the catheter is located at a middle position (Mid) that is 40 mm downstream of the aorta-renal-artery branch or at a distal position (Distal) that is 60 mm downstream of the aorta-renal-artery branch.

The model kidney vasculature is the straight form.

The data in Table 9 shows the standard deviation of the absorbances for the various delivery positions.

Example 6

The kidney model uses a carrier fluid that models the fluid characteristics of blood.

This set of experiments uses a 36% glycerol in water solution as the carrier or system fluid. The model drug solution (red dye) is injected at a rate of 1 or 5 mL/min through a delivery catheter that is either a VSH or SCE. The output of the catheter is located at a middle position (Mid) that is 40 mm downstream of the aorta-renal-artery branch or at a distal position (Distal) that is 60 mm downstream of the aorta-renal-artery branch.

The model kidney vasculature is the tortuous form.

The data in Table 9 shows the standard deviation of the absorbances for the various delivery positions.

Example 7

The kidney model uses a carrier fluid that models the fluid characteristics of blood.

This set of experiments uses a 36% glycerol in water solution as the carrier or system fluid. The model drug solution (red dye) is injected at a rate of 1 or 5 mL/min through a delivery catheter that is either a VSH or SCE. The output of the catheter is located at a middle position (Mid) that is 40 mm downstream of the aorta-renal-artery branch or at a distal position (Distal) that is 60 mm downstream of the aorta-renal-artery branch. The model kidney vasculature is the straight form.

The data in Table 9 shows the standard deviation of the absorbances for the various delivery positions. Lower standard deviations in absorbance indicate more uniform absorbances vessel branch to vessel branch. From the data, drug uniformity depends on infusion rates, distances between the injection position and the vessel branch points, carrier fluid viscosity, and catheter shape. Table 9 further supports that increasing mixing follows from adding multiple deliver ports at the distal end of the catheter. VSH is the same catheter as V but modified with side holes on the distal end. Once again, a lower COV indicates less variance between the six independent vessels and better overall mixing. The data also shows that this improved, mixing is most critical when the distance between the delivery site and vessel branching is small.

TABLE 9

| | Tortuous Anatomy | | | | Straight Anatomy | | | |
|---|---|---|---|---|---|---|---|---|
| | 1 mL/min | | 5 mL/min | | 1 mL/min | | 5 mL/min | |
| | Mid | Distal | Mid | Distal | Mid | Distal | Mid | Distal |
| | System Fluid = Water | | | | | | | |
| SCLS | 0.013972 | 0.047875 | 0.06308 | 0.243688 | 0.011099 | 0.027095 | 0.014617 | 0.065181 |
| SCE | 0.015054 | 0.010326 | 0.061896 | 0.044245 | 0.020484 | 0.042636 | 0.061705 | 0.191944 |

TABLE 9-continued

| | Tortuous Anatomy | | | | Straight Anatomy | | | |
| --- | --- | --- | --- | --- | --- | --- | --- | --- |
| | 1 mL/min | | 5 mL/min | | 1 mL/min | | 5 mL/min | |
| | Mid | Distal | Mid | Distal | Mid | Distal | Mid | Distal |
| | System Fluid = Glycerol Solution | | | | | | | |
| VSH | 0.16224 | 0.086785 | 0.574318 | 0.465285 | 0.017992 | 0.018809 | 0.051321 | 0.096049 |
| SCE | 0.131551 | 0.19444 | 1.021261 | 1.014982 | 0.019935 | 0.060396 | 0.045216 | 0.258866 |

TABLE 10

| Catheter Type | Delivery Location | 1 mL/Min | 5 mL/Min | 15 mL/Min |
| --- | --- | --- | --- | --- |
| V | Proximal | 0.01923 | 0.03107 | 0.03864 |
| VSH | Proximal | 0.00516 | 0.01119 | 0.00488 |
| V | Middle | 0.07946 | 0.07387 | 0.10627 |
| VSH | Middle | 0.06641 | 0.02639 | 0.02348 |
| V | Distal | 0.35334 | 0.91925 | 1.03882 |
| VSH | Distal | 0.13823 | 0.27519 | 0.26009 |

The experiments that go along with Example 8, Example 9, and Example 10 vary the catheter type, the infusion rates, the infusion volumes of model drug solutions, and the anatomy model. The data for these examples is set out in Table 11.

Example 8

This set of experiment uses a tortuous anatomy as the kidney vasculature model and water as the carrier fluid. It uses an SCE delivery catheter. The data shows the effect of varying the injection point between mid and distal positions, as described above. The data shows the effect of varying the infusion volume of the model drug solution between 0.2 and 1 mL and of varying the infusion rate between a and 5 mL per minute.

Example 9

This set of experiment uses a tortuous anatomy as the kidney vasculature model and water as the carrier fluid. It uses an SCLS delivery catheter. The data shows the effect of varying the injection point between mid and distal positions, as described above. The data shows the effect of varying the infusion volume of the model drug solution between 0.2 and 1 mL and of varying the infusion rate between a and 5 mL per minute.

Example 10

This set of experiment uses a tortuous anatomy as the kidney vasculature model and water as the carrier fluid. It uses an VSH delivery catheter.

The data shows the effect of varying the injection point between mid and distal positions, as described above.

The data shows the effect of varying the infusion volume of the model drug solution between 0.2 and 1 mL and of varying the infusion rate between a and 5 mL per minute.

TABLE 11

| | | | SCE vs. SCLS vs. VSH | | | | | |
| --- | --- | --- | --- | --- | --- | --- | --- | --- |
| | Rate | Vol (mL) | 1 | 2 | 3 | 4 | 5 | 6 |
| | | | SCE | | | | | |
| Mid | 1 | 0.2 | 0.1422 | 0.1704 | 0.1764 | 0.1779 | 0.1813 | 0.1559 |
| | | | 0.1444 | 0.1717 | 0.1811 | 0.1792 | 0.1778 | 0.1561 |
| | | | 0.1444 | 0.1788 | 0.1796 | 0.1864 | 0.1751 | 0.1596 |
| | | Average | 0.1437 | 0.1736 | 0.1790 | 0.1812 | 0.1781 | 0.1572 |
| | | Stdev | 0.001 | 0.005 | 0.002 | 0.005 | 0.003 | 0.002 |
| | | Average | 0.1688 | | | | | |
| | | Stdev | 0.015054 | | | | | |
| | 5 | 1 | 0.417 | 0.5382 | 0.561 | 0.5539 | 0.5569 | 0.4653 |
| | | | 0.4088 | 0.5426 | 0.5667 | 0.5568 | 0.5465 | 0.4695 |
| | | | 0.4092 | 0.545 | 0.5688 | 0.5564 | 0.5472 | 0.4661 |
| | | Average | 0.4117 | 0.5419 | 0.5655 | 0.5557 | 0.5502 | 0.4670 |
| | | Stdev | 0.005 | 0.003 | 0.004 | 0.002 | 0.006 | 0.002 |
| | | Average | 0.5153 | | | | | |
| | | Stdev | 0.061896 | | | | | |
| Distal | 1 | 0.2 | 0.0907 | 0.0897 | 0.1044 | 0.099 | 0.1135 | 0.1115 |
| | | | 0.093 | 0.0904 | 0.1066 | 0.1005 | 0.1157 | 0.113 |
| | | | 0.0917 | 0.0908 | 0.1063 | 0.1009 | 0.1154 | 0.1131 |
| | | Average | 0.0918 | 0.0903 | 0.1058 | 0.1001 | 0.1149 | 0.1125 |
| | | Stdev | 0.001 | 0.001 | 0.001 | 0.001 | 0.001 | 0.001 |
| | | Average | 0.1026 | | | | | |
| | | Stdev | 0.010326 | | | | | |
| | 5 | 1 | 0.4977 | 0.3991 | 0.4679 | 0.4093 | 0.5009 | 0.4821 |
| | | | 0.5018 | 0.4015 | 0.4721 | 0.4114 | 0.4993 | 0.4833 |
| | | | 0.5031 | 0.401 | 0.4663 | 0.414 | 0.5024 | 0.4812 |
| | | Average | 0.5009 | 0.4005 | 0.4688 | 0.4116 | 0.5009 | 0.4822 |
| | | Stdev | 0.003 | 0.001 | 0.003 | 0.002 | 0.002 | 0.001 |
| | | Average | 0.4608 | | | | | |
| | | Stdev | 0.044245 | | | | | |

TABLE 11-continued

SCE vs. SCLS vs. VSH

| | Rate | Vol (mL) | 1 | 2 | 3 | 4 | 5 | 6 |
|---|---|---|---|---|---|---|---|---|
| | | | SCLS | | | | | |
| Mid | 1 | 0.2 | 0.1705 | 0.1952 | 0.1994 | 0.1978 | 0.2058 | 0.177 |
| | | | 0.1721 | 0.1969 | 0.2034 | 0.2003 | 0.2034 | 0.1778 |
| | | | 0.1713 | 0.1968 | 0.2036 | 0.2083 | 0.2006 | 0.1791 |
| | | Average | 0.1713 | 0.1963 | 0.2021 | 0.2021 | 0.2033 | 0.1780 |
| | | Stdev | 0.001 | 0.001 | 0.002 | 0.005 | 0.003 | 0.001 |
| | | Average | 0.1922 | | | | | |
| | | Stdev | 0.013972 | | | | | |
| | 5 | 1 | 0.6582 | 0.715 | 0.7166 | 0.6516 | 0.6645 | 0.5495 |
| | | | 0.6261 | 0.7226 | 0.7125 | 0.6578 | 0.6499 | 0.5511 |
| | | | 0.6179 | 0.7256 | 0.716 | 0.6543 | 0.6564 | 0.5429 |
| | | Average | 0.6341 | 0.7211 | 0.7150 | 0.6546 | 0.6569 | 0.5478 |
| | | Stdev | 0.021 | 0.005 | 0.002 | 0.003 | 0.007 | 0.004 |
| | | Average | 0.6549 | | | | | |
| | | Stdev | 0.06308 | | | | | |
| Distal | 1 | 0.2 | 0.1094 | 0.1518 | 0.1724 | 0.1889 | 0.2197 | 0.2432 |
| | | | 0.1106 | 0.1526 | 0.1759 | 0.191 | 0.2175 | 0.2446 |
| | | | 0.1096 | 0.1532 | 0.1753 | 0.1987 | 0.2145 | 0.2473 |
| | | Average | 0.1099 | 0.1525 | 0.1745 | 0.1929 | 0.2172 | 0.2450 |
| | | Stdev | 0.001 | 0.001 | 0.002 | 0.005 | 0.003 | 0.002 |
| | | Average | 0.1820 | | | | | |
| | | Stdev | 0.047875 | | | | | |
| | 5 | 1 | 0.3851 | 0.3831 | 0.5016 | 0.6061 | 0.7492 | 1.006 |
| | | | 0.3522 | 0.3877 | 0.4981 | 0.604 | 0.738 | 1.0085 |
| | | | 0.344 | 0.3904 | 0.4959 | 0.6059 | 0.724 | 1.0044 |
| | | Average | 0.3604 | 0.3871 | 0.4985 | 0.6053 | 0.7371 | 1.0063 |
| | | Stdev | 0.022 | 0.004 | 0.003 | 0.001 | 0.013 | 0.002 |
| | | Average | 0.5991 | | | | | |
| | | Stdev | 0.243688 | | | | | |
| | | | VSH | | | | | |
| Mid | 1 | 0.2 | 0.225 | 0.2063 | 0.2107 | 0.1777 | 0.1676 | 0.1672 |
| | | | 0.1822 | 0.1872 | 0.1856 | 0.1824 | 0.1758 | 0.1693 |
| | | | 0.1826 | 0.1795 | 0.1779 | 0.1709 | 0.1681 | 0.1676 |
| | | Average | 0.1966 | 0.1910 | 0.1914 | 0.1770 | 0.1705 | 0.1680 |
| | | Stdev | 0.025 | 0.014 | 0.017 | 0.006 | 0.005 | 0.001 |
| | | Average | 0.1824 | | | | | |
| | | Stdev | 0.012114 | | | | | |
| | 5 | 1 | 0.5316 | 0.4874 | 0.4835 | 0.4611 | 0.4737 | 0.4839 |
| | | | 0.4962 | 0.4846 | 0.4863 | 0.4831 | 0.4727 | 0.4753 |
| | | | 0.4961 | 0.4857 | 0.4804 | 0.4753 | 0.4768 | 0.477 |
| | | Average | 0.5080 | 0.4859 | 0.4834 | 0.4732 | 0.4744 | 0.4787 |
| | | Stdev | 0.020 | 0.001 | 0.003 | 0.011 | 0.002 | 0.005 |
| | | Average | 0.4839 | | | | | |
| | | Stdev | 0.012772 | | | | | |
| Distal | 1 | 0.2 | 0.1345 | 0.1906 | 0.1985 | 0.1806 | 0.1754 | 0.1486 |
| | | | 0.1296 | 0.176 | 0.1892 | 0.1722 | 0.1686 | 0.1462 |
| | | | 0.128 | 0.1787 | 0.1899 | 0.1689 | 0.167 | 0.1466 |
| | | Average | 0.1307 | 0.1818 | 0.1925 | 0.1739 | 0.1703 | 0.1471 |
| | | Stdev | 0.003 | 0.008 | 0.005 | 0.006 | 0.004 | 0.001 |
| | | Average | 0.1661 | | | | | |
| | | Stdev | 0.02296 | | | | | |
| | 5 | 1 | 0.3901 | 0.6497 | 0.7698 | 0.5992 | 0.5672 | 0.3699 |
| | | | 0.3751 | 0.6409 | 0.7499 | 0.6007 | 0.5663 | 0.3715 |
| | | | 0.3867 | 0.633 | 0.7667 | 0.6166 | 0.5717 | 0.3675 |
| | | Average | 0.3840 | 0.6412 | 0.7621 | 0.6055 | 0.5684 | 0.3696 |
| | | Stdev | 0.008 | 0.008 | 0.011 | 0.010 | 0.003 | 0.002 |
| | | Average | 0.5551 | | | | | |
| | | Stdev | 0.15276 | | | | | |

The experiments that go along with Example 11 and Example 12 vary the catheter type, the infusion rates, infusion volumes of model drug solutions, the catheter type, and the anatomy model. The data for these examples is set out in Table 12.

Example 11

This set of experiment uses a tortuous anatomy as the kidney vasculature model and a 36% glycerol in water solution as the carrier fluid. It uses an SCE delivery catheter.

The data shows the effect of varying the injection point between mid and distal positions, as described above.

The data shows the effect of varying the infusion volume of the model drug solution between 0.2 and 1 mL and of varying the infusion rate between 1 and 5 mL per minute.

Example 12

This set of experiment uses a tortuous anatomy as the kidney vasculature model and a 36% glycerol in water as the carrier fluid. It uses an SCLS delivery catheter.

The data shows the effect of varying the injection point between mid and distal positions, as described above.

The data shows the effect of varying the infusion volume of the model drug solution between 0.2 and 1 mL and of varying the infusion rate between a and 5 mL per minute.

TABLE 12

VSH v. SCE

|  | Rate | Vol (mL) | 1 | 2 | 3 | 4 | 5 | 6 |
|---|---|---|---|---|---|---|---|---|
| | | | VSH | | | | | |
| Mid | 1 | 0.2 | 0.4427 | 0.3755 | 0.0618 | 0.1477 | 0.2185 | 0.0609 |
| | | | 0.4442 | 0.3874 | 0.0636 | 0.1465 | 0.2237 | 0.0618 |
| | | | 0.4414 | 0.389 | 0.0632 | 0.1466 | 0.2183 | 0.0623 |
| | | Average | 0.4428 | 0.3840 | 0.0629 | 0.1469 | 0.2202 | 0.0617 |
| | | Stdev | 0.001 | 0.007 | 0.001 | 0.001 | 0.003 | 0.001 |
| | | Average | 0.2197 | | | | | |
| | | Stdev | 0.16224 | | | | | |
| | 5 | 1 | 1.4497 | 2.0984 | 0.5799 | 0.934 | 0.6098 | 0.8345 |
| | | | 1.5643 | 1.9771 | 0.5881 | 0.9453 | 0.6088 | 0.8257 |
| | | Average | 1.5070 | 2.0378 | 0.5840 | 0.9397 | 0.6093 | 0.8301 |
| | | Stdev | 0.081 | 0.086 | 0.006 | 0.008 | 0.001 | 0.006 |
| | | Average | 1.0846 | | | | | |
| | | Stdev | 0.574318 | | | | | |
| Distal | 1 | 0.2 | 0.1721 | 0.2135 | 0.2553 | 0.231 | 0.4189 | 0.1832 |
| | | | 0.1722 | 0.2228 | 0.2502 | 0.2298 | 0.4135 | 0.186 |
| | | | 0.1721 | 0.2212 | 0.2515 | 0.2379 | 0.403 | 0.1843 |
| | | Average | 0.1721 | 0.2192 | 0.2523 | 0.2329 | 0.4118 | 0.1845 |
| | | Stdev | 0.000 | 0.005 | 0.003 | 0.004 | 0.008 | 0.001 |
| | | Average | 0.2455 | | | | | |
| | | Stdev | 0.086785 | | | | | |
| | 5 | 1 | 0.7909 | 0.5286 | 1.7092 | 1.2844 | 0.8921 | 0.5451 |
| | | | 0.788 | 0.5224 | 1.6681 | 1.4286 | 0.8791 | 0.5477 |
| | | Average | 0.7895 | 0.5255 | 1.6887 | 1.3565 | 0.8856 | 0.5464 |
| | | Stdev | 0.002 | 0.004 | 0.029 | 0.102 | 0.009 | 0.002 |
| | | Average | 0.9654 | | | | | |
| | | Stdev | 0.465285 | | | | | |
| | | | SCE | | | | | |
| Mid | 1 | 0.2 | 0.034 | 0.0608 | 0.3438 | 0.306 | 0.2744 | 0.2466 |
| | | | 0.0342 | 0.0602 | 0.3506 | 0.305 | 0.2723 | 0.2474 |
| | | | 0.0336 | 0.0598 | 0.3491 | 0.2977 | 0.2757 | 0.2472 |
| | | Average | 0.0339 | 0.0603 | 0.3478 | 0.3029 | 0.2741 | 0.2471 |
| | | Stdev | 0.000 | 0.001 | 0.004 | 0.005 | 0.002 | 0.000 |
| | | Average | 0.2110 | | | | | |
| | | Stdev | 0.131551 | | | | | |
| | 5 | 1 | 0.0347 | 0.173 | 2.5453 | 0.8329 | 1.7823 | 0.2136 |
| | | | 0.0345 | 0.1743 | 2.5265 | 0.8259 | 1.7946 | 0.211 |
| | | Average | 0.0346 | 0.1737 | 2.5359 | 0.8294 | 1.7885 | 0.2123 |
| | | Stdev | 0.000 | 0.001 | 0.013 | 0.005 | 0.009 | 0.002 |
| | | Average | 0.9291 | | | | | |
| | | Stdev | 1.021261 | | | | | |
| Distal | 1 | 0.2 | 0.0345 | 0.3724 | 0.5609 | 0.1836 | 0.09 | 0.204 |
| | | | 0.0389 | 0.3841 | 0.5605 | 0.1841 | 0.0907 | 0.2088 |
| | | | 0.0415 | 0.3848 | 0.5554 | 0.1855 | 0.0892 | 0.197 |
| | | Average | 0.0383 | 0.3804 | 0.5589 | 0.1844 | 0.0900 | 0.2033 |
| | | Stdev | 0.004 | 0.007 | 0.003 | 0.001 | 0.001 | 0.006 |
| | | Average | 0.2426 | | | | | |
| | | Stdev | 0.19444 | | | | | |
| | 5 | 1 | 0.0364 | 2.208 | 2.126 | 0.3518 | 0.0959 | 0.2766 |
| | | | 0.0364 | 2.2826 | 1.9397 | 0.3606 | 0.0992 | 0.2683 |
| | | Average | 0.0364 | 2.2453 | 2.0329 | 0.3562 | 0.0976 | 0.2725 |
| | | Stdev | 0.000 | 0.053 | 0.132 | 0.006 | 0.002 | 0.006 |
| | | Average | 0.8401 | | | | | |
| | | Stdev | 1.014982 | | | | | |

The experiments that go along with Example 13 and Example 14 vary the catheter type, the infusion rates, infusion volumes of the model drug solutions, the catheter type, and the anatomy model. The data for these examples is set out in Table 13.

Example 13

This set of experiment uses a straight anatomy as the kidney vasculature model and a 36% glycerol in water solution as the carrier fluid. It uses an VSH delivery catheter.

The data shows the effect of varying the injection point between mid and distal positions, as described above.

The data shows the effect of varying the infusion volume of the model drug solution between 0.2 and 1 mL and of varying the infusion rate between 1 and 5 mL per minute.

Example 14

This set of experiment uses a tortuous anatomy as the kidney vasculature model and a 36% glycerol in water as the carrier fluid. It uses an SCE delivery catheter.

The data shows the effect of varying the injection point between mid and distal positions, as described above.

The data shows the effect of varying the infusion volume of the model drug solution between 0.2 and 1 mL and of varying the infusion rate between a and 5 mL per minute.

TABLE 13

Straight Anatomy with Bood Substitute (36% Glycerol, 3.5 cp)

| | Rate | Vol (mL) | 1 | 2 | 3 | 4 | 5 | 6 |
|---|---|---|---|---|---|---|---|---|
| | | | VSH | | | | | |
| Mid | 1 | 0.2 | 0.1905 | 0.1858 | 0.1634 | 0.1756 | 0.2041 | 0.2112 |
| | | | 0.1911 | 0.1838 | 0.1629 | 0.1795 | 0.2094 | 0.2162 |
| | | | 0.1917 | 0.1848 | 0.163 | 0.1835 | 0.2023 | 0.2114 |
| | | Average | 0.1911 | 0.1848 | 0.1631 | 0.1795 | 0.2053 | 0.2129 |
| | | Stdev | 0.001 | 0.001 | 0.000 | 0.004 | 0.004 | 0.003 |
| | | Average | 0.1895 | | | | | |
| | | Stdev | 0.017992 | | | | | |
| | 5 | 1 | 0.5299 | 0.5427 | 0.6028 | 0.5861 | 0.5473 | 0.4512 |
| | | | 0.5221 | 0.5433 | 0.6045 | 0.5728 | 0.5355 | 0.4509 |
| | | | 0.5219 | 0.5458 | 0.6033 | 0.5755 | 0.5396 | 0.4593 |
| | | Average | 0.5246 | 0.5439 | 0.6035 | 0.5781 | 0.5408 | 0.4538 |
| | | Stdev | 0.005 | 0.002 | 0.001 | 0.007 | 0.006 | 0.005 |
| | | Average | 0.5408 | | | | | |
| | | Stdev | 0.051321 | | | | | |
| Distal | 1 | 0.2 | 0.2598 | 0.2305 | 0.1978 | 0.2081 | 0.2168 | 0.2144 |
| | | | 0.2481 | 0.2337 | 0.1994 | 0.2078 | 0.2146 | 0.2133 |
| | | | 0.2473 | 0.2315 | 0.201 | 0.2075 | 0.2253 | 0.2117 |
| | | Average | 0.2517 | 0.2319 | 0.1994 | 0.2078 | 0.2189 | 0.2131 |
| | | Stdev | 0.007 | 0.002 | 0.002 | 0.000 | 0.006 | 0.001 |
| | | Average | 0.2205 | | | | | |
| | | Stdev | 0.018809 | | | | | |
| | 5 | 1 | 0.6609 | 0.5983 | 0.5358 | 0.5848 | 0.764 | 0.7963 |
| | | | 0.6706 | 0.6037 | 0.5331 | 0.5907 | 0.7546 | 0.7689 |
| | | | 0.652 | 0.5937 | 0.5321 | 0.6194 | 0.7379 | 0.7737 |
| | | Average | 0.6612 | 0.5986 | 0.5337 | 0.5983 | 0.7522 | 0.7796 |
| | | Stdev | 0.009 | 0.005 | 0.002 | 0.019 | 0.013 | 0.015 |
| | | Average | 0.6539 | | | | | |
| | | Stdev | 0.096049 | | | | | |
| | | | SCE | | | | | |
| Mid | 1 | 0.2 | 0.1779 | 0.1801 | 0.2359 | 0.2247 | 0.2132 | 0.2104 |
| | | | 0.1764 | 0.1818 | 0.215 | 0.2195 | 0.2143 | 0.2095 |
| | | | 0.1768 | 0.1817 | 0.2137 | 0.2194 | 0.2152 | 0.2091 |
| | | Average | 0.1770 | 0.1812 | 0.2215 | 0.2212 | 0.2142 | 0.2097 |
| | | Stdev | 0.001 | 0.001 | 0.012 | 0.003 | 0.001 | 0.001 |
| | | Average | 0.2041 | | | | | |
| | | Stdev | 0.019935 | | | | | |
| | 5 | 1 | 0.4833 | 0.4892 | 0.568 | 0.5877 | 0.5676 | 0.5393 |
| | | | 0.4838 | 0.4851 | 0.5835 | 0.5863 | 0.5709 | 0.5422 |
| | | | 0.4799 | 0.4839 | 0.5661 | 0.5816 | 0.571 | 0.5357 |
| | | Average | 0.4823 | 0.4861 | 0.5725 | 0.5852 | 0.5698 | 0.5391 |
| | | Stdev | 0.002 | 0.003 | 0.010 | 0.003 | 0.002 | 0.003 |
| | | Average | 0.5392 | | | | | |
| | | Stdev | 0.045216 | | | | | |
| Distal | 1 | 0.2 | 0.1688 | 0.1535 | 0.1675 | 0.1835 | 0.2663 | 0.2952 |
| | | | 0.1689 | 0.1569 | 0.1684 | 0.1822 | 0.2579 | 0.2941 |
| | | | 0.1664 | 0.1532 | 0.1684 | 0.1809 | 0.2588 | 0.3152 |
| | | Average | 0.1680 | 0.1545 | 0.1681 | 0.1822 | 0.2610 | 0.3015 |
| | | Stdev | 0.001 | 0.002 | 0.001 | 0.001 | 0.005 | 0.012 |
| | | Average | 0.2059 | | | | | |
| | | Stdev | 0.060396 | | | | | |
| | 5 | 1 | 0.4521 | 0.3895 | 0.4705 | 0.529 | 0.8824 | 1.0209 |
| | | | 0.4451 | 0.3944 | 0.4669 | 0.5275 | 0.8672 | 1.0232 |
| | | | 0.4424 | 0.3965 | 0.4669 | 0.5247 | 0.8822 | 0.9999 |

TABLE 13-continued

Straight Anatomy with Bood Substitute (36% Glycerol, 3.5 cp)

| | Rate | Vol (mL) | 1 | 2 | 3 | 4 | 5 | 6 |
|---|---|---|---|---|---|---|---|---|
| | | Average | 0.4465 | 0.3935 | 0.4681 | 0.5271 | 0.8773 | 1.0147 |
| | | Stdev | 0.005 | 0.004 | 0.002 | 0.002 | 0.009 | 0.013 |
| | | Average | 0.6212 | | | | | |
| | | Stdev | 0.258866 | | | | | |
| | | | SCLS | | | | | |
| Mid | 1 | 0.2 | 0.2084 | 0.1764 | 0.2065 | 0.2435 | 0.1619 | 0.1782 |
| | | | 0.1862 | 0.1683 | 0.2107 | 0.1927 | 0.1594 | 0.2112 |
| | | | 0.185 | 0.167 | 0.2108 | 0.1931 | 0.1593 | 0.1826 |
| | | Average | 0.1932 | 0.1706 | 0.2093 | 0.2098 | 0.1602 | 0.1907 |
| | | Stdev | 0.013 | 0.005 | 0.002 | 0.029 | 0.001 | 0.018 |
| | | Average | 0.1890 | | | | | |
| | | Stdev | 0.020171 | | | | | |
| | 5 | 1 | 0.5035 | 0.4494 | 0.6234 | 0.5702 | 0.4912 | 0.5933 |
| | | | 0.5381 | 0.4396 | 0.6265 | 0.5606 | 0.5168 | 0.5584 |
| | | | 0.4965 | 0.4422 | 0.6214 | 0.5459 | 0.496 | 0.5975 |
| | | Average | 0.5127 | 0.4437 | 0.6238 | 0.5589 | 0.5013 | 0.5831 |
| | | Stdev | 0.022 | 0.005 | 0.003 | 0.012 | 0.014 | 0.021 |
| | | Average | 0.5373 | | | | | |
| | | Stdev | 0.064329 | | | | | |
| Distal | 1 | 0.2 | 0.3004 | 0.2355 | 0.1856 | 0.1618 | 0.1691 | 0.1489 |
| | | | 0.259 | 0.2777 | 0.1902 | 0.1608 | 0.1633 | 0.1532 |
| | | | 0.2801 | 0.248 | 0.1999 | 0.1739 | 0.1584 | 0.1503 |
| | | Average | 0.2798 | 0.2537 | 0.1919 | 0.1655 | 0.1636 | 0.1508 |
| | | Stdev | 0.021 | 0.022 | 0.007 | 0.007 | 0.005 | 0.002 |
| | | Average | 0.2009 | | | | | |
| | | Stdev | 0.053399 | | | | | |
| | 5 | 1 | 0.8424 | 0.725 | 0.52 | 0.4029 | 0.5028 | 0.5683 |
| | | | 0.819 | 0.7156 | 0.5294 | 0.3992 | 0.4966 | 0.5739 |
| | | | 0.8196 | 0.7103 | 0.5243 | 0.3955 | 0.5164 | 0.5687 |
| | | Average | 0.8270 | 0.7170 | 0.5246 | 0.3992 | 0.5053 | 0.5703 |
| | | Stdev | 0.013 | 0.007 | 0.005 | 0.004 | 0.010 | 0.003 |
| | | Average | 0.5906 | | | | | |
| | | Stdev | 0.155269 | | | | | |

Example 15

For the data set out in Table 14, the absorbances for 3 experiments using each of the catheters listed below were measured for each of the six model kidney vessels. From these data, the mean, standard deviation, and coefficients of variance (COV) were calculated for each of the 3 experiments. Smaller COVs indicate more uniform absorbances within the six model kidney vessels. More uniform absorbances indicate better mixing of the model drug solution and model blood upstream of the point in the model kidney the six vessels branch from.

For the data labeled normal flow in Table 14, the experiments used a model blood pressure of 120/80, a model renal flow rate of 612 ml/min and a model heart rate of 62 beats per minute. This data is also depicted in FIG. 23.

The injection position was middle, as described above.

The rate that the model drug solution was infused was 5 ml per minute and the model drug solution volume was 1 ml.

For the data labeled slow flow in Table 14, the experiments used a model blood pressure of 100/60, a model renal flow rate of 432 ml/min and a model heart rate of 62 beats per minute. FIG. 25 depicts this data, as well.

The injection position was middle, as described above.

The rate that the model drug solution was infused was 5 ml per minute and the model drug solution volume was 1 ml.

TABLE 14

| Device | COV |
|---|---|
| Normal Flow | |
| SC (1) | 0.668639945 |
| SC (2) | 0.690450761 |
| SC (3) | 0.674122032 |
| SCLS (1) | 0.573040081 |
| SCLS (2) | 0.448106471 |
| SCLS (3) | 0.42978025 |
| AN (1) | 0.203495165 |
| AN (2) | 0.255781741 |
| AN (3) | 0.277323529 |
| SB (1) | 0.492903129 |
| SB (2) | 0.495742927 |
| SB (3) | 0.464743142 |
| PSB (1) | 0.222154851 |
| PSB (2) | 0.254763199 |
| PSB (3) | 0.254763199 |
| BOIC2 (1) | 0.251521383 |
| BOIC2 (2) | 0.261069332 |
| BOIC2 (3) | 0.263830656 |
| BOIC4 (1) | 0.047100437 |
| BOIC4 (2) | 0.044627776 |
| BOIC4 (3) | 0.031104892 |
| Slow Flow | |
| SC (1) | 0.701573548 |
| SC (2) | 0.675331237 |
| SC (3) | 0.684994408 |
| SCLS (1) | 0.431040508 |
| SCLS (2) | 0.434914758 |
| SCLS (3) | 0.295938149 |
| AN (1) | 0.400903854 |
| AN (2) | 0.41760533 |
| AN (3) | 0.357134811 |

TABLE 14-continued

| Device | COV |
|---|---|
| SB (1) | 0.479926197 |
| SB (2) | 0.502559424 |
| SB (3) | 0.459681637 |
| PSB (1) | 0.348541956 |
| PSB (2) | 0.333924232 |
| PSB (3) | 0.267846673 |
| BOIC2 (1) | 0.433731283 |
| BOIC2 (2) | 0.423053842 |
| BOIC2 (3) | 0.43001733 |
| BOIC4 (1) | 0.039802648 |
| BOIC4 (2) | 0.048597524 |
| BOIC4 (3) | 0.037685885 |

In this experiment, SC is a single lumen delivery device similar to the V catheter in previous examples. SCLS is the SC catheter with side holes in the distal end similar to the VSH catheter in previous examples. Data from Table 14 shows that an expandable diffusion member such as a balloon improves mixing more than a simple, single lumen delivery device or one with side holes improves mixing. Balloon expansion causes partial obstruction of the vessel resulting in turbulent flow around the balloon, which improves mixing. The degree of obstruction plays a role in the degree of mixing as the BOIC2 (inflated to 2 atm) is about 60% of the vessel ID versus the BOIC4 (inflated to 4 atm) is about 90% of the vessel ID.

While particular embodiments of the present invention have been shown and described, it will be obvious to those skilled in the art that changes and modifications can be made without departing from the embodiments of this invention in its broader aspects and, therefore, the appended claims are to encompass within their scope all such changes and modifications as fall within the true, intended, explained, disclose, and understood scope and spirit of this invention's multitudinous embodiments and alternative descriptions.

Additionally, various embodiments have been described above. For convenience's sake, combinations of aspects composing invention embodiments have been listed in such a way that one of ordinary skill in the art may read them exclusive of each other when they are not necessarily intended to be exclusive. But a recitation of an aspect for one embodiment is meant to disclose its use in all embodiments in which that aspect can be incorporated without undue experimentation. In like manner, a recitation of an aspect as composing part of an embodiment is a tacit recognition that a supplementary embodiment exists that specifically excludes that aspect. All patents, test procedures, and other documents cited, in this specification are fully incorporated by reference to the extent that this material is consistent with this specification and for all jurisdictions in which such incorporation is permitted.

Moreover, some embodiments recite ranges. When this is done, it is meant to disclose the ranges as a range, and to disclose each and every point within the range, including end points. For those embodiments that disclose a specific value or condition for an aspect, supplementary embodiments exist that are otherwise identical, but that specifically exclude the value or the conditions for the aspect.

Finally, headings are for the convenience of the reader and do not alter the meaning or content of the disclosure or the scope of the claims.

What is claimed is:

1. A device comprising:
a catheter including;
a main body,
a self-expanding diffusion member connected to the main body, the self-expanding diffusion member having (1) a closed proximal portion operable to hold a fluid therein; (2) a distal facing surface that is defined by an edge joining the distal facing surface to the closed proximal portion, and (3) a plurality of delivery ports formed within the distal facing surface, and wherein the self-expanding diffusion member is dimensioned to provide from 60 percent to 90 percent occlusion of a blood vessel of a mammal, and
a drug delivery lumen located in the main body, wherein the drug delivery lumen is in fluid communication with the drug delivery ports via the closed proximal portion such that a drug can be delivered from the plurality of delivery ports in a generally distal direction,
wherein the device is adapted for percutaneous delivery into the vasculature of a mammal and adapted to expand the self-expanding diffusion member within the vessel.

2. The device of claim 1 wherein the drug delivery lumen is proximal to the self-expanding diffusion member.

3. The device of claim 1 wherein the self-expanding diffusion member has a diameter between 60 and 90 percent of the vessel diameter.

4. The device of claim 1 wherein the device further comprises a deployment sheath that is movably affixed substantially coaxially to the main body.

5. The device of claim 4 wherein the self-expanding diffusion member is connected to a distal end of the main body at the closed proximal portion of the self-expanding diffusion member.

6. A device comprising a catheter including
a main body,
an expandable diffusion member connected to the main body, the expandable diffusion member having a proximal end and a distal end, and wherein the proximal end is closed such that the proximal end is operable to occlude a blood vessel within which the device is positioned and the distal end forms a distal facing surface that is defined by an edge, the distal facing surface having a plurality of delivery ports facing a generally distal direction, and
a drug delivery lumen located in the expandable diffusion member and terminating at a point proximal to the face, wherein the drug delivery lumen is in fluid communication with the drug delivery ports such that a drug can be delivered from the plurality of delivery ports in a generally distal direction,
wherein the device is adapted for percutaneous delivery into the vasculature of a mammal and adapted to expand the expandable diffusion member within a blood vessel of a mammal.

7. The device of claim 6 wherein the expandable diffusion member has a diameter between 20 and 95 percent, 40 and 93 percent, or 60 and 90 percent of the vessel diameter.

8. The device of claim 6 wherein the expandable diffusion member comprises tabs attached near the edge, which is between the distal end of the expandable diffusion member and sides of the proximal end of the expandable diffusion member.

9. The device of claim 6 wherein the distal end comprises four or more delivery ports.

* * * * *

UNITED STATES PATENT AND TRADEMARK OFFICE
CERTIFICATE OF CORRECTION

Page 1 of 1

PATENT NO. : 9,149,610 B2
APPLICATION NO. : 13/158757
DATED : October 6, 2015
INVENTOR(S) : Binh T. Nguyen et al.

It is certified that error appears in the above-identified patent and that said Letters Patent is hereby corrected as shown below:

On the Title Page, in Item [75], under Inventors, at lines 1-3, please delete "Binh T Nguyen" and insert --Binh T. Nguyen--, please delete "Paul M Consigny" and insert --Paul M. Consigny--, and please delete "Michael J Leonard" and insert --Michael J. Leonard--.

Signed and Sealed this
Thirty-first Day of May, 2016

Michelle K. Lee
*Director of the United States Patent and Trademark Office*